(12) United States Patent
Dejima et al.

(10) Patent No.: US 11,241,145 B2
(45) Date of Patent: **\*Feb. 8, 2022**

(54) ENDOSCOPIC SURGERY DEVICE AND OUTER TUBE

(71) Applicant: FUJIFILM Corporation, Tokyo (JP)

(72) Inventors: Takumi Dejima, Ashigarakami-gun (JP); Nobuyuki Torisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

This patent is subject to a terminal disclaimer.

(21) Appl. No.: 16/457,465

(22) Filed: Jun. 28, 2019

(65) Prior Publication Data

US 2019/0320883 A1 Oct. 24, 2019

Related U.S. Application Data

(60) Division of application No. 14/550,552, filed on Nov. 21, 2014, now Pat. No. 10,376,135, which is a
(Continued)

(30) Foreign Application Priority Data

May 25, 2012 (JP) .............................. JP2012-120319

(51) Int. Cl.
*A61B 1/00* (2006.01)
*A61B 1/04* (2006.01)
(Continued)

(52) U.S. Cl.
CPC ........ *A61B 1/00154* (2013.01); *A61B 1/0014* (2013.01); *A61B 1/00135* (2013.01);
(Continued)

(58) Field of Classification Search
CPC ............ A61B 17/3423; A61B 17/3427; A61B 17/3429; A61B 17/0218; A61B 17/0281;
(Continued)

(56) References Cited

U.S. PATENT DOCUMENTS

| 4,538,594 A | 9/1985 | Boebel et al. |
| 5,012,818 A * | 5/1991 | Joishy ................ A61B 10/0045 |
| | | 600/567 |

(Continued)

FOREIGN PATENT DOCUMENTS

| EP | 1 582 138 A2 | 10/2005 |
| EP | 2238932 A2 | 10/2010 |

(Continued)

OTHER PUBLICATIONS

Japanese Office Action, dated Apr. 16, 2018, for corresponding Japanese Application No. 2017-124159, with an English machine translation.

(Continued)

*Primary Examiner* — Ryan N Henderson
(74) *Attorney, Agent, or Firm* — Birch, Stewart, Kolasch & Birch, LLP

(57) ABSTRACT

An object of the present invention is to provide an endoscopic surgery device and an outer tube, capable of easily obtaining an image desired by an operator to facilitate treatment as well as of performing minimally invasive surgery. In the endoscopic surgery device and the outer tube, an endoscope and a treatment tool are inserted into a body cavity through an outer tube. The outer tube is provided with a built-in slider. The slider is provided so as to be axially movable in the outer tube body. The endoscope and the treatment tool, inserted into the outer tube, are held by the (Continued)

slider. Moving the treatment tool allows endoscope to be moved in conjunction with the movement of the treatment tool.

20 Claims, 34 Drawing Sheets

Related U.S. Application Data continuation of application No. PCT/JP2013/064183, filed on May 22, 2013.

(51) Int. Cl.
*A61B 1/313* (2006.01)
*A61B 17/34* (2006.01)
*A61B 17/00* (2006.01)

(52) U.S. Cl.
CPC .......... *A61B 1/00147* (2013.01); *A61B 1/042* (2013.01); *A61B 1/3132* (2013.01); *A61B 17/00234* (2013.01); *A61B 17/3423* (2013.01); *A61B 17/3462* (2013.01); *A61B 17/3421* (2013.01); *A61B 2017/347* (2013.01); *A61B 2017/3441* (2013.01); *A61B 2017/3445* (2013.01)

(58) Field of Classification Search
CPC ........ A61B 17/0293; A61B 2017/3445; A61B 2017/3447; A61B 2017/345; A61B 2017/347; A61B 1/00131; A61B 1/00135; A61B 1/00154; A61B 1/0133; A61B 1/014; A61B 1/016; A61B 1/01; A61B 1/313; A61B 1/3132

See application file for complete search history.

(56) References Cited

U.S. PATENT DOCUMENTS

| | | | | |
|---|---|---|---|---|
| 5,167,220 A * | 12/1992 | Brown | A61B 1/12 | 600/156 |
| 5,569,205 A | 10/1996 | Hart et al. | | |
| 5,634,911 A | 6/1997 | Hermann et al. | | |
| 5,954,731 A * | 9/1999 | Yoon | A61B 17/062 | 606/144 |
| 5,993,466 A * | 11/1999 | Yoon | A61B 17/062 | 606/144 |
| 5,993,467 A * | 11/1999 | Yoon | A61B 17/0469 | 606/147 |
| 6,126,665 A * | 10/2000 | Yoon | A61B 17/0469 | 606/144 |
| 6,315,714 B1 | 11/2001 | Akiba | | |
| 7,105,009 B2 * | 9/2006 | Johnson | A61B 17/3498 | 604/167.03 |
| 7,727,255 B2 * | 6/2010 | Taylor | A61B 17/3423 | 606/205 |
| 7,942,834 B2 * | 5/2011 | Yamada | A61B 1/018 | 601/2 |
| 8,021,339 B2 * | 9/2011 | Rockrohr | A61B 17/3498 | 604/167.04 |
| 8,905,973 B2 * | 12/2014 | Tegg | A61B 17/3498 | 604/167.03 |
| 8,906,014 B2 * | 12/2014 | Bacher | A61B 17/29 | 606/46 |
| 9,179,933 B2 * | 11/2015 | Davis | A61B 17/3423 | |
| 9,314,267 B2 * | 4/2016 | Piskun | A61B 17/3439 | |
| 9,826,887 B2 * | 11/2017 | Dejima | A61B 1/00154 | |
| 10,165,933 B2 * | 1/2019 | Dejima | A61B 1/00135 | |
| 2001/0049497 A1 | 12/2001 | Kalloo et al. | | |
| 2003/0055437 A1 * | 3/2003 | Yasunaga | A61B 1/00154 | 606/130 |
| 2003/0135091 A1 | 7/2003 | Nakanawa et al. | | |
| 2004/0167559 A1 * | 8/2004 | Taylor | A61B 17/3423 | 606/185 |
| 2005/0085774 A1 * | 4/2005 | Streifinger | A61B 17/3498 | 604/167.01 |
| 2005/0119525 A1 * | 6/2005 | Takemoto | A61B 1/00137 | 600/114 |
| 2005/0182292 A1 * | 8/2005 | Suzuki | A61B 1/00137 | 600/104 |
| 2005/0203559 A1 * | 9/2005 | O'Heeron | A61B 17/3417 | 606/185 |
| 2005/0222495 A1 | 10/2005 | Okada et al. | | |
| 2006/0247495 A1 * | 11/2006 | Bacher | A61B 18/1445 | 600/106 |
| 2007/0049966 A1 * | 3/2007 | Bonadio | A61B 17/3423 | 606/206 |
| 2007/0265502 A1 * | 11/2007 | Minosawa | A61B 17/3421 | 600/173 |
| 2008/0033450 A1 * | 2/2008 | Bayer | A61B 17/3417 | 606/108 |
| 2008/0262296 A1 * | 10/2008 | Suzuki | A61B 1/00133 | 600/106 |
| 2008/0287963 A1 | 11/2008 | Rogers et al. | | |
| 2009/0093752 A1 | 4/2009 | Richard et al. | | |
| 2009/0203961 A1 * | 8/2009 | Regadas | A61B 1/31 | 600/106 |
| 2009/0227843 A1 * | 9/2009 | Smith | A61B 17/3423 | 600/208 |
| 2009/0259105 A1 * | 10/2009 | Miyano | A61B 17/0483 | 600/127 |
| 2009/0259172 A1 | 10/2009 | Yamaoka et al. | | |
| 2009/0270680 A1 * | 10/2009 | Takada | A61B 1/31 | 600/118 |
| 2010/0004600 A1 * | 1/2010 | Rockrohr | A61B 17/3421 | 604/167.04 |
| 2010/0016659 A1 | 1/2010 | Weitzner | | |
| 2010/0069710 A1 * | 3/2010 | Yamatani | A61B 1/018 | 600/102 |
| 2010/0081880 A1 * | 4/2010 | Widenhouse | A61B 1/018 | 600/201 |
| 2010/0113886 A1 * | 5/2010 | Piskun | A61B 17/0218 | 600/231 |
| 2010/0198006 A1 | 8/2010 | Greenburg et al. | | |
| 2010/0241082 A1 * | 9/2010 | Taylor | A61M 39/06 | 604/167.03 |
| 2010/0249516 A1 * | 9/2010 | Shelton, IV | A61B 17/0293 | 600/203 |
| 2010/0262080 A1 * | 10/2010 | Shelton, IV | A61B 17/3423 | 604/164.09 |
| 2010/0312063 A1 * | 12/2010 | Hess | A61B 17/3423 | 600/204 |
| 2011/0060183 A1 * | 3/2011 | Castro | A61B 17/3421 | 600/104 |
| 2011/0082343 A1 * | 4/2011 | Okoniewski | A61B 17/0293 | 600/208 |
| 2011/0124960 A1 | 5/2011 | St. Onge et al. | | |
| 2011/0152859 A1 | 6/2011 | Long et al. | | |
| 2011/0184231 A1 | 7/2011 | Page et al. | | |
| 2011/0230713 A1 * | 9/2011 | Kleemann | A61B 1/00165 | 600/106 |
| 2011/0282155 A1 | 11/2011 | Kase et al. | | |
| 2011/0295074 A1 * | 12/2011 | Stefanchik | A61B 17/3423 | 600/201 |
| 2012/0130177 A1 * | 5/2012 | Davis | A61B 17/3423 | 600/201 |
| 2012/0232339 A1 * | 9/2012 | Csiky | A61B 1/00135 | 600/104 |
| 2012/0253132 A1 * | 10/2012 | Davis | A61B 17/3423 | 600/201 |
| 2012/0253133 A1 * | 10/2012 | Okoniewski | A61B 1/00135 | 600/201 |
| 2012/0253383 A1 * | 10/2012 | Russo | A61B 17/3423 | 606/201 |
| 2012/0316391 A1 * | 12/2012 | Weitzner | A61B 17/00234 | 600/104 |
| 2014/0051934 A1 * | 2/2014 | Ma | A61B 17/3423 | 600/208 |

(56) References Cited

U.S. PATENT DOCUMENTS

| | | | | |
|---|---|---|---|---|
| 2014/0100421 | A1* | 4/2014 | Dejima | A61B 1/00052 600/101 |
| 2014/0128671 | A1* | 5/2014 | Riek | A61B 17/30 600/104 |
| 2014/0207070 | A1* | 7/2014 | Tegg | A61B 17/3498 604/167.05 |
| 2014/0275796 | A1* | 9/2014 | McGrogan | A61B 34/30 600/208 |
| 2015/0080650 | A1* | 3/2015 | Dejima | A61B 17/00234 600/102 |
| 2015/0250498 | A1* | 9/2015 | Kikuchi | A61B 17/3462 604/67 |
| 2016/0113638 | A1* | 4/2016 | Malkowski | A61B 17/0218 606/130 |
| 2016/0174825 | A1 | 6/2016 | Dejima | |
| 2016/0174826 | A1* | 6/2016 | Dejima | A61B 1/00154 600/104 |
| 2017/0049474 | A1* | 2/2017 | Piskun | A61B 17/0218 |
| 2017/0215919 | A1* | 8/2017 | Shelton, IV | A61B 17/3431 |

FOREIGN PATENT DOCUMENTS

| | | |
|---|---|---|
| JP | 2002-330928 A | 11/2002 |
| JP | 2003-88532 A | 3/2003 |
| JP | 2003-325436 A | 11/2003 |
| JP | 2004-41580 A | 2/2004 |
| JP | 2004-141486 A | 5/2004 |
| JP | 2004-180858 A | 7/2004 |
| JP | 2005-152416 A | 6/2005 |
| JP | 2005-192707 A | 7/2005 |
| JP | 2005-287963 A | 10/2005 |
| JP | 2011-528576 A | 11/2011 |
| JP | 2012-501695 A | 1/2012 |
| JP | 2012-505055 A | 3/2012 |
| WO | WO 2010/009292 A1 | 1/2010 |
| WO | WO 2010/042913 A2 | 4/2010 |
| WO | WO 2011/014711 A1 | 2/2011 |
| WO | WO 2013/176167 A1 | 11/2013 |
| WO | WO 2015/033908 A1 | 3/2015 |

OTHER PUBLICATIONS

Japanese Office Action, dated May 24, 2017, for corresponding Japanese Application No. 2016-195766, with an English machine translation.

U.S. Office Action, dated Apr. 24, 2017, for U.S. Appl. No. 15/058,164.

U.S. Office Action, dated Dec. 19, 2017, for U.S. Appl. No. 15/058,164.

U.S. Office Action, dated Dec. 20, 2017, for U.S. Appl. No. 15/058,176.

U.S. Office Action, dated Dec. 21, 2017, for U.S. Appl. No. 15/058,111.

U.S. Office Action, dated May 3, 2017, for U.S. Appl. No. 15/058,176.

U.S. Office Action, dated May 5, 2017, for U.S. Appl. No. 15/058,111.

U.S. Office Action, dated Sep. 27, 2016, for U.S. Appl. No. 15/058,111.

U.S. Office Action, dated Sep. 27, 2016, for U.S. Appl. No. 15/058,176.

U.S. Office Action, dated Sep. 29, 2016, for U.S. Appl. No. 15/058,164.

Written Opinion of the International Searching Authority (form PCT/ISA/237), dated Oct. 14, 2014, for corresponding International Application No. PCT/JP2014/072991, with an English translation.

Written Opinion of the International Searching Authority (form PCT/ISA/237), dated Oct. 14, 2014, for corresponding International Application No. PCT/JP2014/072992, with an English translation.

Written Opinion of the International Searching Authority (form PCT/ISA/237), dated Oct. 28, 2014, for corresponding International Application No. PCT/JP2014/072988, with an English translation.

Written Opinion of the International Searching Authority (form PCT/ISA/237), dated Oct. 28, 2014, for corresponding International Application No. PCT/JP2014/072989, with an English translation.

European Office Action for European Application No. 13794761.0, dated Oct. 4, 2019.

International Search Report, dated Jun. 25, 2013, issued in PCT/JP2013/064183.

Written Opinion of the International Searching Authority, dated Jun. 25, 2013, issued in PCT/JP2013/064183.

Extended European Search Report, dated Dec. 8, 2015, for corresponding European Application No. 13794761.0.

Notice of Allowance dated Apr. 11, 2019 in copending U.S. Appl. No. 14/550,552.

Office Action dated Jan. 25, 2019 in copending U.S. Appl. No. 14/550,552.

Office Action dated Jan. 26, 2017 in copending U.S. Appl. No. 14/550,552.

Office Action dated May 17, 2017 in copending U.S. Appl. No. 14/550,552.

Office Action dated Sep. 28, 2018 in copending U.S. Appl. No. 14/550,552.

* cited by examiner

FIG.13
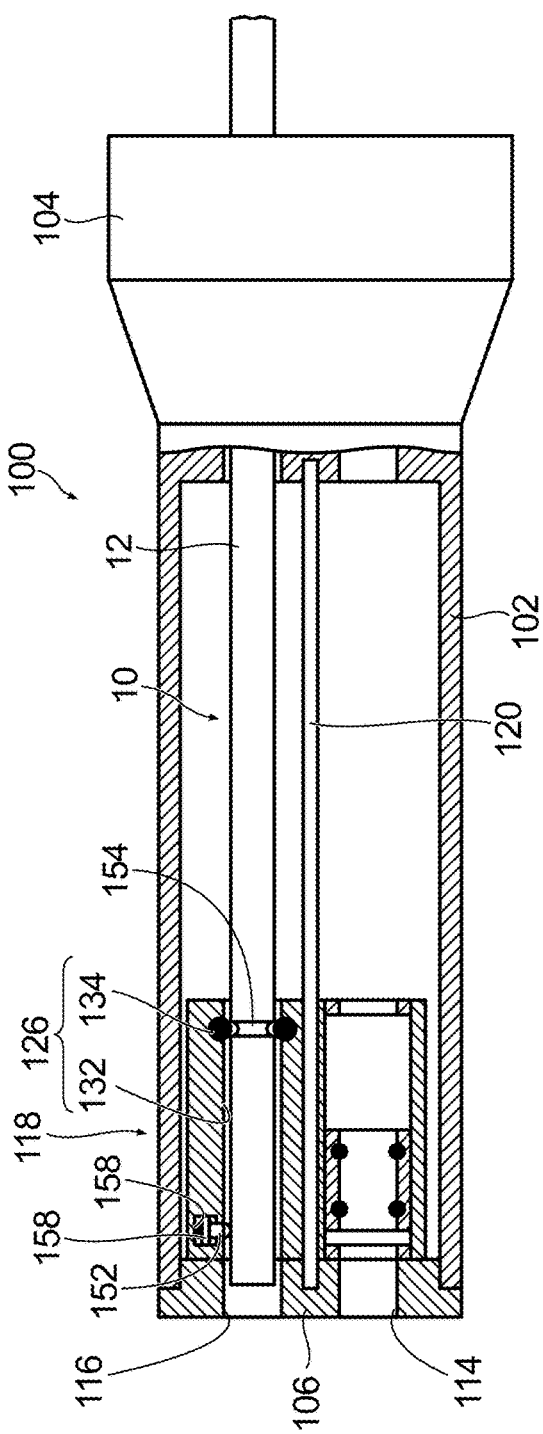
(A)
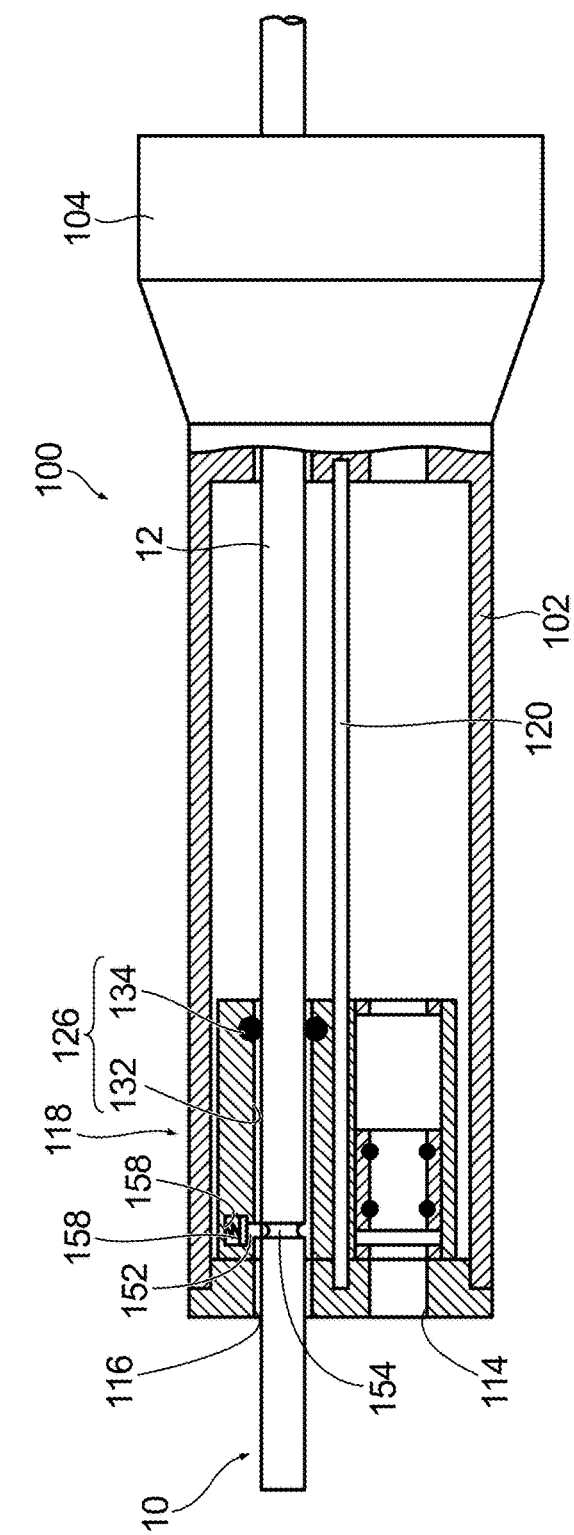
(B)

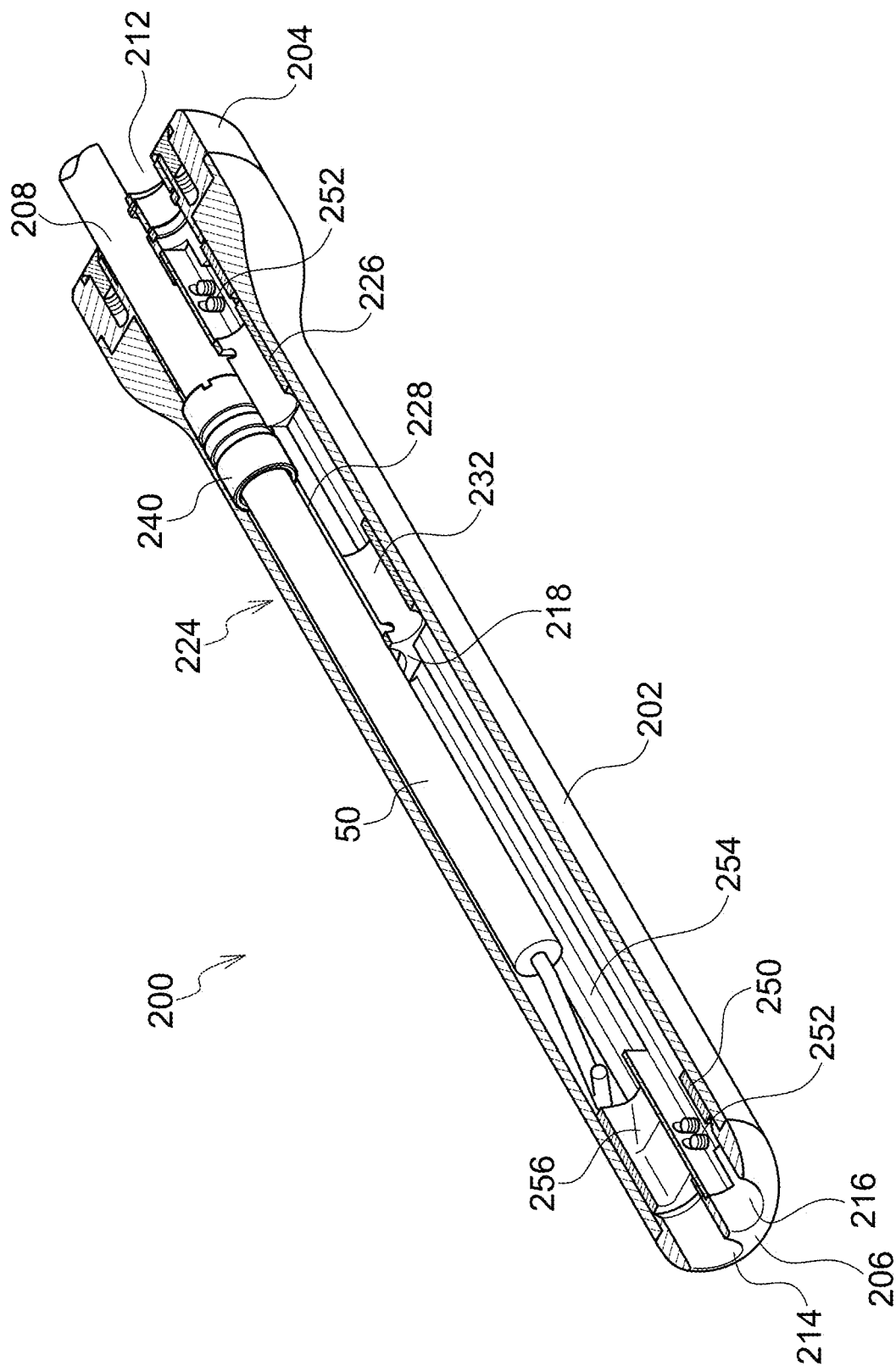

ENDOSCOPIC SURGERY DEVICE AND OUTER TUBE

CROSS-REFERENCE TO RELATED APPLICATIONS

This application is a Divisional of U.S. patent application Ser. No. 14/550,552, filed Nov. 21, 2014, which is a Continuation of PCT International Application No. PCT/JP2013/064183 filed on May 22, 2013, which claims priority under 35 U.S.C § 119(a) to Japanese Patent Application No. 2012-120319 filed on May 25, 2012. Each of the above applications is hereby expressly incorporated by reference, in their entirety, into the present application.

BACKGROUND OF THE INVENTION

Field of the Invention

The present invention relates to an endoscopic surgery device and an outer tube, and more particularly to an endoscopic surgery device and an outer tube that are configured to interlock an endoscope with a treatment tool.

Description of the Related Art

There is known a laparoscope as an endoscope instrument that is to be inserted into an abdominal cavity through body surface skin. In recent years, an operation using the laparoscope (laparoscopic surgery) has become widespread in many operations because an operative wound is made smaller as compared with laparotomy, thoracotomy, and the like, to allow a postoperative bed rest period to be shortened.

In general, in laparoscopic surgery (such as laparoscopic cholecystectomy), there are an operator for performing treatment and an endoscopist for operating a laparoscope, so that the treatment and operation of the laparoscope are separately performed. Thus, during a surgical operation, the operator performs the treatment while sequentially giving instruction to the endoscopist to obtain an optimum image for performing the treatment.

Unfortunately, in a method in which an operator gives an instruction to an endoscopist, there is a problem in which it is difficult to obtain an image exactly desired by an operator, so that the operator is stressed. In addition, there is also a problem in which the endoscopist starts operation after received an instruction from the operator, so that it takes time for the operation. Further, there is also a problem in which operation is complicated because a hand of the operator and a hand of the endoscopist may interfere with each other on the abdominal wall of a patient.

Japanese Patent Application Laid-Open No. 2004-141486 (PTL 1) proposes an endoscopic surgery system using an endoscope and multi-degree-of-freedom forceps in combination with each other, which endoscopic surgery system detects an observation state of the endoscope to regulate an operation range of the multi-degree-of-freedom forceps in accordance with the detected result, thereby preventing the multi-degree-of-freedom forceps from deviating from an observation field of view of the endoscope.

In addition, Japanese Patent Application Laid-Open No. 2003-325436 (PTL 2) proposes an endoscopic surgery system in which an endoscope which can move an observation field of a distal end part of the endoscope by bending a bending portion and a treatment tool which is inserted into a body cavity to treat an operative site are used in combination with each other, wherein the distal end part of the endoscope and the treatment tool are coupled with each other by using coupling means and the bending portion of the endoscope can be moved (so-called oscillating operation) by tilting operation of the treatment tool.

SUMMARY OF THE INVENTION

Unfortunately, there is a problem in which, if an operation range of a treatment tool is regulated by detecting an observation state of the endoscope as described in PTL 1, an originally possible movement is limited to cause treatment to conversely become difficult. In addition, since the operation range of the treatment tool is regulated by detecting the observation state of the endoscope, there is a drawback of enlarging the system.

In addition, in a method of operating a bending portion of an endoscope by tilting operation of a treatment tool, as described in PTL 2, there is a problem in which it is required to enlarge an incision range of a portion into which the endoscope is to be inserted so that the treatment tool can be tilted with respect to the endoscope, thereby increasing a burden to a body.

The present invention is made in light of the above-mentioned circumstances, and aims to provide an endoscopic surgery device and an outer tube, capable of easily obtaining an image desired by an operator to facilitate treatment as well as of performing minimally invasive surgery (fewer burdens to a body).

Solution to Problem

Means for solving the problem above is as follows.

A first aspect is an endoscopic surgery device including: an endoscope which has an insertion section and observes in a body cavity; a treatment tool which includes an insertion section whose distal end has a treatment portion; and an outer tube into which the insertion section of the endoscope and the insertion section of the treatment tool are inserted, and which guides the insertion section of the endoscope and the insertion section of the treatment tool into the body cavity, wherein the outer tube includes: a cylindrical outer tube body into which the insertion section of the endoscope and the insertion section of the treatment tool are to be inserted; a mobile object provided in the outer tube body so as to be movable in the outer tube body in a direction parallel to an axis of the outer tube body; an endoscope holding section which is provided in the mobile object and holds the insertion section of the endoscope inserted into the outer tube body parallelly to the axis of the outer tube body; and a treatment tool holding section which is provided in the mobile object and holds the insertion section of the treatment tool inserted into the outer tube body parallelly to the axis of the outer tube body.

According to the first aspect, the endoscope and the treatment tool are inserted into a body cavity through the outer tube. The outer tube is provided in its cylindrical outer tube body with the mobile object to which the endoscope and the treatment tool are held parallel to each other as well as parallel to the axis of the outer tube body of the outer tube. The mobile object is provided so as to be movable in the direction parallel to the axis of the outer tube body of the outer tube, so that when the treatment tool is axially moved, the endoscope is also axially moved in conjunction with the treatment tool. Accordingly, it is possible to allow a field of view of the endoscope (imaging region) to track a treatment portion, thereby enabling an optimum image for the treatment to be constantly supplied to an operator (an image desired by the operator can be displayed without stress). In addition, since the endoscope and the treatment tool are inserted into a body cavity through the outer tube, only one pierced portion is required in a body cavity wall to enable minimally invasive surgery (fewer burdens to a body). While movement in a fore-and-aft direction of the field of view of the endoscope (reciprocating) is performed by axial movement of the treatment tool, vertical and horizontal movement thereof is performed by tilting of the treatment tool. That is, the field of view is moved by tilting the whole of the endoscopic surgery device including the outer tube. In this case, since the field of view can be moved by tilting of the outer tube, it is unnecessary to enlarge an incised portion in order to perform treatment and movement of the field of view, thereby enabling minimally invasive surgery to be performed.

A second aspect is a mode of the endoscopic surgery device of the first aspect above in which the treatment tool holding section holds the insertion section of the treatment tool in a movable manner in the direction parallel to the axis of the outer tube body with respect to the mobile object within a predetermined movable range.

According to the second aspect, the treatment tool held by the mobile object is held so as to be axially movable with respect to the mobile object within the predetermined movable range. Accordingly, it is possible to allow interlock operation between the treatment tool and the endoscope to have a "play". That is, it is possible to prevent movement of the treatment tool from being transmitted to the endoscope within the predetermined range (movable range). Allowing the interlock operation between the treatment tool and the endoscope as above to have a "play" can prevent a screen from shaking when the treatment tool is slightly axially displaced (when reciprocated at a small amplitude), for example. As a result, it is possible to constantly provide an easily visible image for an operator.

A third aspect is a mode of the endoscopic surgery device of the second aspect above in which the treatment tool holding section includes: a cylindrical second mobile object which is provided so as to be movable in a direction parallel to the axis of the outer tube body with respect to the mobile object, and into which the insertion section of the treatment tool is inserted; and an elastic body which is arranged in the second mobile object, and presses and holds the insertion section of the treatment tool inserted into the second mobile object.

According to the third aspect, the treatment tool holding section includes the cylindrical second mobile object that is provided so as to be movable in a direction parallel to the axis of the outer tube body with respect to the mobile object, and into which the insertion section of the treatment tool is inserted, and an elastic body arranged in the second mobile object to press and hold the insertion section of the treatment tool inserted into the second mobile object. Accordingly, the treatment tool can be provided so as to be axially movable with respect to the mobile object, so that it is possible to allow interlock operation between the treatment tool and the endoscope to have a "play".

A fourth aspect is a mode of the endoscopic surgery device of the third aspect above, wherein the mobile object is engaged with the outer tube body by a first frictional force and is provided so as to be movable in the direction parallel to the axis of the outer tube body, the elastic body is engaged with the insertion section of the treatment tool by a second frictional force larger than the first frictional force, and presses and holds the insertion section of the treatment tool, and the second mobile object is engaged with the mobile object by a third frictional force smaller than the first frictional force and is provided so as to be movable with respect to the mobile object in the direction parallel to the axis of the outer tube body.

According to the fourth aspect, the mobile object is engaged with the outer tube body by the first frictional force so as to be movable. In addition, the elastic body presses and holds the insertion section of the treatment tool by the second frictional force larger than the first frictional force. Further, the second mobile object is provided so as to be movable with respect to the mobile object by the third frictional force smaller than the first frictional force. Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool.

A fifth aspect is a mode of the endoscopic surgery device of any one of the first to fourth aspects above, in which the treatment tool holding section is capable of adjusting a holding position of the insertion section of the treatment tool with respect to the mobile object.

According to the fifth aspect, it is possible to adjust a holding position of the treatment tool with respect to the mobile object. That is, it is possible to adjust a relative positional relationship (a positional relationship of ends) between the endoscope and the treatment tool. As a result, it is possible to adjust a field of view (imaging region) of the endoscope as well as to further improve operability of the endoscope (it is possible to adjust a position of the endoscope so that an end of the treatment tool is readily visible).

A sixth aspect is a mode of the endoscopic surgery device of any one of the first to fifth aspects above, in which the treatment tool holding section holds the insertion section of the treatment tool in a detachable manner.

According to the sixth aspect, it is possible to attach the treatment tool to the outer tube in a detachable manner. As a result, it is possible to easily perform cleaning, maintenance, management, and the like of the treatment tool.

A seventh aspect is a mode of the endoscopic surgery device of any one of the first to sixth aspects above, in which the endoscope holding section holds the insertion section of the endoscope in a detachable manner.

According to the seventh aspect, it is possible to attach the endoscope to the outer tube in a detachable manner. As a result, it is possible to easily perform cleaning, maintenance, management, and the like of the endoscope.

A eighth aspect is a mode of the endoscopic surgery device of the seventh aspect above, which further includes: an endoscope lock pin provided in a retractable manner in either one of the insertion section of the endoscope and the endoscope holding section; a recessed portion provided in the other one thereof; and an endoscope lock pin urging member which urges the endoscope lock pin in a projecting direction, wherein, when the insertion section of the endoscope is inserted into the outer tube, the endoscope lock pin is fitted into the recessed portion to hold the insertion section of the endoscope in the endoscope holding section.

According to the eighth aspect, the endoscope lock pin is provided in either one of the insertion section of the endoscope and the endoscope holding section, and the recessed portion is provided in the other one thereof, and when the insertion section of the endoscope is inserted into the outer tube, the endoscope lock pin is fitted into the recessed portion to hold the insertion section of the endoscope in the endoscope holding section in a detachable manner. As a result, it is possible to easily attach the endoscope in a predetermined position with respect to the mobile object.

A ninth aspect is a mode of the endoscopic surgery device of the seventh or the eighth aspect above, in which the endoscope holding section is capable of adjusting a holding position of the insertion section of the endoscope with respect to the mobile object.

According to the ninth aspect, it is possible to adjust a holding position of the endoscope with respect to the mobile object. That is, it is possible to adjust a relative positional relationship between the treatment tool and the endoscope. As a result, it is possible to adjust a field of view (imaging region) of the endoscope as well as to further improve operability of the endoscope.

A tenth aspect is a mode of the endoscopic surgery device of any one of the first to ninth aspects, in which the outer tube further includes a movement regulating member which regulates movement of the mobile object.

According to the tenth aspect, it is possible to arbitrarily regulate movement of the mobile object. As a result, it is possible to arbitrarily stop axial movement of the treatment tool and the endoscope to improve operability of the treatment tool and the endoscope. In addition, in a configuration in which the treatment tool and the endoscope are detachable, it is possible to easily attach and detach the treatment tool and the endoscope.

An eleventh aspect is an endoscopic surgery device including: an endoscope which has an insertion section and observes in a body cavity; a treatment tool which includes an insertion section whose distal end has a treatment portion; and an outer tube into which the insertion section of the endoscope and the insertion section of the treatment tool are inserted, and which guides the insertion section of the endoscope and the insertion section of the treatment tool into the body cavity, wherein the outer tube includes: a cylindrical outer tube body into which the insertion section of the endoscope and the insertion section of the treatment tool are to be inserted; a mobile object which is engaged with the outer tube body by a first frictional force and is provided so as to be movable in the outer tube body in a direction parallel to an axis of the outer tube body; an endoscope holding section which is provided in the mobile object and holds the insertion section of the endoscope parallelly to the axis of the outer tube body; and a treatment tool holding section which is provided in the mobile object, and is engaged with the insertion section of the treatment tool by a second frictional force larger than the first frictional force to hold the insertion section of the treatment tool parallelly to the axis of the outer tube body when the insertion section of the treatment tool is inserted into the outer tube body.

According to the eleventh aspect, the endoscope and the treatment tool are inserted into a body cavity through the outer tube. The outer tube is provided in its cylindrical outer tube body with the mobile object to which the endoscope and the treatment tool are held parallel to each other as well as parallel to the axis of the outer tube body of the outer tube. The mobile object is provided so as to be movable in the direction parallel to the axis of the outer tube body of the outer tube, so that when the treatment tool is axially moved, the endoscope is also axially moved in conjunction with the treatment tool. Accordingly, it is possible to allow a field of view of the endoscope (imaging region) to track a treatment portion, thereby enabling an optimum image for the treatment to be constantly supplied to an operator (an image desired by the operator can be displayed without stress). In addition, since the endoscope and the treatment tool are inserted into a body cavity through the outer tube, only one pierced portion is required in a body cavity wall to enable minimally invasive surgery (fewer burdens to a body). While movement in a fore-and-aft direction of the field of view of the endoscope (reciprocating) is performed by axial movement of the treatment tool, vertical and horizontal movement thereof is performed by tilting of the treatment tool. That is, the field of view is moved by tilting the whole of the endoscopic surgery device including the outer tube. In this case, since the field of view can be moved by tilting of the outer tube, it is unnecessary to enlarge an incised portion in order to perform treatment and movement of the field of view, thereby enabling minimally invasive surgery to be performed. Further, when inserted into the outer tube, the treatment tool is engaged with the treatment tool holding section and is held by using predetermined frictional force (second frictional force), so that it is possible to attach the treatment tool to the outer tube in a detachable manner. As a result, it is possible to easily perform cleaning, maintenance, management, and the like of the treatment tool. In addition, it is possible to easily perform attaching of the treatment tool to the mobile object and detaching thereof from the mobile object because the attaching and detaching are automatically performed by operation of inserting the treatment tool into the outer tube and removing it from the outer tube.

A twelfth aspect is a mode of the endoscopic surgery device of the eleventh aspect above, in which the treatment tool holding section includes a second mobile object which is engaged with the mobile object by a third frictional force smaller than the first frictional force so as to be movable with respect to the mobile object in the direction parallel to the axis of the outer tube body, and when the insertion section of treatment tool is inserted into the outer tube body, the insertion section of the treatment tool and the second mobile object are engaged with each other by the second frictional force.

According to the twelfth aspect, the treatment tool holding section is provided with the second mobile object that holds the treatment tool. The second mobile object is provided in the mobile object so as to be movable by engaging with the mobile object by frictional force (the third frictional force) smaller than frictional force (the first frictional force) between the outer tube body and the mobile object. When inserted into the outer tube, the treatment tool is engaged with the second mobile object by the second frictional force to be held by the second mobile object. Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool, whereby it is possible to provide a stable image to further facilitate treatment.

A thirteenth aspect is a mode of the endoscopic surgery device of the eleventh aspect above, in which the treatment tool holding section includes: a cylindrical second mobile object which is engaged with the mobile object by a third frictional force smaller than the first frictional force so as to be movable in a direction parallel to the axis of the outer tube body with respect to the mobile object, and into which the insertion section of the treatment tool is inserted; and an elastic body which is arranged in the second mobile object and is engaged with the insertion section of the treatment tool inserted into the second mobile object by the second frictional force to press and hold the insertion section of the treatment tool.

According to the thirteenth aspect, the treatment tool holding section is provided with the second mobile object that holds the treatment tool. The second mobile object is formed into a cylindrical shape, and is provided in the mobile object so as to be movable by engaging with the mobile object by frictional force (the third frictional force) smaller than frictional force (the first frictional force) between the outer tube body and the mobile object. In addition, the second mobile object is provided inside with the elastic body, and when inserted into the outer tube, the treatment tool is pressed and held to the second mobile object by the elastic body (engaged by the second frictional force and is pressed and held). Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool, whereby it is possible to provide a stable image to further facilitate treatment.

A fourteenth aspect is a mode of the endoscopic surgery device of any one of the eleventh to thirteenth aspects above, in which the outer tube further includes a movement regulating member which regulates movement of the mobile object.

According to the fourteenth aspect, it is possible to arbitrarily regulate movement of the mobile object. As a result, it is possible to arbitrarily stop axial movement of the treatment tool and the endoscope to improve operability of the treatment tool and the endoscope. In addition, in a configuration in which the treatment tool and the endoscope are detachable, it is possible to easily attach and detach the treatment tool and the endoscope.

A fifteenth aspect is a mode of the endoscopic surgery device of the fourteenth aspect above, in which the movement regulating member regulates movement of the mobile object when the mobile object moves in the outer tube body in a direction to a proximal end to reach a predetermined movement regulation position, and in a state where movement of the mobile object is regulated, when the insertion section of the treatment tool is inserted by a predetermined amount, the movement regulating member releases regulation of the movement of the mobile object.

According to the fifteenth aspect, movement of the mobile object is regulated when the mobile object moves in the outer tube body in the direction to the proximal end to reach the predetermined movement regulation position. In addition, in a state where movement of the mobile object is regulated, when the insertion section of the treatment tool is inserted by the predetermined amount, regulation of movement of the mobile object is released. The mobile object moves in conjunction with reciprocation of the treatment tool. When operation (operation of moving the treatment tool in the direction to the proximal end of the outer tube) of removing the treatment tool from the outer tube is performed, the mobile object moves in the direction to the proximal end to be locked at the predetermined position (movement regulation position). Insertion of the treatment tool is performed in a state where the mobile object is locked in the outer tube body, and when the treatment tool is inserted by the predetermined amount, the lock of the mobile object is released. As a result, it is possible to automatically set a relative positional relationship between the endoscope and the treatment tool as well as to further improve operability of the endoscope and the treatment tool.

A sixteenth aspect is a mode of the endoscopic surgery device of the fourteenth aspect above, in which the movement regulating member includes: a mobile object lock pin provided on a moving path of the mobile object in a retractable manner; a mobile object lock pin urging member which urges the mobile object lock pin in a projecting direction; and a mobile object lock releasing member which retracts the mobile object lock pin from the moving path of the mobile object against an urging force of the mobile object lock pin urging member.

According to the sixteenth aspect, the movement regulating member is configured to include: the mobile object lock pin provided on a moving path of the mobile object in a retractable manner; the mobile object lock pin urging member which urges the mobile object lock pin in the projecting direction; and the mobile object lock release member which retracts the mobile object lock pin from the moving path of the mobile object against urging force of the mobile object lock pin urging member. The mobile object lock pin is configured to project in the moving path of the mobile object to allow the mobile object lock pin to engage with the mobile object moving in the outer tube body of the outer tube so that movement of the mobile object is regulated. In a case of releasing regulation of movement of the mobile object, the mobile object lock pin is configured to retract from the moving path of the mobile object against urging force of the mobile object lock pin urging member.

A seventeenth aspect is a mode of the endoscopic surgery device of the sixteenth aspect above, in which, when the insertion section of the treatment tool is inserted into the outer tube body by a predetermined amount, the mobile object lock release member is engaged with the insertion section of the treatment tool to retract the mobile object lock pin from the moving path of the mobile object against urging force of the mobile object lock pin urging member.

According to the seventeenth aspect, when the insertion section of the treatment tool is inserted into the outer tube body by the predetermined amount, the insertion section of the treatment tool is engaged with the mobile object lock release member to retract the mobile object lock pin from the moving path of the mobile object against urging force of the mobile object lock pin urging member. As a result, when the treatment tool is inserted by the predetermined amount, the lock of the mobile object can be automatically released and a relative positional relationship between the endoscope and the treatment tool can be automatically set.

A eighteenth aspect is a mode of the endoscopic surgery device of any one of aspects 11 to 17 above, in which the endoscope holding section holds the insertion section of the endoscope in a detachable manner.

According to the eighteenth aspect, it is possible to attach the endoscope to the outer tube in a detachable manner. As a result, it is possible to easily perform cleaning, maintenance, management, and the like of the endoscope.

A nineteenth aspect is a mode of the endoscopic surgery device of the eighteenth aspect above, further including: an endoscope lock pin provided in a retractable manner in either one of the insertion section of the endoscope and the endoscope holding section; a recessed portion provided in the other one thereof; and an endoscope lock pin urging member which urges the endoscope lock pin in a projecting direction, wherein, when the insertion section of the endoscope is inserted into the outer tube, the endoscope lock pin is fitted into the recessed portion to hold the insertion section of the endoscope in the endoscope holding section.

According to the nineteenth aspect, the endoscope lock pin is provided in either one of the insertion section of the endoscope and the endoscope holding section, and the recessed portion is provided in the other one thereof, and when the insertion section of the endoscope is inserted into the outer tube, the endoscope lock pin is fitted into the recessed portion to hold the insertion section of the endoscope in the endoscope holding section in a detachable manner. As a result, it is possible to easily attach the endoscope in a predetermined position with respect to the mobile object.

A twentieth aspect is a mode of the endoscopic surgery device of the eighteenth aspect above, in which the endoscope holding section is capable of adjusting a holding position of the insertion section of the endoscope with respect to the mobile object.

According to the twentieth aspect, it is possible to adjust a holding position of the endoscope with respect to the mobile object. That is, it is possible to adjust a relative positional relationship between the treatment tool and the endoscope. As a result, it is possible to adjust a field of view (imaging region) of the endoscope as well as to further improve operability of the endoscope.

A twenty first aspect is an outer tube into which an insertion section of an endoscope that has the insertion section and observes in a body cavity, and an insertion section of a treatment tool that includes the insertion section whose distal end has a treatment portion, are inserted, the outer tube which guides the insertion section of the endoscope and the insertion section of the treatment tool into the body cavity, wherein the outer tube includes: a cylindrical outer tube body into which the insertion section of the endoscope and the insertion section of the treatment tool are to be inserted; a mobile object provided in the outer tube body so as to be movable in the outer tube body in a direction parallel to an axis of the outer tube body; an endoscope holding section which is provided in the mobile object and holds the insertion section of the endoscope inserted into the outer tube body parallelly to the axis of the outer tube body; and a treatment tool holding section which is provided in the mobile object and holds the insertion section of the treatment tool inserted into the outer tube body parallelly to the axis of the outer tube body.

According to the twenty first aspect, the endoscope and the treatment tool are inserted into a body cavity through the outer tube. The outer tube is provided in its cylindrical outer tube body with the mobile object to which the endoscope and the treatment tool are held parallelly to each other as well as parallelly to the axis of the outer tube body of the outer tube. The mobile object is provided so as to be movable in the direction parallel to the axis of the outer tube body of the outer tube, so that when the treatment tool is axially moved, the endoscope is also axially moved in conjunction with the treatment tool. Accordingly, it is possible to allow a field of view of the endoscope (imaging region) to track a treatment portion, thereby enabling an optimum image for the treatment to be constantly supplied to an operator (an image desired by the operator can be displayed without stress). In addition, since the endoscope and the treatment tool are inserted into a body cavity through the outer tube, only one pierced portion is required in a body cavity wall to enable minimally invasive surgery (fewer burdens to a body). While movement in a fore-and-aft direction of the field of view of the endoscope (reciprocating) is performed by axial movement of the treatment tool, vertical and horizontal movement thereof is performed by tilting of the treatment tool. That is, the field of view is moved by tilting the whole of the endoscopic surgery device including the outer tube. In this case, since the field of view can be moved by tilting of the outer tube, it is unnecessary to enlarge an incised portion in order to perform treatment and movement of the field of view, thereby enabling minimally invasive surgery to be performed.

A twenty second aspect is a mode of the outer tube of the twenty first aspect above, in which the treatment tool holding section holds the insertion section of the treatment tool in a movable manner in the direction parallel to the axis of the outer tube body with respect to the mobile object within a predetermined movable range.

According to the twenty second aspect, the treatment tool held by the mobile object is held so as to be axially movable with respect to the mobile object within the predetermined movable range. Accordingly, it is possible to allow interlock operation between the treatment tool and the endoscope to have a "play". That is, it is possible to prevent movement of the treatment tool from being transmitted to the endoscope within the predetermined range (movable range). Allowing the interlock operation between the treatment tool and the endoscope as above to have a "play" can prevent a screen from shaking when the treatment tool is slightly axially displaced (when reciprocated at a small amplitude), for example. As a result, it is possible to constantly provide an easily visible image for an operator.

A twenty third aspect is a mode of the outer tube of the twenty second aspect above, in which the treatment tool holding section includes: a cylindrical second mobile object which is provided so as to be movable in a direction parallel to the axis of the outer tube body with respect to the mobile object, and into which the insertion section of the treatment tool is inserted; and an elastic body which is arranged in the second mobile object, and presses and holds the insertion section of the treatment tool inserted into the second mobile object.

According to the twenty third aspect, the treatment tool holding section includes: the cylindrical second mobile object that is provided so as to be movable in a direction parallel to the axis of the outer tube body with respect to the mobile object, and into which the insertion section of the treatment tool is inserted; and the elastic body which is arranged in the second mobile object, and presses and holds the insertion section of the treatment tool inserted into the second mobile object. Accordingly, the treatment tool can be provided so as to be axially movable with respect to the mobile object, so that it is possible to allow interlock operation between the treatment tool and the endoscope to have a "play".

A twenty fourth aspect is a mode of the outer tube of the twenty third aspect above in which: the mobile object is engaged with the outer tube body by a first frictional force and is provided so as to be movable in the direction parallel to the axis of the outer tube body; the elastic body is engaged with the insertion section of the treatment tool by a second frictional force larger than the first frictional force, and presses and holds the insertion section of the treatment tool; and the second mobile object is engaged with the mobile object by a third frictional force smaller than the first frictional force and is provided so as to be movable with respect to the mobile object in the direction parallel to the axis of the outer tube body.

According to the twenty fourth aspect, the mobile object is engaged with the outer tube body by the first frictional force and is provided so as to be movable. In addition, the elastic body presses and holds the insertion section of the treatment tool by the second frictional force larger than the first frictional force. Further, the second mobile object is provided so as to be movable with respect to the mobile object by the third frictional force smaller than the first frictional force. Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool.

A twenty fifth aspect is a mode of the outer tube of any one of the twenty first to twenty fourth aspects above, in which the treatment tool holding section is capable of adjusting a holding position of the insertion section of the treatment tool with respect to the mobile object.

According to the twenty fifth aspect, it is possible to adjust a holding position of the treatment tool with respect to the mobile object. That is, it is possible to adjust a relative positional relationship (a positional relationship of ends) between the endoscope and the treatment tool. As a result, it is possible to adjust a field of view (imaging region) of the endoscope as well as to improve operability of the endoscope (it is possible to adjust a position of the endoscope so that an end of the treatment tool is readily visible).

A twenty sixth aspect is a mode of the outer tube of any one of the twenty first to twenty fifth aspects above, in which the treatment tool holding section holds the insertion section of the treatment tool in a detachable manner.

According to the twenty sixth aspect, it is possible to attach the treatment tool to the outer tube in a detachable manner. As a result, it is possible to easily perform cleaning, maintenance, management, and the like of the treatment tool.

A twenty seventh aspect is a mode of the outer tube of any one of the twenty first to twenty sixth aspects above, in which the endoscope holding section holds the insertion section of the endoscope in a detachable manner.

According to the twenty seventh aspect, it is possible to attach the endoscope to the outer tube in a detachable manner. As a result, it is possible to easily perform cleaning, maintenance, management, and the like of the endoscope.

A twenty eighth aspect is a mode of the outer tube of the twenty seventh aspect above, which further includes: an endoscope lock pin provided in a retractable manner in either one of the insertion section of the endoscope and the endoscope holding section; a recessed portion provided in the other one thereof; and an endoscope lock pin urging member which urges the endoscope lock pin in a projecting direction, wherein, when the insertion section of the endoscope is inserted into the outer tube, the endoscope lock pin is fitted into the recessed portion to hold the insertion section of the endoscope in the endoscope holding section.

According to the twenty eighth aspect, the endoscope lock pin is provided in either one of the insertion section of the endoscope and the endoscope holding section, and the recessed portion is provided in the other one thereof, and when the insertion section of the endoscope is inserted into the outer tube, the endoscope lock pin is fitted into the recessed portion to hold the insertion section of the endoscope in the endoscope holding section in a detachable manner. As a result, it is possible to easily attach the endoscope in a predetermined position with respect to the mobile object.

A twenty ninth aspect is a mode of the outer tube of the twenty seventh or the twenty eighth aspect above, in which the endoscope holding section is capable of adjusting a holding position of the insertion section of the endoscope with respect to the mobile object.

According to the twenty ninth aspect, it is possible to adjust a holding position of the endoscope with respect to the mobile object. That is, it is possible to adjust a relative positional relationship between the treatment tool and the endoscope. As a result, it is possible to adjust a field of view (imaging region) of the endoscope as well as to further improve operability of the endoscope.

A thirty aspect is a mode of the outer tube of any one of the twenty first to twenty ninth aspects above, which further includes a movement regulating member which regulates movement of the mobile object.

According to the thirty aspect, it is possible to arbitrarily regulate movement of the mobile object. As a result, it is possible to arbitrarily stop axial movement of the treatment tool and the endoscope to improve operability of the treatment tool and the endoscope. In addition, in a configuration in which the treatment tool and the endoscope are detachable, it is possible to easily attach and detach the treatment tool and the endoscope.

A thirty first aspect is an outer tube into which an insertion section of an endoscope that has the insertion section and that observes in a body cavity, and an insertion section of a treatment tool that includes an insertion section whose distal end has a treatment portion, are inserted, the outer tube which guides the insertion section of the endoscope and the insertion section of the treatment tool into the body cavity, wherein the outer tube includes: a cylindrical outer tube body into which the insertion section of the endoscope and the insertion section of the treatment tool are to be inserted; a mobile object which is engaged with the outer tube body by a first frictional force and is provided so as to be movable in the outer tube body in a direction parallel to the axis of the outer tube body; an endoscope holding section which is provided in the mobile object and holds the insertion section of the endoscope parallelly to the axis of the outer tube body; and a treatment tool holding section which is provided in the mobile object and is engaged with the insertion section of the treatment tool by a second frictional force larger than the first frictional force to hold the insertion section of the treatment tool parallelly to the axis of the outer tube body when the insertion section of the treatment tool is inserted into the outer tube body.

According to the thirty first aspect, the endoscope and the treatment tool are inserted into a body cavity through the outer tube. The outer tube is provided in its cylindrical outer tube body with the mobile object to which the endoscope and the treatment tool are held parallelly to each other as well as parallelly to the axis of the outer tube body of the outer tube. The mobile object is provided so as to be movable in the direction parallel to the axis of the outer tube body of the outer tube, so that when the treatment tool is axially moved, the endoscope is also axially moved in conjunction with the treatment tool. Accordingly, it is possible to allow a field of view of the endoscope (imaging region) to track a treatment portion, thereby enabling an optimum image for the treatment to be constantly supplied to an operator (an image desired by the operator can be displayed without stress). In addition, since the endoscope and the treatment tool are inserted into a body cavity through the outer tube, only one pierced portion is required in a body cavity wall to enable minimally invasive surgery (fewer burdens to a body). While movement in a fore-and-aft direction of the field of view of the endoscope (reciprocating) is performed by axial movement of the treatment tool, vertical and horizontal movement thereof is performed by tilting of the treatment tool. That is, the field of view is moved by tilting the whole of the endoscopic surgery device including the outer tube. In this case, since the field of view can be moved by tilting of the outer tube, it is unnecessary to enlarge an incised portion in order to perform treatment and movement of the field of view, thereby enabling minimally invasive surgery to be performed. Further, when inserted into the outer tube, the treatment tool is engaged with the treatment tool holding section and is held by predetermined frictional force (second frictional force), so that it is possible to attach the treatment tool to the outer tube in a detachable manner. As a result, it is possible to easily perform cleaning, maintenance, management, and the like of the treatment tool. In addition, it is possible to easily perform attaching of the treatment tool to the mobile object and detaching thereof from the mobile object because the attaching and detaching are automatically performed by operation of inserting the treatment tool into the outer tube and removing it from the outer tube.

A thirty second aspect is a mode of the outer tube of the thirty first aspects above, in which the treatment tool holding section includes a second mobile object which is engaged with the mobile object by a third frictional force smaller than the first frictional force and is provided so as to be movable with respect to the mobile object in the direction parallel to the axis of the outer tube body, and when the insertion section of treatment tool is inserted into the outer tube body, the insertion section of the treatment tool and the second mobile object are engaged with each other by the second frictional force.

According to the thirty second aspect, the treatment tool holding section is provided with the second mobile object that holds the treatment tool. The second mobile object is provided in the mobile object so as to be movable by engaging with the mobile object by frictional force (the third frictional force) smaller than frictional force (the first frictional force) between the outer tube body and the mobile object. When inserted into the outer tube, the treatment tool is engaged with the second mobile object by the second frictional force to be held by the second mobile object. Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool, whereby it is possible to provide a stable image to further facilitate treatment.

A thirty third aspect is a mode of the outer tube of the thirty first aspects above, in which the treatment tool holding section includes: a cylindrical second mobile object which is engaged with the mobile object by a third frictional force smaller than the first frictional force, is provided so as to be movable in a direction parallel to the axis of the outer tube body with respect to the mobile object, and into which the insertion section of the treatment tool is inserted; and an elastic body which is arranged in the second mobile object and engages with the insertion section of the treatment tool inserted into the second mobile object by the second frictional force to press and hold the insertion section of the treatment tool.

According to the thirty third aspect, the treatment tool holding section is provided with the second mobile object that holds the treatment tool. The second mobile object is formed into a cylindrical shape, and is provided in the mobile object so as to be movable by engaging with the mobile object by frictional force (the third frictional force) smaller than frictional force (the first frictional force) between the outer tube body and the mobile object. In addition, the second mobile object is provided inside with the elastic body, and when inserted into the outer tube, the treatment tool is pressed and held to the second mobile object by the elastic body (engaged by the second frictional force and is pressed and held). Accordingly, it is possible to prevent the mobile object from being displaced (amplitude) with respect to the outer tube body when the treatment tool is slightly axially displaced (when reciprocated at a small amplitude). As a result, it is possible to effectively prevent a screen from shaking due to slight reciprocating movement of the treatment tool, whereby it is possible to provide a stable image to further facilitate treatment.

A thirty fourth aspect is a mode of the outer tube of any one of the thirty first to thirty third aspects above, which further includes a movement regulating member which regulates movement of the mobile object.

According to the thirty fourth, it is possible to arbitrarily regulate movement of the mobile object. As a result, it is possible to arbitrarily stop axial movement of the treatment tool and the endoscope to improve operability of the treatment tool and the endoscope. In addition, in a configuration in which the treatment tool and the endoscope are detachable, it is possible to easily attach and detach the treatment tool and the endoscope.

A thirty fifth aspect is a mode of the outer tube of the thirty fourth aspect above, in which the movement regulating member regulates movement of the mobile object when the mobile object moves in the outer tube body in a direction to a proximal end to reach a predetermined movement regulation position, and in a state where movement of the mobile object is regulated, when the insertion section of the treatment tool is inserted by a predetermined amount, the movement regulating member releases regulation of movement of the mobile object.

According to the thirty fifth aspect, movement of the mobile object is regulated when the mobile object moves in the outer tube body in the direction to the proximal end to reach the predetermined movement regulation position. In addition, in a state where movement of the mobile object is regulated, when the insertion section of the treatment tool is inserted by the predetermined amount, regulation of movement of the mobile object is released. The mobile object moves in conjunction with reciprocation of the treatment tool. When operation (operation of moving the treatment tool in the direction to the proximal end of the outer tube) of removing the treatment tool from the outer tube is performed, the mobile object moves in the direction to the proximal end to be locked at the predetermined position (movement regulation position). Insertion of the treatment tool is performed in a state where the mobile object is locked in the outer tube body, and when the treatment tool is inserted by the predetermined amount, the lock of the mobile object is released. As a result, it is possible to automatically set a relative positional relationship between the endoscope and the treatment tool as well as to further improve operability of the endoscope and the treatment tool.

A thirty sixth aspect is a mode of the outer tube of the thirty fourth aspect above, in which the movement regulating member includes: a mobile object lock pin provided on a moving path of the mobile object in a retractable manner; a mobile object lock pin urging member which urges the mobile object lock pin in a projecting direction; and a mobile object lock release member which retracts the mobile object lock pin from the moving path of the mobile object against urging force of the mobile object lock pin urging member.

According to the thirty sixth aspect, the movement regulating member includes: the mobile object lock pin provided on a moving path of the mobile object in a retractable manner; the mobile object lock pin urging member which urges the mobile object lock pin in the projecting direction;

and the mobile object lock release member which retracts the mobile object lock pin from the moving path of the mobile object against urging force of the mobile object lock pin urging member. The mobile object lock pin is configured to project in the moving path of the mobile object to allow the mobile object lock pin to engage with the mobile object moving in the outer tube body of the outer tube so that movement of the mobile object is regulated. In a case of releasing regulation of movement of the mobile object, the mobile object lock pin is configured to retract from the moving path of the mobile object against urging force of the mobile object lock pin urging member.

A thirty seventh aspect is a mode of the outer tube of the thirty sixth aspect above, in which, when the insertion section of the treatment tool is inserted into the outer tube body by a predetermined amount, the mobile object lock releasing member is engaged with the insertion section of the treatment tool and retracts the mobile object lock pin from the moving path of the mobile object against the urging force of the mobile object lock pin urging member.

According to the thirty seventh, when inserted into the outer tube body by the predetermined amount, the insertion section of the treatment tool is engaged with the mobile object lock release member to retract the mobile object lock pin from the moving path of the mobile object against urging force of the mobile object lock pin urging member. As a result, when the treatment tool is inserted by the predetermined amount, a relative positional relationship between the endoscope and the treatment tool can be automatically set.

A thirty eighth aspect is a mode of the outer tube of any one of the thirty first to thirty seventh aspects above, in which the endoscope holding section holds the insertion section of the endoscope in a detachable manner.

According to the thirty eighth aspect, it is possible to attach the endoscope to the outer tube in a detachable manner. As a result, it is possible to easily perform cleaning, maintenance, management, and the like of the endoscope.

A thirty ninth aspect is a mode of the outer tube of the thirty eighth aspect above, which further includes: an endoscope lock pin provided in a retractable manner in either one of the insertion section of the endoscope and the endoscope holding section; a recessed portion provided in the other one thereof; and an endoscope lock pin urging member which urges the endoscope lock pin in a projecting direction, wherein, when the insertion section of the endoscope is inserted into the outer tube, the endoscope lock pin is fitted into the recessed portion to hold the insertion section of the endoscope in the endoscope holding section.

According to the thirty ninth aspect, the endoscope lock pin is provided in either one of the insertion section of the endoscope and the endoscope holding section, and the recessed portion is provided in the other one thereof, and when the insertion section of the endoscope is inserted into the outer tube, the endoscope lock pin is fitted into the recessed portion to hold the insertion section of the endoscope in the endoscope holding section in a detachable manner. As a result, it is possible to easily attach the endoscope in a predetermined position with respect to the mobile object.

A fortieth aspect is a mode of the outer tube of the thirty eighth aspect above, in which the endoscope holding section is capable of adjusting a holding position of the insertion section of the endoscope with respect to the mobile object.

According to the fortieth aspect, it is possible to adjust a holding position of the endoscope with respect to the mobile object. That is, it is possible to adjust a relative positional relationship between the treatment tool and the endoscope.

As a result, it is possible to adjust a field of view (imaging region) of the endoscope as well as to further improve operability of the endoscope.

According to the present invention, an object of the present invention is to provide an endoscopic surgery device and an outer tube, capable of easily obtaining an image desired by an operator to facilitate treatment as well as of performing minimally invasive surgery.

BRIEF DESCRIPTION OF THE DRAWINGS

FIG. 13 is an explanatory diagram of operation of a lock mechanism for locking an endoscope.

FIG. 34 is an explanatory diagram of operation of an outer tube (when a slider is locked).

DETAILED DESCRIPTION OF EXEMPLARY EMBODIMENTS

Referring to accompanying drawings, preferable embodiments of the present invention will be described in detail.

First Embodiment

{Configuration}

Figure 1:
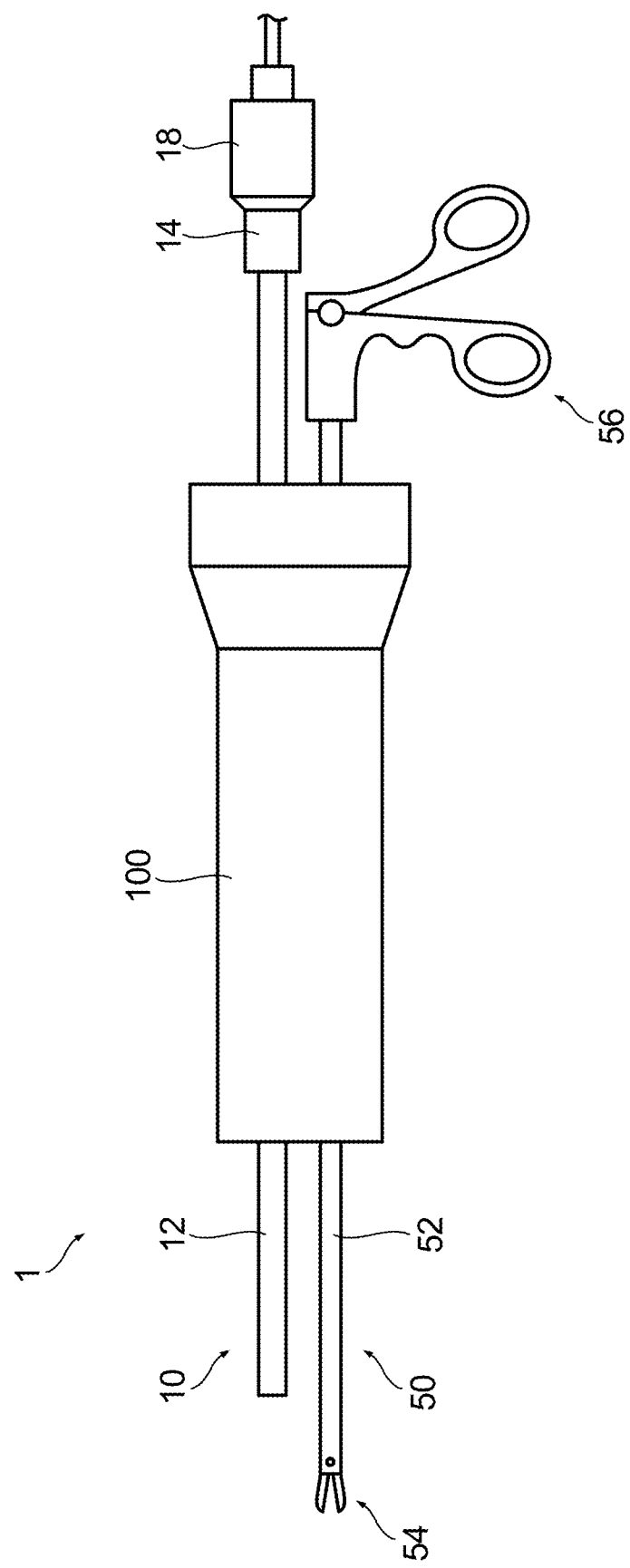
FIG. 1 is a schematic configuration diagram showing a first embodiment of an endoscopic surgery device.

FIG. 1 is a schematic configuration diagram of a first embodiment of the endoscopic surgery device in accordance with the present invention.

As shown in FIG. 1, an endoscopic surgery device 1 of the first embodiment includes: an endoscope 10 that is to be inserted into a body cavity of a patient to observe inside the body cavity; a treatment tool 50 that is to be inserted into the body cavity of the patient to perform required treatment; and an outer tube (trocar) 100 that guides the endoscope 10 and the treatment tool 50 into the body cavity of the patient.

(Endoscope)

Figure 2:
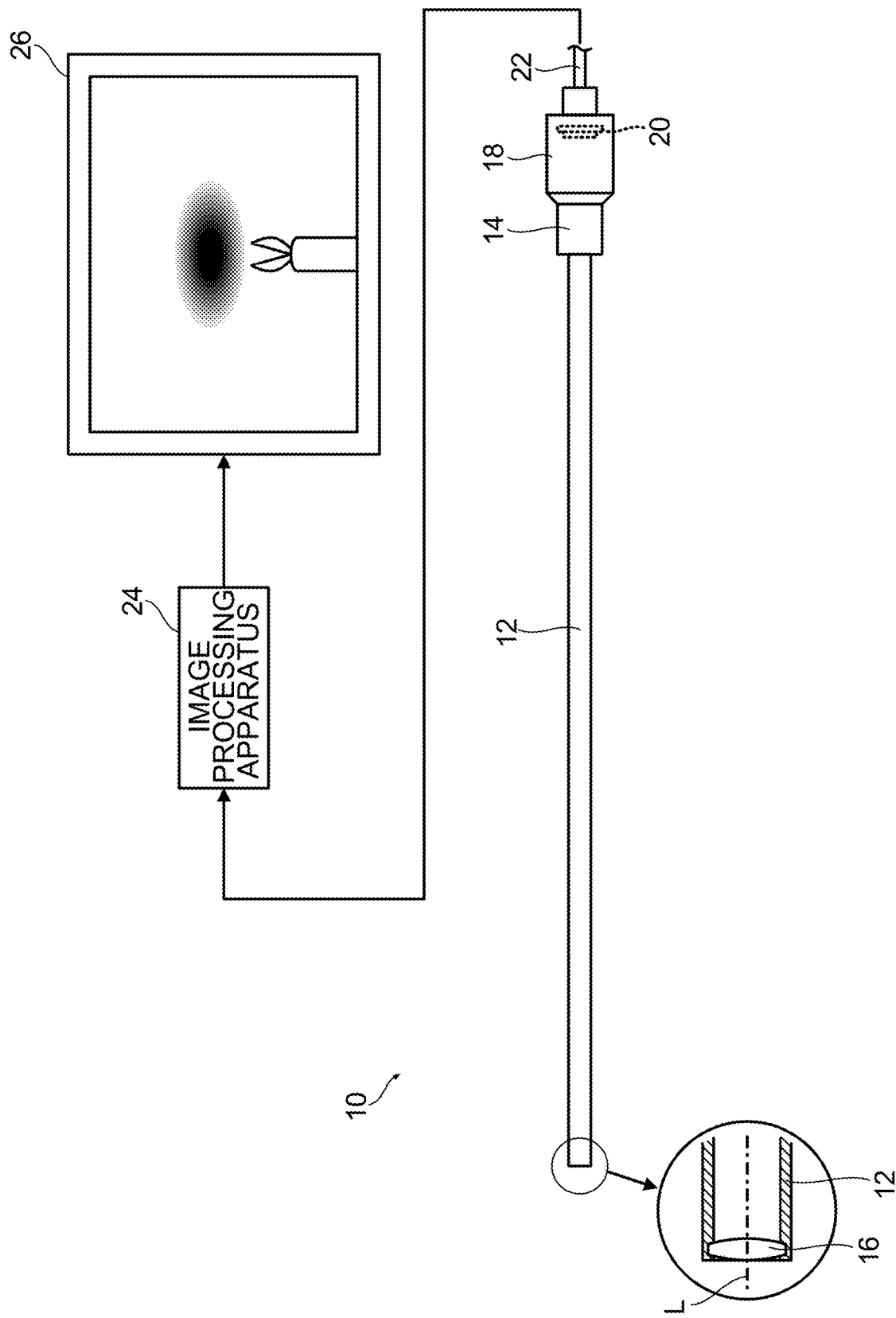
FIG. 2 is a schematic configuration diagram showing an example of an endoscope.

FIG. 2 is a schematic configuration diagram showing an example of an endoscope.

The endoscope 10 is, for example, composed of a rigid endoscope of a direct viewing type, such as a laparoscope. The endoscope 10 includes a linear insertion section 12 that is to be inserted into a body cavity of a patient, and an eyepiece part 14 that is provided at a proximal end part of the insertion section 12.

The insertion section 12 is provided at its end with an objective lens 16, and the eyepiece part 14 is provided with an ocular lens (not shown). The insertion section 12 is provided inside with a plurality of relay lenses (not shown). The objective lens forms an image and the image is observed with the eyepiece lens through the relay lenses.

The objective lens 16 has an optical axis L arranged parallel to an axis of the insertion section 12 (the same applies to the eyepiece lens and the relay lenses). Thus, in the eyepiece part 14, an object facing to a distal end surface of the insertion section 12 is observed.

The eyepiece part 14 is provided with a TV camera 18 that takes a part of or all of observation images of the endoscope 10. The TV camera 18 includes a built-in imaging element (such as a CCD, and a CMOS) 20 serving as imaging means. Accordingly, it is possible to take a part of or all of images observed with the eyepiece part 14 of the endoscope 10 (observation images of the endoscope 10) by using the imaging element.

The TV camera 18 is connected to an image processing apparatus 24 through a flexible cable 22. The image processing apparatus 24 captures a signal outputted from the imaging element 20 and applies various kinds of processing to the captured signal to create a video signal that can be outputted to a display.

The image processing apparatus 24 is connected to a display (such as a liquid crystal monitor) 26. The image processing apparatus 24 creates a video signal that is outputted to the display 26 and the video signal is displayed on a display surface (screen) of the display 26 as an endoscope photographing image.

The endoscope 10 of the present example is provided with no illumination means. Illumination is performed by using separated means such as a needle light. Eliminating illumination means built in the endoscope enables a diameter of an insertion section of an endoscope to be reduced. As a result, a diameter of an outer tube also can be reduced, so that it is possible to reduce a burden to a patient (minimally invasive surgery is possible).

Upon practicing the present invention, an endoscope is not limited to a relay lens method, but an endoscope provided with imaging means at a portion of a distal end of the insertion section may be available.

Figure 3:
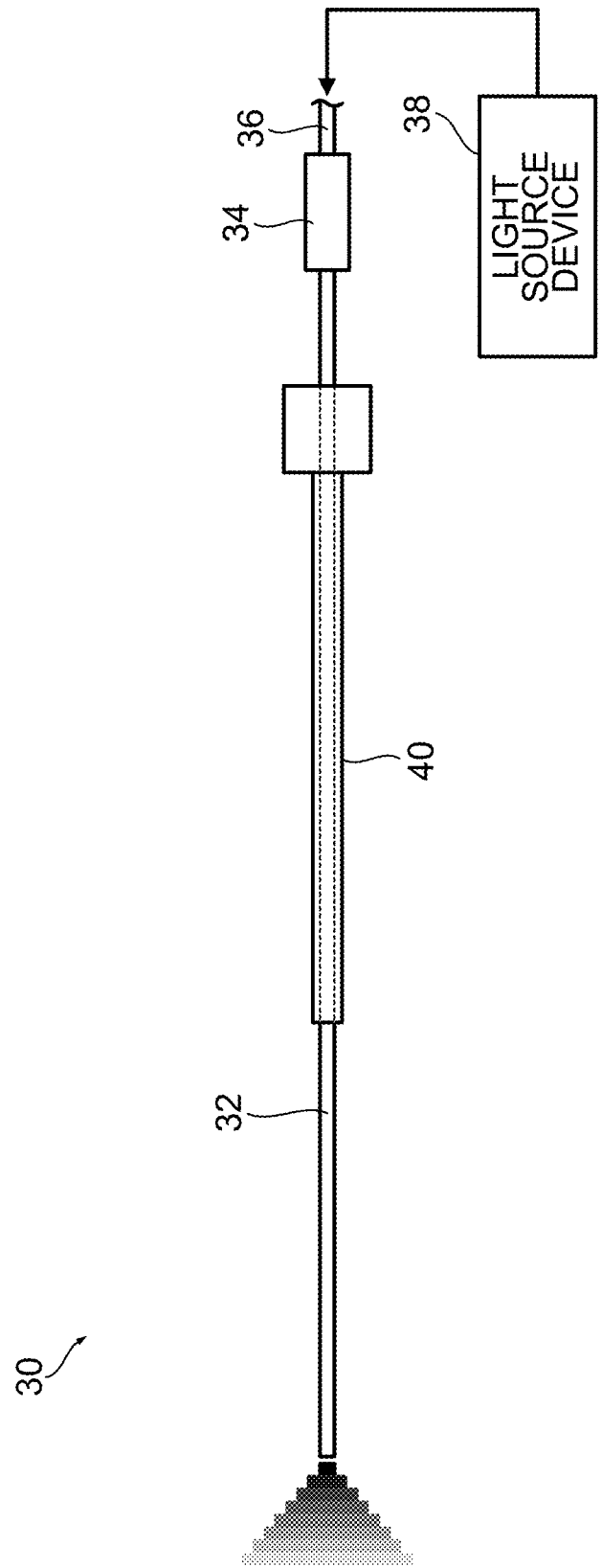
FIG. 3 is a schematic configuration diagram showing an example of a needle light.

FIG. 3 is a schematic configuration diagram showing an example of a needle light.

The needle light 30 is inserted into a body cavity of a patient to irradiate the inside of the body cavity with illumination light.

The needle light 30 is provided with a linear insertion section 32. The insertion section is provided at its distal end with an illumination window (not shown) through which illumination light is axially emitted. In the inside of the insertion section 32, there is housed an optical fiber bundle through which the illumination light emitted through the illumination window is transmitted.

The needle light 30 is provided at its proximal end part with a connection part 34. The connection part 34 is connected to a light source device 38 through a flexible cable 36. Illumination light to be emitted through the illumination window is supplied from the light source device.

The needle light 30 is inserted into a body cavity through a trocar 40 for a needle light, for example.

(Treatment Tool)

Figure 4:
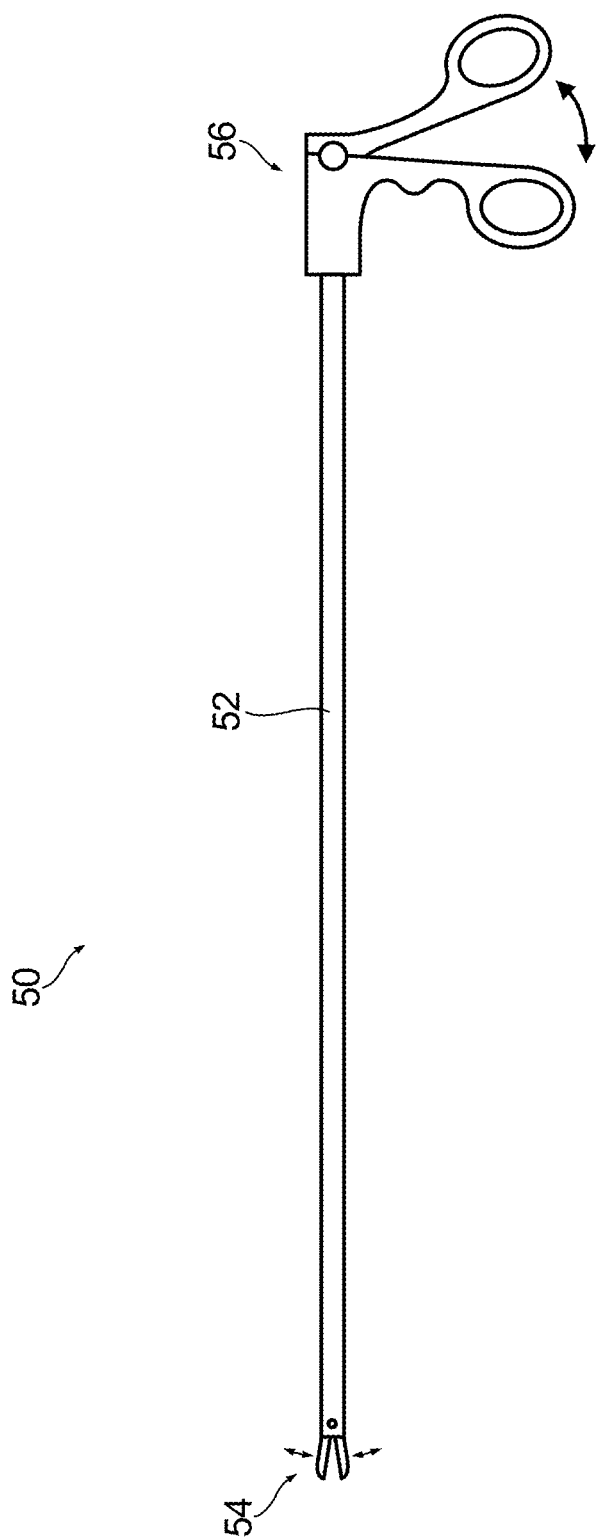
FIG. 4 is a schematic configuration diagram showing an example of a treatment tool.

FIG. 4 is a schematic configuration diagram showing an example of a treatment tool.

The treatment tool 50 includes: a linear insertion section 52 to be inserted into a body cavity; a treatment section 54 provided at a distal end part of the insertion section 52; and a handle section 56 provided at a proximal end part of the insertion section 52. In the present example, the treatment section 54 is composed of a scissors structure, so that opening-closing operation of the handle section 56 opens and closes the treatment section 54.

The treatment tool is not limited to the above. Forceps, a laser probe, a suture instrument, an electric knife, a needle holder, and an ultrasound aspirator, are available as the treatment tool.

(Outer Tube)

An outer tube 100 is penetrated through a body cavity wall of a patient to guide the endoscope 10 and the treatment tool 50 into the body cavity of the patient.

Figure 5:
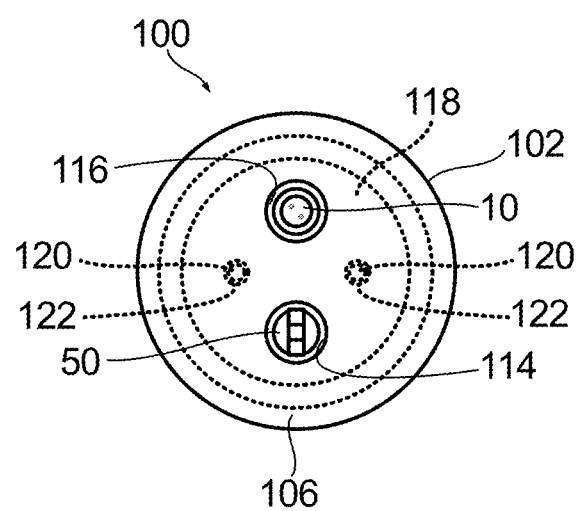
FIG. 5 is a front view of an outer tube.
Figure 6:
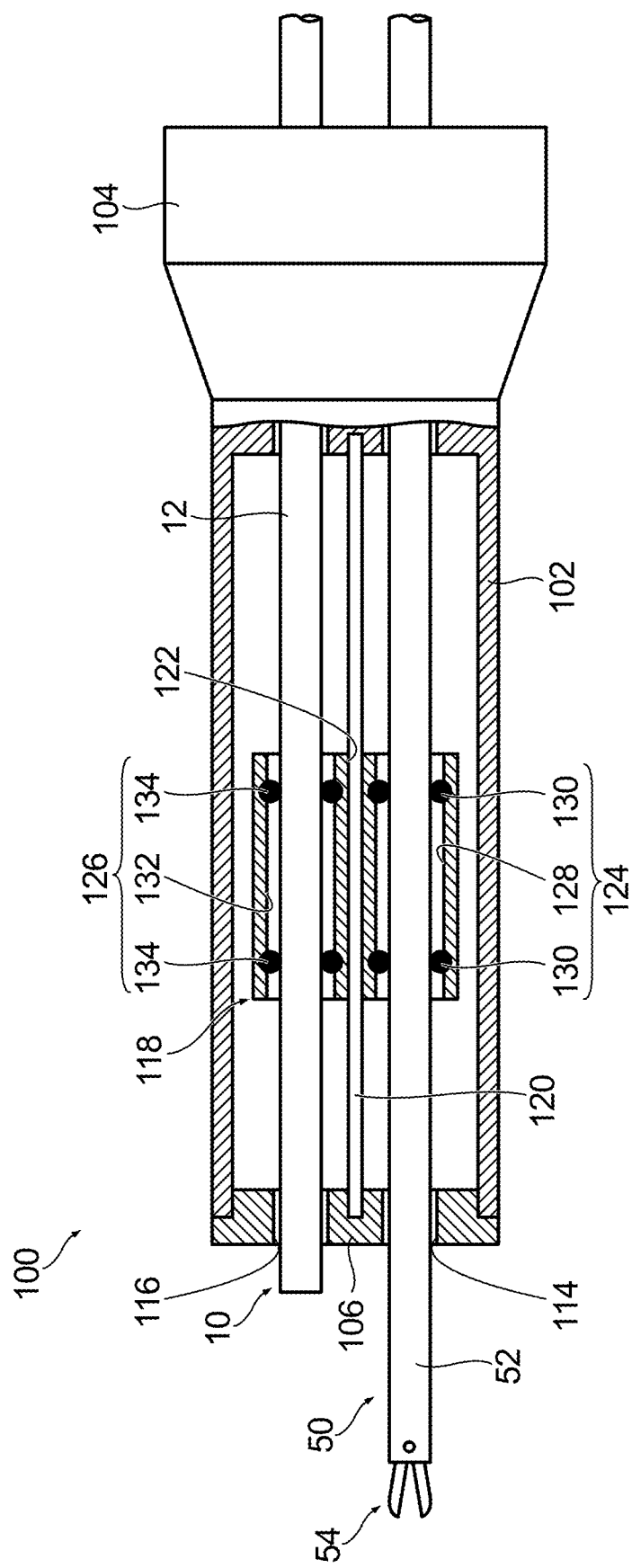
FIG. 6 is a sectional side view of an outer tube.

FIG. 5 is a front view of an outer tube. FIG. 6 is a sectional side view of an outer tube, and FIG. 7 is a rear view of an outer tube.

The outer tube 100 is provided with an outer tube body 102 that is formed into a cylindrical shape. The outer tube body 102 is provided at its rear end (proximal end) with a rear end cap 104. The rear end cap 104 closes a rear end opening part of the outer tube body 102. The outer tube body 102 is provided at its distal end with a distal end cap 106. The distal end cap closes a distal end opening part of the outer tube body 102.

Figure 7:
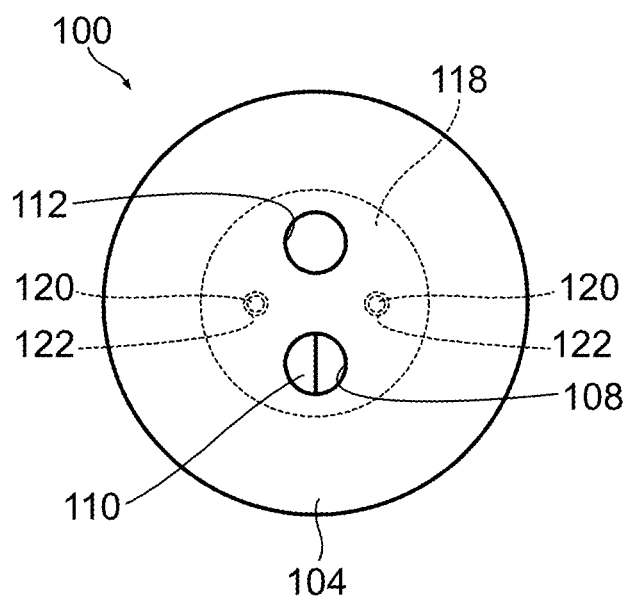
FIG. 7 is a rear view of an outer tube.

As shown in FIG. 7, the rear end cap 104 is provided with a treatment tool insertion port 108 through which the insertion section 52 of the treatment tool 50 is inserted into the outer tube body. The treatment tool insertion port 108 has an inner diameter corresponding to an outer diameter of the insertion section 52 of the treatment tool 50 to be used. The treatment tool insertion port 108 is provided with a valve 110. The valve 110 is composed of a rubber plate with a slit, for example. When the treatment tool 50 is not inserted, the valve 110 seals the treatment tool insertion port 108.

In addition, the rear end cap 104 is provided with an endoscope insertion port 112 through which the insertion section 12 of the endoscope 10 is inserted into the outer tube body. The endoscope insertion port 112 has an inner diameter corresponding to an outer diameter of the insertion section 12 of the endoscope 10 to be used.

As shown in FIG. 5, the distal end cap 106 is provided with a treatment tool feed port 114 through which the insertion section 52 of the treatment tool 50 inserted into the outer tube body 102 is fed. The treatment tool feed port 114 has an inner diameter corresponding to an outer diameter of the insertion section 52 of the treatment tool 50 to be used. The treatment tool insertion port 108 and the treatment tool feed port 114 are coaxially arranged so as to be parallel to an axis of the outer tube body 102. Accordingly, as shown in FIG. 6, the treatment tool 50 inserted through the treatment tool insertion port 108 is fed through the treatment tool feed port 114. At that time, the treatment tool 50 is fed parallel to the axis of the outer tube body 102.

In addition, the distal end cap 106 is provided with an endoscope feed port 116 through which the insertion section 12 of the endoscope 10 inserted into the outer tube body through the endoscope insertion port 112 is fed. The endoscope feed port 116 has an inner diameter corresponding to an outer diameter of the insertion section 12 of the endoscope 10 to be used. The endoscope insertion port 112 and the endoscope feed port 116 are coaxially arranged so as to be parallel to an axis of the outer tube body 102. Accordingly, as shown in FIG. 6, the endoscope 10 inserted through the endoscope insertion port 112 is fed through the endoscope feed port 116. At that time, the endoscope 10 is fed parallel to the axis of the outer tube body 102. (as well as parallel to the insertion section 52 of the treatment tool 50).

As shown in FIG. 6, the outer tube body 102 is provided inside with a slider 118 serving as a mobile object movable in a direction parallel to the axis of the outer tube body 102.

The slider 118 is formed into a columnar shape that can be housed in the outer tube body. The slider 118 is provided so as to be movable in the outer tube body in a direction parallel to the axis of the outer tube body 102 by being guided with a pair of guide shafts 120.

Each of the guide shafts 120 is formed into a rod-like shape, and is arranged in parallel with each other in the outer tube body (refer to FIG. 5). In addition, both ends of each of the guide shafts 120 are supported so that each of the guide shafts is arranged parallel to the axis of the outer tube body 102.

The slider 118 is provided with a pair of guide holes 122 through which the pair of guide shafts 120 can be inserted. The pair of guide holes 122 are arranged at the same interval as the arrangement interval of the pair of guide shafts 120 and each of the guide holes is arranged so as to be parallel to the axis of the outer tube body 102. The guide shafts 120 are inserted through the guide holes 122 and the slider 118 is guided by the guide shafts 120.

The slider 118 includes a treatment tool holding section 124 that holds the insertion section 52 of the treatment tool 50 inserted into the outer tube body 102, and an endoscope holding section 126 that holds the insertion section 12 of the endoscope 10 inserted into the outer tube body 102.

The treatment tool holding section 124 is composed of a treatment tool holding hole 128 through which the insertion section 52 of the treatment tool 50 is inserted, and a pair of O-rings (ring-shaped elastic body) 130 arranged in the treatment tool holding hole.

The treatment tool holding hole 128 penetrates the slider 118 to form a through-hole. The treatment tool holding hole 128 is formed parallel to the axis of the outer tube body 102, and is arranged coaxially with the treatment tool insertion port 108 and the treatment tool feed port 114.

The pair of O-rings 130 is attached to two places, front and rear, inside the treatment tool holding hole 128. Each of the O-rings 130 has an inner diameter slightly smaller than an outer diameter of the insertion section 52 of the treatment tool 50.

The insertion section 52 of the treatment tool 50 inserted into the outer tube body through the treatment tool insertion port 108 is fed from the treatment tool feed port 114 through the treatment tool holding hole 128. The treatment tool 50 passes through each of the O-rings 130 when passing through the treatment tool holding hole 128. As described above, each of the O-rings 130 has the inner diameter slightly smaller than the outer diameter of the insertion section 52 of the treatment tool 50. Thus, when inserted into the treatment tool holding hole 128, the treatment tool 50 is pressed by the O-rings 130 to be held in the treatment tool holding hole.

Since the treatment tool 50 is pressed and held by using the O-rings 130 in that case above, it is possible to arbitrarily adjust a holding position of the treatment tool 50 by the treatment tool holding hole 128 (it is possible to arbitrarily adjust a holding position with respect to the slider 118).

In addition, when the treatment tool 50 is pressed and held by using the O-rings 130, frictional force (second frictional force F2) between each of the O-rings 130 and the treatment tool 50 is set so as to be larger than frictional force (corresponding to frictional force between the outer tube body 102 and slider 118, indicated as first frictional force F1) between the guide shafts 120 and the guide holes 122. As a result, the treatment tool 50 and the slider 118 can be integrally moved.

The endoscope holding section 126 is composed of an endoscope holding hole 132 through which the insertion section 12 of the endoscope 10 is inserted, and a pair of O-rings (ring-shaped elastic body) 134 arranged in the endoscope holding hole.

The endoscope holding hole 132 penetrates the slider 118 to form a through-hole. The endoscope holding hole 132 is formed parallel to the axis of the outer tube body 102, and is arranged coaxially with the endoscope insertion port 112 and the endoscope feed port 116.

The pair of O-rings 134 is attached to two places, front and rear, inside the endoscope holding hole 132. Each of the O-rings 134 has an inner diameter slightly smaller than an outer diameter of the insertion section 12 of the endoscope 10.

The insertion section 12 of the endoscope 10 inserted into the outer tube body through the endoscope insertion port 112 is fed from the endoscope feed port 116 through the endoscope holding hole 132. The endoscope 10 is allowed to pass through each of the O-rings 134 when passing through the endoscope holding hole 132. As described above, each of the O-rings 134 has the inner diameter slightly smaller than the outer diameter of the insertion section 12 of the endoscope 10. Thus, when inserted into the endoscope holding hole 132, the endoscope 10 is pressed by each of the O-rings 134 to be pressed and held in the endoscope holding hole.

Since the endoscope 10 is pressed and held by using each of the O-rings 134 in that case above, it is possible to arbitrarily adjust a holding position of the endoscope 10 by the endoscope holding hole 132 (it is possible to arbitrarily adjust a holding position with respect to the slider 118).

In addition, when the endoscope 10 is pressed and held by using each of the O-rings 134, frictional force (corresponding to frictional force between the slider 118 and the endoscope 10) between each of the O-rings 134 and the endoscope 10 is set so as to be larger than frictional force (corresponding to frictional force between the outer tube body 102 and slider 118, indicated as first frictional force F1) between the guide shafts 120 and the guide holes 122. As a result, the slider 118 and the endoscope 10 can be integrally moved.

(Operation)

Next, operation of the endoscopic surgery device 1 of the first embodiment configured as above will be described.

In the endoscopic surgery device 1 of the first embodiment, the endoscope 10 and the treatment tool 50 are inserted into a body cavity of a patient through one outer tube 100. The endoscope 10 and the treatment tool 50 inserted into the body cavity through the outer tube 100 are moved in conjunction with each other. Hereinafter, interlock operation between the endoscope 10 the treatment tool 50 will be described.

First, the insertion section 12 of the endoscope 10 and the insertion section 52 of the treatment tool 50 are inserted into the outer tube 100.

The endoscope 10 is inserted from the endoscope insertion port 112. The insertion section 12 of the endoscope 10 inserted through the endoscope insertion port 112 passes through inside the outer tube 100 to be fed from the endoscope feed port 116. At that time, the insertion section 12 of the endoscope 10 passes through the endoscope holding hole 132 formed in the slider 118 arranged in the outer tube body to be fed from the endoscope feed port 116. The endoscope holding hole 132 is provided with the O-rings 134, so that the insertion section 12 of the endoscope 10 inserted into the endoscope holding hole 132 is pressed by the O-rings 134 and is held in the endoscope holding hole.

On the other hand, the treatment tool 50 is inserted from the treatment tool insertion port 108. The insertion section 52 of the treatment tool 50 inserted through the treatment tool insertion port 108 passes through inside the outer tube 100 to be fed from the treatment tool feed port 114. At that time, the insertion section 52 of the treatment tool 50 passes through the treatment tool holding hole 128 formed in the slider 118 arranged in the outer tube body to be fed from the treatment tool feed port 114. The treatment tool holding hole 128 is provided with the O-rings 130, so that the insertion section 52 of the treatment tool 50 inserted into the treatment tool holding hole 128 are pressed by the O-rings 130 and are held in the treatment tool holding hole 128.

Figure 8:
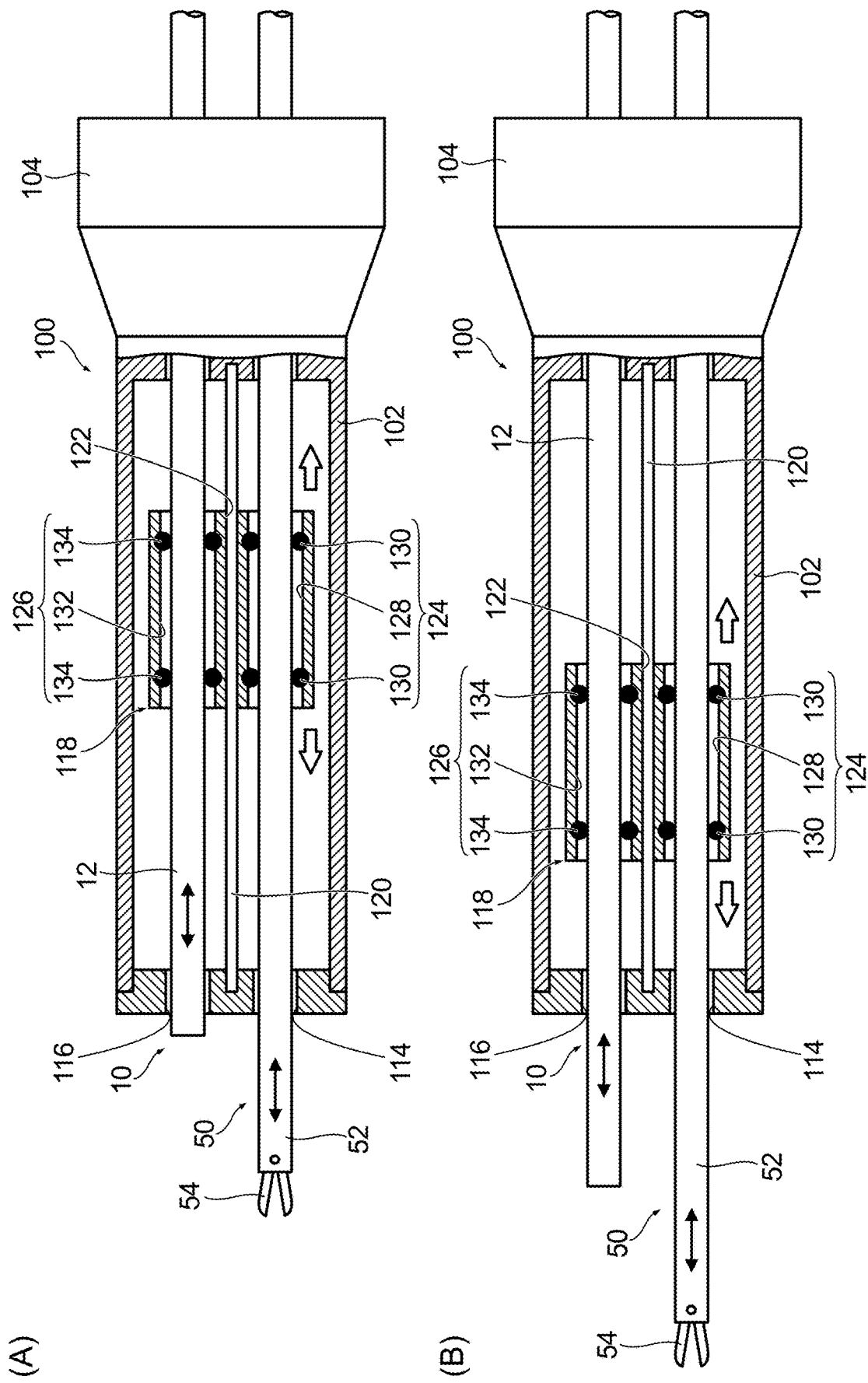
FIG. 8 shows a usage form of an endoscopic surgery device of the first embodiment.

FIG. 8 shows a usage form of an endoscopic surgery device of the first embodiment.

As shown in FIG. 8, the insertion section 12 of the endoscope 10 and the insertion section 52 of the treatment tool 50 which are inserted into the outer tube 100 are held parallel to each other as well as held parallel to the axis of the outer tube 100.

Since the insertion section 52 of the treatment tool 50 is pressed and held in the treatment tool holding hole 128 provided in the slider 118 in the outer tube body of the outer tube 100, when the insertion section 52 of the treatment tool 50 is axially moved, the slider 118 is also axially moved in conjunction with the insertion section 52.

On the other hand, since the insertion section 12 of the endoscope 10 is pressed and held in the endoscope holding hole 132 provided in the slider 118 in the outer tube body of the outer tube 100, when the slider 118 is moved, the insertion section 12 of the endoscope 10 is also axially moved.

That is, as shown in FIG. 8, when the insertion section 52 of the treatment tool 50 is axially moved, the insertion section 12 of the endoscope 10 is also axially moved in conjunction with the insertion section 52, and vice versa. That is, when the insertion section 12 of the endoscope 10 is axially moved, the insertion section 52 of the treatment tool 50 is also axially moved in conjunction with the insertion section 12.

Accordingly, even in a case where the treatment tool 50 is moved, it is possible to move a field of view (imaging region) of the endoscope 10 in conjunction with movement of the treatment tool 50, so that it is possible to constantly check a video of a portion treated by the treatment tool 50 on a display. In addition, since the field of view of the endoscope 10 is moved by operation of moving the treatment tool 50, the field of view of the endoscope 10 can be directly moved by operator's intention. As a result, an operator can quickly view a desired video and perform prompt treatment. In addition, stress on the operator can be reduced.

While axial movement of the field of view of the endoscope is performed by fore-and-aft axial movement (reciprocating) of the treatment tool 50, vertical and horizontal movement thereof is performed by tilting in vertical and horizontal directions (so-called oscillating operation) of the treatment tool 50.

In addition, adjustment of a position at which the endoscope 10 takes an image of the treatment tool 50 is performed by adjusting a relative positional relationship of the endoscope 10 with respect to the treatment tool 50.

Since the insertion section 52 of the treatment tool 50 is held in the slider 118 by being pressed and held with the O-rings 130 provided in the treatment tool holding hole 128, it is possible to arbitrarily adjust a holding position of the treatment tool 50 with respect to the slider 118. Likewise, since the insertion section 12 of the endoscope 10 is also held in the slider 118 by being pressed and held with the O-rings 134 provided in the endoscope holding hole 132, it is possible to arbitrarily adjust a holding position of the endoscope 10 with respect to the slider 118. Thus, adjustment of the holding position of the insertion section 52 of the treatment tool 50 with respect to the slider 118, or of the holding position of the insertion section 12 of the endoscope 10, enables to adjust a position at which the endoscope 10 takes an image with respect to the treatment tool 50. For example, it is possible to adjust the position so that the distal end of the treatment tool 50 is positioned at the center of the field of view.

As described above, according to the endoscopic surgery device 1 of the first embodiment, it is possible to move the field of view (imaging region) of the endoscope 10 in conjunction with movement of the treatment tool 50. As a result, the field of view of the endoscope 10 can be directly moved by operator's intention, and then the operator can quickly view a desired video.

Since the endoscope 10 and the treatment tool 50 are inserted into a body cavity of a patient through one outer tube 100, it is possible to perform minimally invasive surgery without giving a burden to a patient As described above, according to the endoscopic surgery device 1 of the first embodiment, since the endoscope 10 can be operated by operating the treatment tool 50, an endoscopist becomes unnecessary. As the endoscopist becomes unnecessary, there is no problem in which a hand of the operator and a hand of the endoscopist may interfere with each other on the abdominal wall of a patient. In addition, since significantly increased operating space can be secured, a workability of treatment can be significantly improved.

(Example of Use)

Next, operative procedure using the endoscopic surgery device 1 of the first embodiment configured as above will be described.

Figure 9:
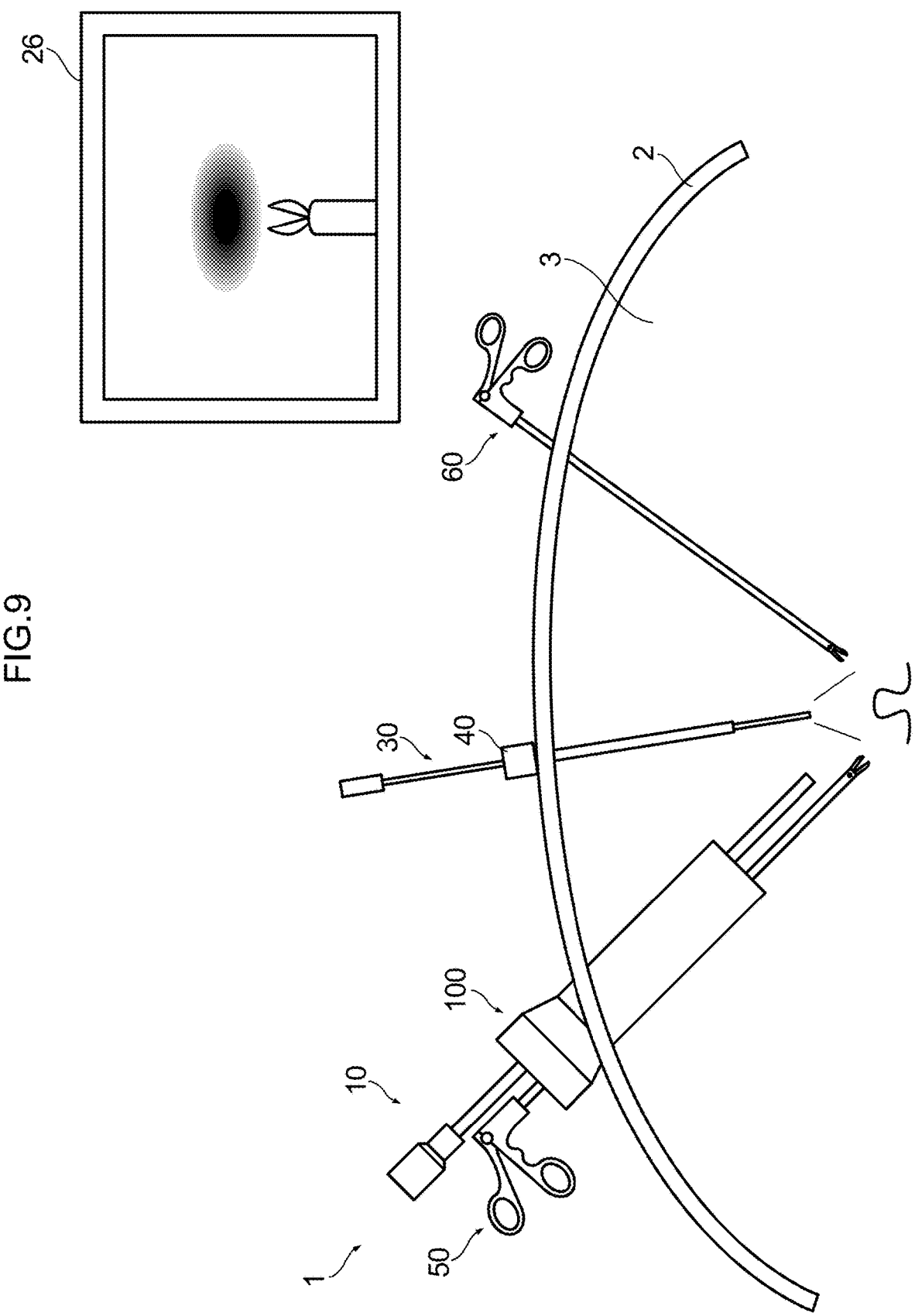
FIG. 9 is a schematic diagram showing an example of an operative procedure using an endoscopic surgery device.

FIG. 9 is a schematic diagram showing an example of an operative procedure using the endoscopic surgery device of the first embodiment.

The present example shows a case where one operator performs treatment.

As described above, the endoscope 10 and the treatment tool 50 are inserted into a body cavity 3 through the outer tube 100 penetrating through a body cavity wall 2 of a patient. The endoscope 10 moves in conjunction with movement of the treatment tool 50. Accordingly, a video of a treatment portion is constantly displayed on a display 26, and a field of view can be moved by moving the treatment tool 50.

Since the endoscope 10 includes no illumination means, a needle light 30 is separately inserted into the body cavity 3 through a trocar 40 for a needle light as the illumination means. The inside of the body cavity 3 is irradiated with illumination light emitted from an end of the needle light 30.

In the present example, one needle light 30 is used, however, a plurality of needle lights 30 may be used if necessary.

As described above, since the endoscope 10 is operated by operation of the treatment tool 50, an endoscopist becomes unnecessary.

Since an endoscopist becomes unnecessary, two treatment tools 50 and 60 can penetrate through the body cavity wall 2 at an angle away from each other so that one operator can perform treatment with both hands with plenty of space. Another treatment tool 60 separately penetrates through the body cavity wall 2 through a trocar to be inserted into the body cavity 3.

As above, by using the endoscopic surgery device 1 of the present embodiment, treatment can be performed by one operator.

At that time, the operator can directly view a desired video by one's own operation, so that the operator can advance the treatment without stress. In addition, since a video of a treatment portion can be constantly viewed, it is possible to easily perform the treatment.

In addition, since the endoscope 10 and the treatment tool 50 are inserted into the body cavity 3 through one outer tube 100, it is possible to perform minimally invasive surgery without giving a burden to a patient.

Second Embodiment (Configuration)

Figure 10:
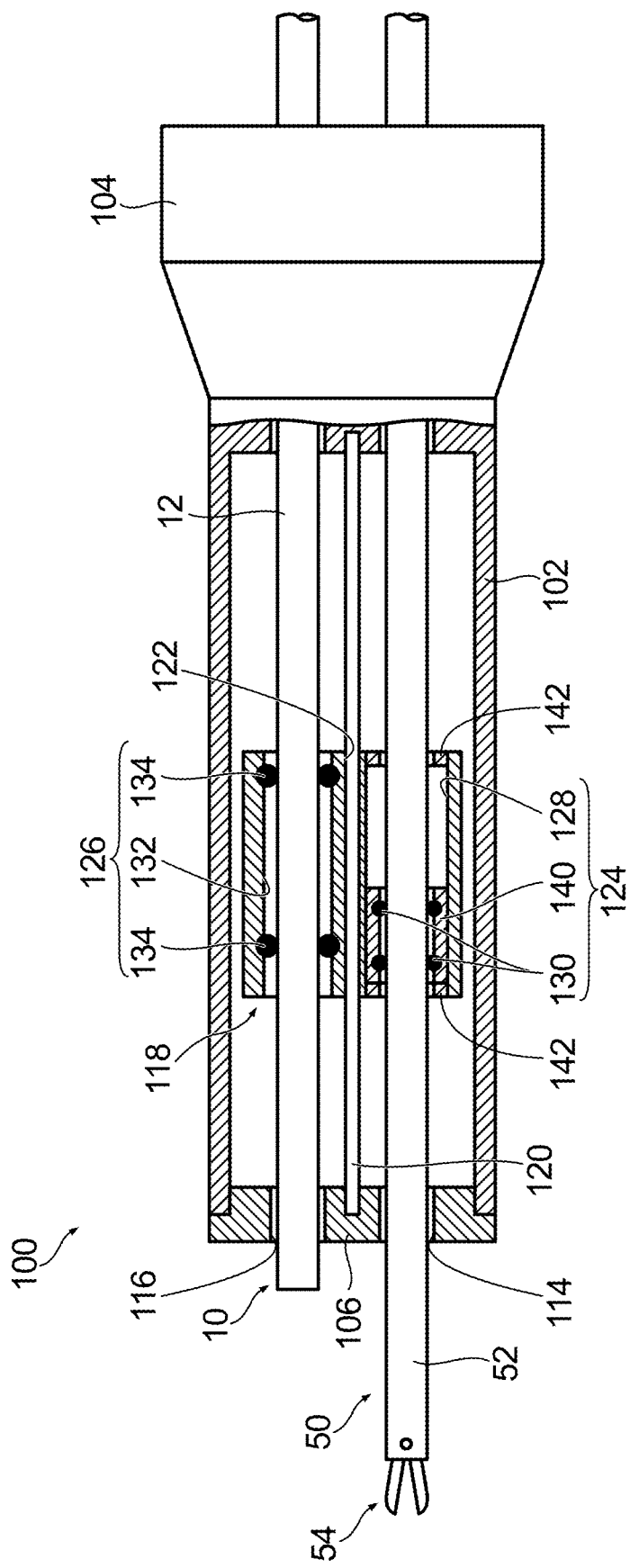
FIG. 10 is a schematic configuration diagram of a main section of a second embodiment of an endoscopic surgery device.

FIG. 10 is a schematic configuration diagram of a main section of a second embodiment of the endoscopic surgery device in accordance with the present invention.

As shown in FIG. 10, the endoscopic surgery device of the second embodiment is different from the endoscopic surgery device of the first embodiment described above in a part of the configuration of the outer tube 100. Thus, hereinafter only the different part will be described.

The outer tube 100 of the endoscopic surgery device of the second embodiment is configured to have a "play" in interlock between the endoscope 10 and the treatment tool 50. Specifically, the treatment tool 50 is provided so as to be movable with respect to the slider 118 with a predetermined stroke.

As shown in FIG. 10, the slider 118 is provided with a treatment tool holding section 124 for holding the treatment tool 50.

The treatment tool holding section 124 includes: a treatment tool holding hole 128 into which the insertion section 52 of the treatment tool 50 is inserted; a slide sleeve 140 arranged in the treatment tool holding hole 128 so as to be axially movable in the treatment tool holding hole, serving as a second mobile object; and a pair of O-rings (ring-shaped elastic body) 130 arranged in a slide sleeve 140.

The treatment tool holding hole 128 penetrates the slider 118 to form a through-hole with a circular cross section. The treatment tool holding hole 128 is formed parallel to the axis of the outer tube body 102, and is arranged coaxially with the treatment tool insertion port 108 and the treatment tool feed port 114.

The treatment tool holding hole 128 is provided at its respective both ends with annular stopper rings 142. The stopper rings 142 are attached coaxially with the treatment tool holding hole 128. The stopper rings 142 prevent the slide sleeve 140 housed in the treatment tool holding hole 128 from coming out of the treatment tool holding hole 128. In addition, the stopper rings 142 regulate a movable range (a range of a "play" described later) of the slide sleeve 140. That is, the slide sleeve 140 is provided so as to be movable between the respective stopper rings 142 provided at both ends of the treatment tool holding hole 128.

The slide sleeve 140 is formed into a cylindrical shape and is housed in the treatment tool holding hole 128. The slide sleeve 140 housed in the treatment tool holding hole 128 is arranged coaxially with the treatment tool holding hole 128, namely, is arranged coaxially with the treatment tool insertion port 108 and the treatment tool feed port 114. Accordingly, when the treatment tool 50 is inserted from the treatment tool insertion port 108 along the axial direction, the treatment tool 50 can be inserted into an inner peripheral portion of the slide sleeve 140.

The pair of O-rings 130 is attached to two places, front and rear, inside the slide sleeve 140. Each of the O-rings 130 has an inner diameter slightly smaller than an outer diameter of the insertion section 52 of the treatment tool 50.

The insertion section 52 of the treatment tool 50 inserted into the outer tube body through the treatment tool insertion port 108 is fed from the treatment tool feed port 114 through the treatment tool holding hole 128. When the treatment tool 50 passes through the treatment tool holding hole 128, the treatment tool 50 passes through the inner peripheral portion of the slide sleeve 140 to be inserted into the O-rings 130 arranged in the inner peripheral portion of the slide sleeve 140. As described above, each of the O-rings 130 has the inner diameter slightly smaller than the outer diameter of the insertion section 52 of the treatment tool 50. Thus, when inserted into the O-rings 130, the treatment tool 50 is pressed by the O-rings 130 to be pressed and held in the inner peripheral portion of the slide sleeve 140 in the treatment tool holding hole.

Since the treatment tool 50 is pressed and held by using the O-rings 130 in that case above, it is possible to arbitrarily adjust a position of the treatment tool 50 engaged to the slide sleeve 140 (it is possible to arbitrarily adjust a holding position with respect to the slider 118).

In the treatment tool holding section 124 configured as above, when the insertion section 52 of the treatment tool 50 is inserted into the slide sleeve 140, the slide sleeve 140 is integrated with the treatment tool 50 so that the slide sleeve 140 moves in conjunction with movement of the treatment tool 50.

If a frictional force between the slide sleeve 140 and the treatment tool holding hole 128 (frictional force between the slide sleeve 140 and the slider 118, indicated as third frictional force F3) is larger than a frictional force between the treatment tool 50 and the O-rings 130 (second frictional force F2), the treatment tool 50 slides between the O-rings 130 so as not to allow the slide sleeve 140 to move with respect to the slider 118. Thus, the frictional force between the slide sleeve 140 and the treatment tool holding hole 128 (third frictional force F3) is set so as to be smaller than the frictional force between the treatment tool 50 and the O-rings 130 (second frictional force F2).

On the other hand, if the frictional force between the slide sleeve 140 and the treatment tool holding hole 128 (third frictional force F3) is larger than frictional force between the guide shaft 120 and the guide hole 122 (corresponding to frictional force between the outer tube body 102 and the slider 118, indicated as first frictional force F1), when the treatment tool 50 is moved, the slider 118 instead of the slide sleeve 140 moves in the outer tube body. Thus, the frictional force (first frictional force F1) between the guide shaft 120 and the guide hole 122 is set so as to be larger than the frictional force between the slide sleeve 140 and the treatment tool holding hole 128 (third frictional force F3).

That is, a relationship among the frictional force between the guide shaft 120 and the guide hole 122 (first frictional force F1), the frictional force between the treatment tool 50 and the O-rings 130 (second frictional force F2), and the frictional force between the slide sleeve 140 and the treatment tool holding hole 128 (third frictional force F3), is set so that the frictional force decreases in the order of the frictional force between the treatment tool 50 and the O-rings 130 (second frictional force F2), the frictional force between the guide shaft 120 and the guide hole 122 (first frictional force F1), and the frictional force between the slide sleeve 140 and the treatment tool holding hole 128 (third frictional force F3) (the second frictional force F2>the first frictional force F1>the third frictional force F3).

Accordingly, it is possible that the slider 118 is not allowed to move when the treatment tool 50 is axially moved as long as the movement is within a predetermined movable range (movement between the pair of stopper rings 142). That is, it is possible to prevent the endoscope 10 from being interlocked, and it is possible to allow the endoscope 10 to have a "play". In addition, allowing the interlock operation between the treatment tool and the endoscope as above to have the "play" can prevent a screen from shaking when the treatment tool is slightly axially displaced (when reciprocated at a small amplitude), for example. As a result, it is possible to provide an easily visible image without shaking.

The frictional force between respective members are adjusted by adjusting a material, surface treatment, and applying a friction member, for example.

(Operation)

Next, operation of the endoscopic surgery device of the second embodiment configured as above will be described.

The endoscopic surgery device of the second embodiment is also used by inserting the endoscope 10 and the treatment tool 50 into the outer tube 100 as with the endoscopic surgery device of the first embodiment above.

First, the insertion section 12 of the endoscope 10 and the insertion section 52 of the treatment tool 50 are inserted into the outer tube 100.

The endoscope 10 is inserted from the endoscope insertion port 112. The insertion section 12 of the endoscope 10 inserted through the endoscope insertion port 112 passes through inside the outer tube 100 to be fed from the endoscope feed port 116. At that time, the insertion section 12 of the endoscope 10 passes through the endoscope holding hole 132 formed in the slider 118 arranged in the outer tube body to be fed from the endoscope feed port 116. The endoscope holding hole 132 is provided with the O-rings 134, so that the insertion section 12 of the endoscope 10 inserted into the endoscope holding hole 132 is pressed by the O-rings 134 and is held in the endoscope holding hole.

On the other hand, the treatment tool 50 is inserted from the treatment tool insertion port 108. The insertion section 52 of the treatment tool 50 inserted through the treatment tool insertion port 108 passes through inside the outer tube 100 to be fed from the treatment tool feed port 114. At that time, the insertion section 52 of the treatment tool 50 passes through the treatment tool holding hole 128 formed in the slider 118 arranged in the outer tube body to be fed from the treatment tool feed port 114. The slide sleeve 140 is housed in the treatment tool holding hole 128, and the insertion section 52 of the treatment tool 50 is inserted into the inner peripheral portion of the slide sleeve 140.

The slide sleeve 140 is provided in its inner peripheral portion with the O-rings 130 that press the insertion section 52 of the treatment tool 50 inserted into the slide sleeve 140 so that the insertion section 52 is pressed and held to the inner peripheral portion of the slide sleeve 140.

Figure 11:
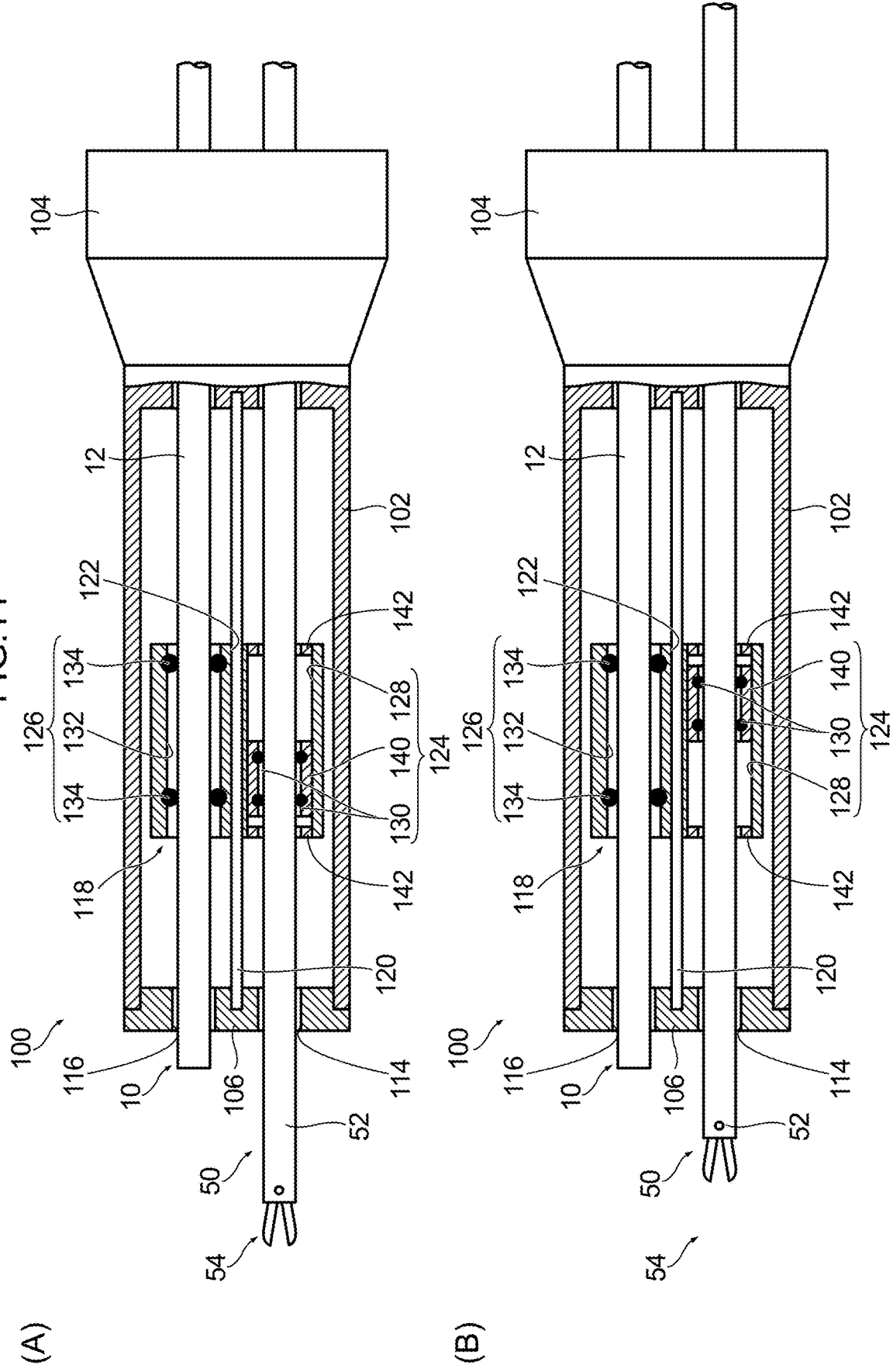
FIG. 11 shows a usage form of an endoscopic surgery device of the second embodiment.

FIG. 11 shows a usage form of the endoscopic surgery device of the second embodiment.

As shown in FIG. 11, the insertion section 12 of the endoscope 10 inserted into the outer tube 100 and the insertion section 52 of the treatment tool 50 are held parallel to each other as well as held parallel to the axis of the outer tube 100.

The insertion section 52 of the treatment tool 50 is pressed and held to the inner peripheral portion of the slide sleeve 140 that is provided so as to be movable with respect to the slider 118 in the axial direction. In addition, a relationship between the frictional force between the slider 118 and the slide sleeve 140 (third frictional force F3), and the frictional force between the guide shaft 120 and the guide hole 122 (corresponding to the frictional force between the outer tube body 102 and slider 118, indicated as the first frictional force F1), is set so that the frictional force between the slider 118 and the slide sleeve 140 (third frictional force F3) is smaller than the frictional force between the guide shaft 120 and the guide hole 122 (first frictional force F1) (the third frictional force F3<the first frictional force F1).

As a result, when the insertion section 52 of the treatment tool 50 is axially moved, within a movable range of the slide sleeve 140, only the treatment tool 50 moves, as shown in (A) and (B) in FIG. 11.

On the other hand, when the insertion section 52 of the treatment tool 50 is moved in the axial direction to exceed the movable range of the slide sleeve 140, the slider 118 and the treatment tool 50 move integrally with each other. As a result, the insertion section 12 of the endoscope 10 moves in conjunction with the treatment tool 50.

For example, when the insertion section 52 of the treatment tool 50 is moved in the distal end to exceed the movable range of the slide sleeve 140 (or moved forward), a distal end of the slide sleeve 140 is brought into contact with the stopper ring 142 provided at the end portion on the distal end side of the treatment tool holding hole 128, and the slider 118 and the treatment tool 50 move integrally with each other in the distal end direction (move forward). As a result, the insertion section 12 of the endoscope 10 moves together with the treatment tool 50 in the distal end direction (moves forward).

On the other hand, when the insertion section 52 of the treatment tool 50 is moved in the rear end direction (proximal end direction) (or moved backward), a rear end of the slide sleeve 140 is brought into contact with the stopper ring 142 provided at the end portion on the rear end side of the treatment tool holding hole 128, and the slider 118 and the treatment tool 50 move integrally with each other in the rear end direction (move backward). As a result, the insertion section 12 of the endoscope 10 moves together with the treatment tool 50 in the rear end direction (moves backward).

As described above, according to the endoscopic surgery device of the second embodiment, it is possible to move the endoscope 10 in conjunction with the treatment tool 50 only when the treatment tool 50 is largely moved. Accordingly, it is possible to prevent movement with a small amplitude, such as a tiny shake, from being transmitted to the endoscope 10, thereby enabling a favorable endoscope image without shaking to be provided.

Third Embodiment (Configuration)

Figure 12:
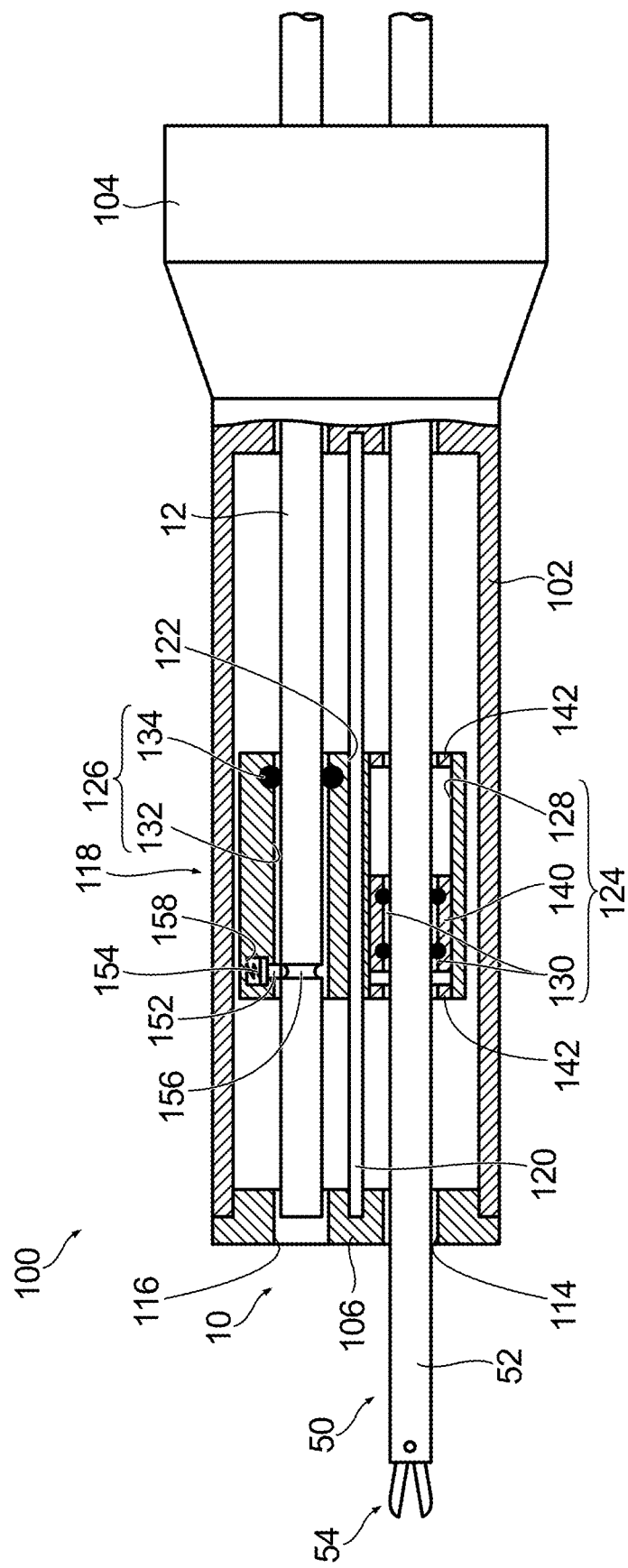
FIG. 12 is a schematic configuration diagram of a main section of a third embodiment of an endoscopic surgery device.

FIG. 12 is a schematic configuration diagram of a main section of a third embodiment of the endoscopic surgery device in accordance with the present invention.

The endoscopic surgery device of the third embodiment is different from the endoscopic surgery device of the second embodiment described above in that the endoscopic surgery device of the third embodiment includes a lock mechanism for locking the endoscope 10 inserted into the outer tube 100 at a predetermined position with respect to the slider 118. Thus, hereinafter only the lock mechanism for the endoscope 10, which is the different portion, will be described.

The lock mechanism for locking the endoscope 10 fixes the insertion section 12 of the endoscope 10 inserted into the outer tube 100 at the predetermined position with respect to the slider 118.

The lock mechanism for locking the endoscope 10 is provided in the endoscope holding hole 132, and is composed of: an endoscope lock pin 152 provided so as to be retractable from an inner peripheral surface of the endoscope holding hole 132 in a radial direction of the endoscope holding hole 132; an endoscope lock pin urging spring (endoscope lock pin urging member) 154 for urging the endoscope lock pin 152 in a projecting direction thereof; and an endoscope lock groove 156 serving as a recessed portion which is formed in an outer peripheral surface of the insertion section 12 of the endoscope 10, and into which the endoscope lock pin 152 can be fitted.

The endoscope lock pin 152 is formed into a columnar shape, and includes a front end portion formed into a hemisphere shape. In the endoscope holding hole 132, there is formed an endoscope lock pin housing hole 158 into which the endoscope lock pin 152 is to be housed. The endoscope lock pin 152 is housed in the endoscope lock pin housing hole 158 so as to be movable back and forth in the radial direction of the endoscope holding hole 132. In addition, the endoscope lock pin 152 is provided at its base end portion with a flange as a stopper.

The endoscope lock pin urging spring 154 is composed of a coil spring, for example, and is housed in the endoscope lock pin housing hole 158. The endoscope lock pin 152 is urged by the endoscope lock pin urging spring 154 in a direction in which the endoscope lock pin 152 projects into the endoscope holding hole 132.

The endoscope lock groove 156 is formed on a peripheral surface of the insertion section 12 of the endoscope 10 so as to serve as a recessed portion into which the endoscope lock pin 152 can be fitted. The endoscope lock groove 156 is provided near the proximal end of the insertion section 12, and is formed into an annular shape. In addition, the endoscope lock groove 156 is formed so as to have a semicircular cross section so that the endoscope lock pin 152 can be fitted thereinto.

(Operation)

Next, operation of the endoscopic surgery device of the third embodiment configured as above will be described.

Since operation other than the lock mechanism for locking the endoscope 10 is the same as the operation of the endoscopic surgery device of the second embodiment described above, hereinafter only operation of the lock mechanism for locking the endoscope 10 will be described.

In the endoscopic surgery device of the third embodiment, since there is provided the lock mechanism for locking the endoscope 10 inserted into the outer tube 100, it is possible to constantly fix the endoscope 10 at a predetermined position with respect to the slider 118.

FIG. 13 is an explanatory diagram of operation of the lock mechanism for locking the endoscope.

When the endoscope 10 is inserted from the endoscope insertion port 112, the insertion section 12 of the endoscope 10 passes through inside the outer tube 100 to be fed from the endoscope feed port 116. At that time, the insertion section 12 of the endoscope 10 passes through the endoscope holding hole 132 formed in the slider 118 arranged in the outer tube body to be fed from the endoscope feed port 116.

The endoscope holding hole 132 is provided with the O-rings 134, and when the insertion section 12 of the endoscope 10 is inserted into the endoscope holding hole 132, the endoscope 10 is pressed by the O-rings 134 and is held in the endoscope holding hole.

In addition, since the endoscope holding hole 132 is provided with the endoscope lock pin 152, when the insertion section 12 of the endoscope 10 is inserted into the endoscope holding hole 132, the endoscope 10 is locked at a predetermined position in the endoscope holding hole with the endoscope lock pin 152. Hereinafter, operation of locking the endoscope 10 by using the endoscope lock pin 152 will be described.

The endoscope lock pin 152 is provided so as to project from the inner peripheral surface of the endoscope holding hole 132 by being urged by the endoscope lock pin urging spring 154. When the insertion section 12 of the endoscope 10 is inserted into the endoscope holding hole 132, the endoscope lock pin 152 is pressed by the peripheral surface of the insertion section 12 of the endoscope 10 to be retracted into the endoscope lock pin housing hole 158.

Since the insertion section 12 of the endoscope 10 is provided at its predetermined position with the endoscope lock groove 156, when the endoscope 10 is pressed forward, the endoscope lock groove 156 reaches a position of the endoscope lock pin 152. When the endoscope lock groove 156 reaches the position of the endoscope lock pin 152, the endoscope lock pin 152 projects from the endoscope lock pin housing hole 158 to fit into the endoscope lock groove 156. As a result, the endoscope 10 is locked.

When the endoscope lock pin 152 fits into the endoscope lock groove 156, a fitting sound occurs. The fitting sound allows an operator to find that the endoscope lock pin 152 fits into the endoscope lock groove 156.

Drawing the locked endoscope from the outer tube 100 by a force more than a certain level can release the lock of the endoscope. That is, drawing the endoscope 10 by a force more than a certain level allows the internal wall surface of the endoscope lock groove 156 to press the endoscope lock pin 152 down to release fitting thereof. As a result, the lock of the endoscope is released.

As above, according to the endoscopic surgery device to the third embodiment, it is possible to constantly lock the endoscope 10 inserted into the outer tube 100 at a predetermined position with respect to the slider 118. As a result, it is possible to save time to set a position of the endoscope 10 so that ease-of-use can be further improved.

In the present example, although the endoscope lock groove 156 is provided at only one place on the peripheral surface of the insertion section 12 of the endoscope 10, the endoscope lock groove 156 may be provided at a plurality of places. Accordingly, it is possible to lock the endoscope 10 at the plurality of places.

In addition, in the present example, although the recessed portion into which the endoscope lock pin 152 is fitted is formed into a groove shape, the recessed portion can be formed into a hole shape.

Further, in the present example, although the endoscope lock pin is provided in the endoscope holding hole side and the recessed portion into which the endoscope lock pin is fitted is provided in the endoscope side, the endoscope lock pin can be provided in the endoscope side and the recessed portion into which the endoscope lock pin is fitted can be provided in the endoscope holding hole side.

Fourth Embodiment (Configuration)

Figure 14:
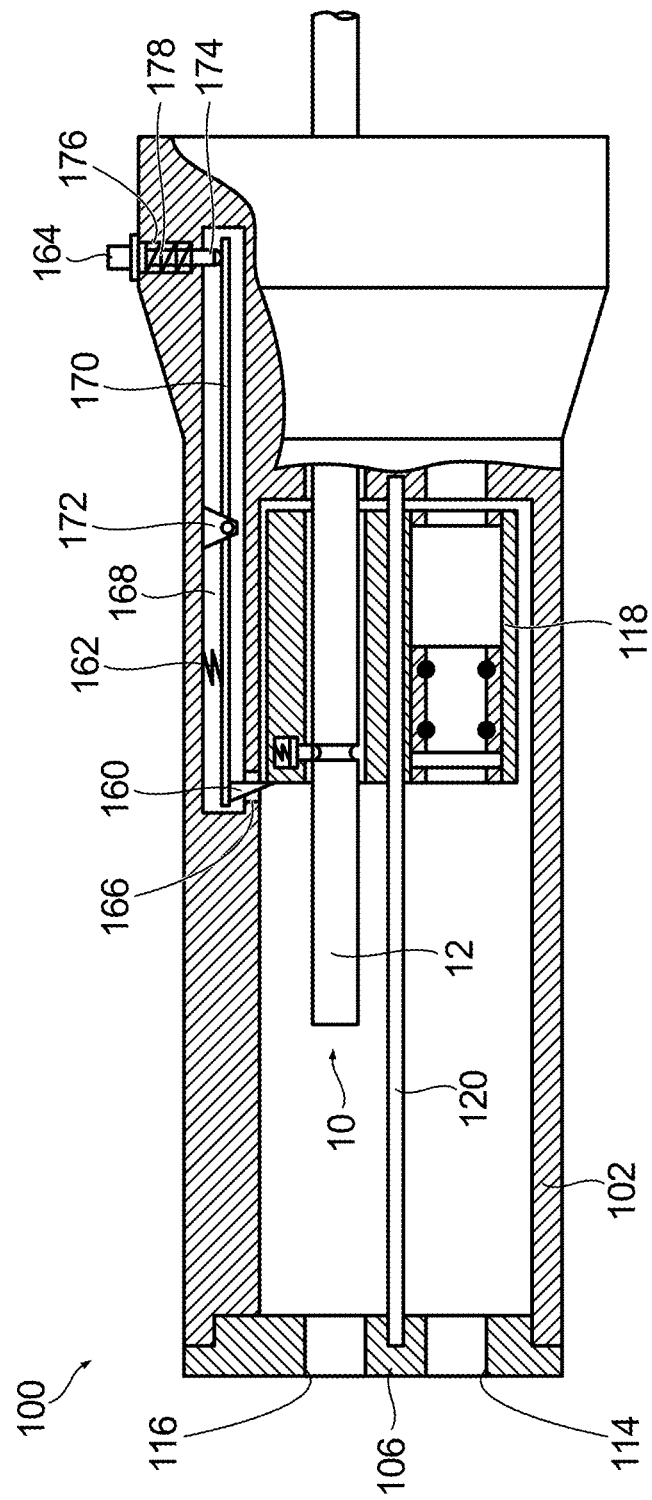
FIG. 14 is a schematic configuration diagram of a main section of a fourth embodiment of an endoscopic surgery device.

FIG. 14 is a schematic configuration diagram of a main section of a fourth embodiment of the endoscopic surgery device in accordance with the present invention.

The endoscopic surgery device of the fourth embodiment is different from the endoscopic surgery device of the third embodiment described above in that the endoscopic surgery device of the fourth embodiment includes a lock mechanism (movement regulating member) for locking the slider 118 in the outer tube body. Thus, hereinafter only the lock mechanism for the slider 118, which is the different portion, will be described.

The lock mechanism for locking the slider 118 is configured to include: a slider lock pin (mobile object lock pin) 160 provided so as to be retractable on a moving path of the slider 118; a slider lock pin urging spring (mobile object lock pin urging member) 162 for urging the slider lock pin 160 in a direction in which the slider lock pin 160 projects; and a slider lock release button (mobile object lock release member) 164 for forcing the slider lock pin 160 to retract.

The slider lock pin 160 is formed into a wedge shape so that an inclined surface is formed in a side facing to the distal end of the outer tube body 102, and a vertical surface is formed in a side facing to the proximal end of the outer tube body 102 so as to be orthogonal to the axis of the outer tube body 102. On the inner peripheral surface of the outer tube body 102, there is formed a slider lock pin housing hole 166 into which the slider lock pin 160 is to be housed. The slider lock pin 160 is housed in the slider lock pin housing hole 166 and is provided so as to be retractable from the inner peripheral portion of the outer tube body 102 which serves as the moving path of the slider 118.

The outer tube body 102 includes a hollow portion 168 and a rod-like slider lock pin support arm 170 is housed in the hollow portion 168. The slider lock pin support arm 170 is arranged parallel to the axis of the outer tube body 102. The slider lock pin support arm 170 is provided with a shaft at its approximately central position in a longitudinal direction. The shaft is pivotably supported by a bearing 172 provided in the hollow portion 168 so as to be swingably supported. The slider lock pin 160 is attached to a front end of the slider lock pin support arm 170 and is housed in the slider lock pin housing hole 166. The slider lock pin 160 is retractable from the slider lock pin housing hole 166 by swinging the slider lock pin support arm 170.

The slider lock pin urging spring 162 is composed of a coil spring, for example, and is arranged in the hollow portion 168. The slider lock pin urging spring 162 urges the slider lock pin support arm 170 so that the slider lock pin 160 projects from the slider lock pin housing hole 166. Thus, the slider lock pin urging spring 162 is arranged on the distal end side with respect to the bearing 172.

The slider lock release button 164 is provided in the proximal end portion of the outer tube body 102. In addition, the slider lock release button 164 is configured as a press-button, and is attached to a front end of a button shaft 174 provided in the proximal end portion of the outer tube body 102.

The button shaft 174 is housed in a button shaft housing hole 176 formed in the proximal end portion of the outer tube body 102 and is slidable in the radial direction of the outer tube body 102. The button shaft housing hole 176 houses a coil spring 178 that urges the slider lock release button 164 in a direction in which the slider lock release button 164 projects.

A front end of the button shaft 174 is in contact with the slider lock pin support arm 170. When the slider lock release button 164 is pressed to push the button shaft 174, the front end of the button shaft 174 pushes down on the slider lock pin support arm 170 to swing the slider lock pin support arm 170. As a result, the slider lock pin 160 retracts into the slider lock pin housing hole 166 to retract from the inner peripheral portion of the outer tube body 102 which serves as the moving path of the slider 118.

(Operation)

Next, operation of the endoscopic surgery device of the fourth embodiment configured as above will be described.

Since operation other than the lock mechanism for locking the slider 118 is the same as the operations of the endoscopic surgery device of the third embodiment described above, hereinafter only an operation of the lock mechanism for locking the slider 118 will be described.

In the endoscopic surgery device of the fourth embodiment, the slider 118 can be locked in the outer tube.

Figure 15:
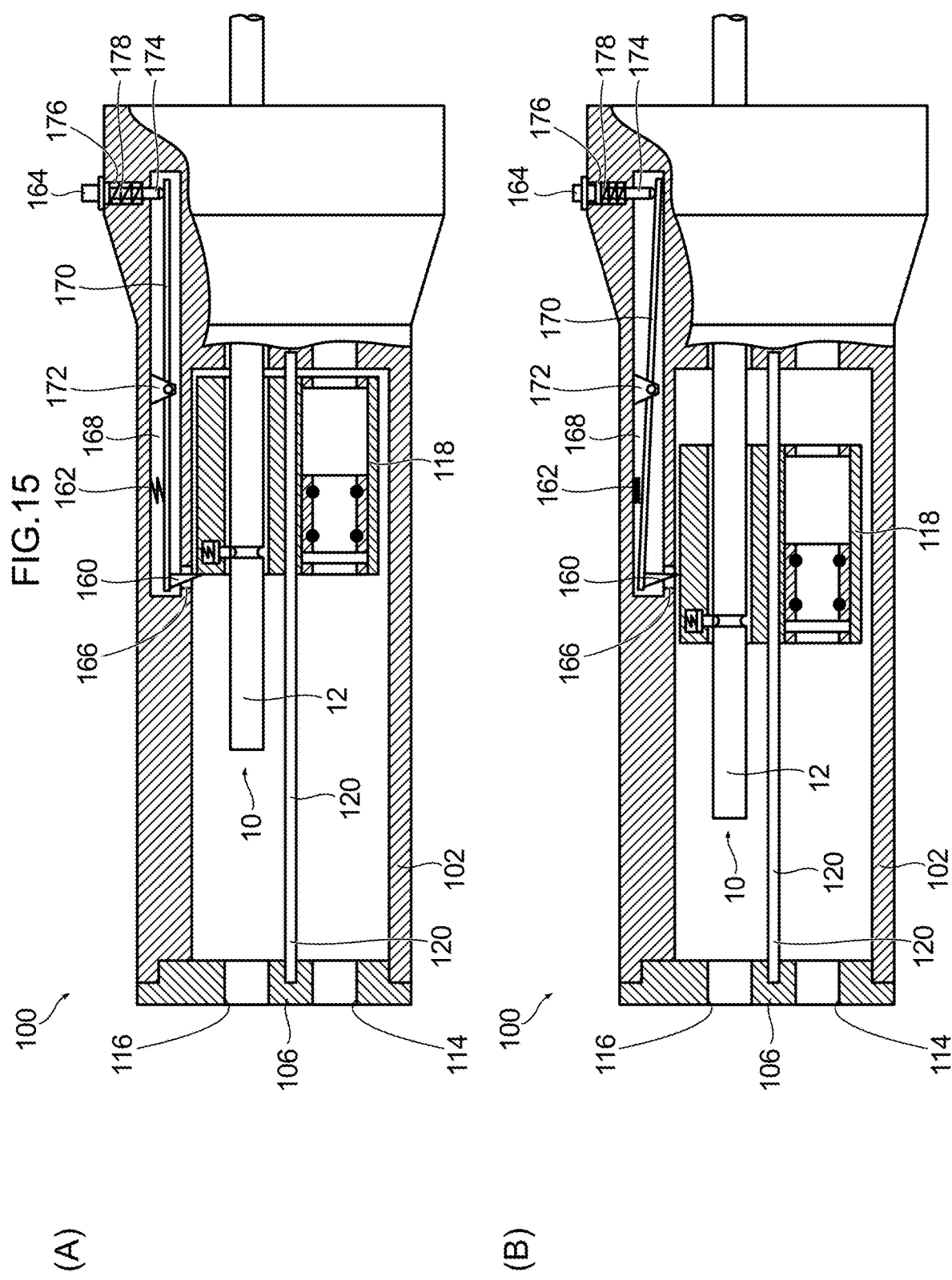
FIG. 15 is an explanatory diagram of operation of a lock mechanism for locking a slider.

FIG. 15 is an explanatory diagram of operation of the lock mechanism for locking the slider.

As shown in FIG. 15, in a normal state (in a state where the slider lock release button 164 is not pressed), the slider lock pin 160 projects from the slider lock pin housing hole 166 to project into the inner peripheral portion of the outer tube body 102, serving as the moving path of the slider 118. The slider 118 is brought into contact with the slider lock pin 160 so that movement of the slider 118 is regulated.

As shown in (A) of FIG. 15, a position at which the slider lock pin 160 projects is set so that the front end of the slider 118 is brought into contact with the slider lock pin 160 when the slider 118 is positioned at a position closest to the proximal end side in the outer tube body. That is, a projecting position of the slider lock pin 160 is set so that the slider 118 is locked when the slider 118 is positioned at the position (movement regulation position) closest to the proximal end side in the outer tube body.

The endoscope 10 and the treatment tool 50 are inserted into the outer tube 100 in the state where the slider 118 is locked. Accordingly, it is possible to prevent the slider 118 from moving to allow the endoscope 10 and the treatment tool 50 to be easily and smoothly inserted into the outer tube 100.

After the endoscope 10 and the treatment tool 50 are inserted into the outer tube 100, the lock of the slider 118 is released. The lock of the slider 118 is released by pressing the slider lock release button 164.

When the slider lock release button 164 is pressed to push the button shaft 174, the front end of the button shaft 174 pushes down on the slider lock pin support arm 170. As a result, the slider lock pin support arm 170 swings with a shaft as a fulcrum to allow the slider lock pin 160 to retract into the slider lock pin housing hole 166. As a result, the lock of the slider 118 is released to allow the slider 118 to move.

In a case of locking the slider 118 again, the slider 118 is moved toward the proximal end part of the outer tube body 102. When the slider 118 moves to the proximal end part of the outer tube body 102, the slider lock pin 160 projects from the slider lock pin housing hole 166 by using urging force of the slider lock pin urging spring 162 to regulate forward movement of the slider 118. As a result, the slider 118 is locked again.

As described above, according to the endoscopic surgery device of this embodiment, it is possible to lock and unlock the slider 118. Thus, it is possible to smoothly and easily insert the endoscope 10 and the treatment tool 50 into the outer tube 100, so that handling can be easier.

Fifth Embodiment (Configuration)

Figure 16:
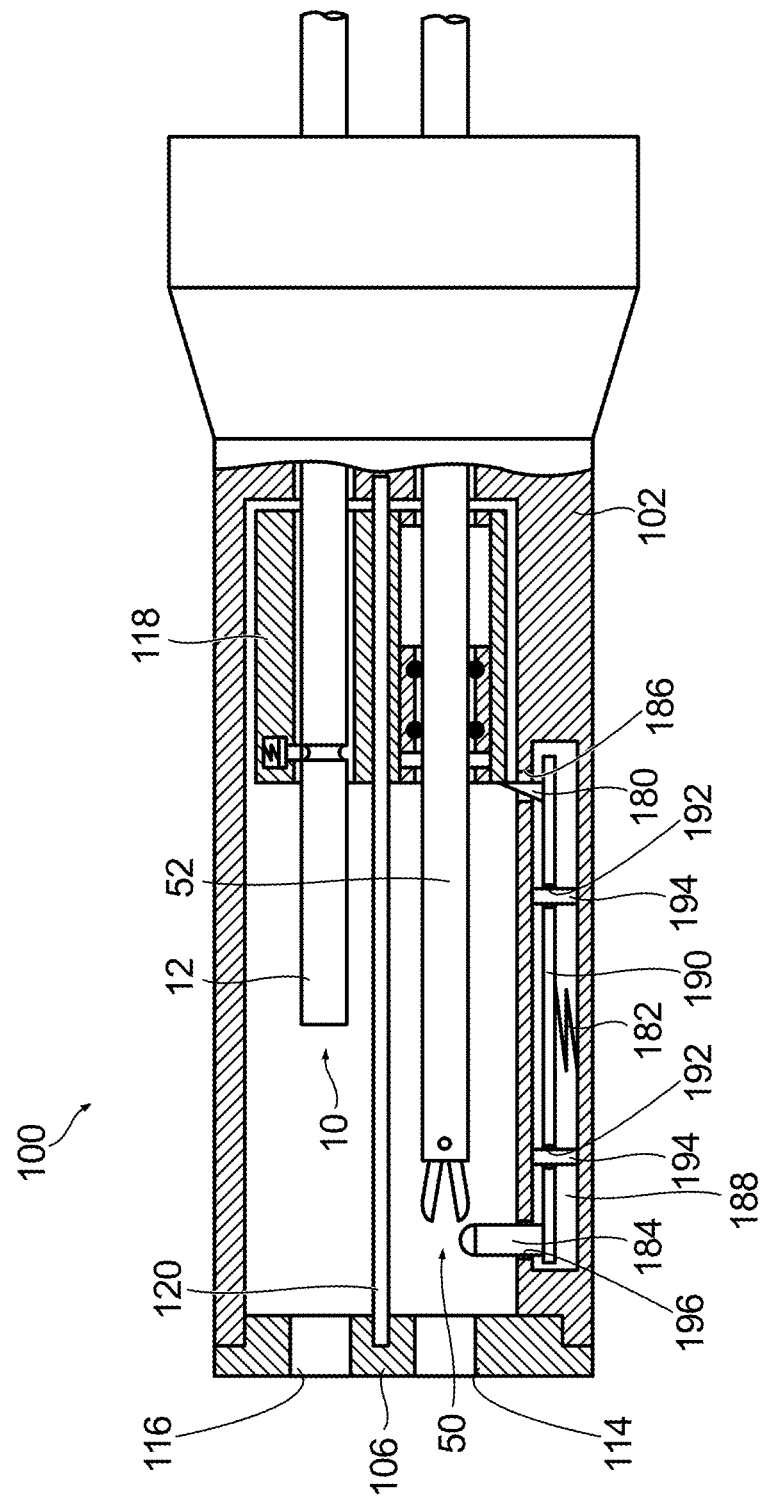
FIG. 16 is a schematic configuration diagram of a main section of a fifth embodiment of an endoscopic surgery device.

FIG. 16 is a schematic configuration diagram of a main section of a fifth embodiment of the endoscopic surgery device in accordance with the present invention.

The endoscopic surgery device of the fifth embodiment also includes a lock mechanism (movement regulating member) for locking the slider 118 in the outer tube body as with the endoscopic surgery device of the fourth embodiment. Thus, hereinafter only the lock mechanism for locking the slider 118 will be described.

The lock mechanism for locking the slider 118 of the fifth embodiment includes: a slider lock pin (mobile object lock pin) 180 provided so as to be retractable on a moving path of the slider 118; a slider lock pin urging spring (mobile object lock pin urging member) 182 for urging the slider lock pin 180 in a direction in which the slider lock pin 180 projects; and a slider lock release button (mobile object lock release member) 184 that is engaged with the treatment tool 50 inserted into the outer tube 100 to force the slider lock pin 180 to retract.

The slider lock pin 180 is formed into a wedge shape so that an inclined surface is formed in a side facing to the distal end of the outer tube body 102 and a vertical surface is formed in a side facing to the proximal end of the outer tube body 102 so as to be orthogonal to the axis of the outer tube body 102. In the inner peripheral surface of the outer tube body 102, there is formed a slider lock pin housing hole 186 into which the slider lock pin 180 is to be housed. The slider lock pin 180 is housed in the slider lock pin housing hole 186 so as to be retractable from the inner peripheral portion of the outer tube body 102, serving as the moving path of the slider 118.

The outer tube body 102 includes a hollow portion 188 in which a rod-like lifting bar 190 is housed. The lifting bar 190 is arranged parallel to the axis of the outer tube body 102, and is provided with a pair of guide holes 192. In the hollow portion 188, there is arranged a pair of guide bars 194 inserted into the pair of guide holes 192. The pair of guide bars 194 is arranged along the radial direction of the outer tube body 102. The lifting bar 190 is supported so as to be movable up and down in the radial direction of the outer tube body 102 by being guided by the guide bar 194. The slider lock pin 180 is attached to a base end part of the lifting bar 190 and is housed in the slider lock pin housing hole 186. The slider lock pin 180 is retractable from the slider lock pin housing hole 186 by moving the lifting bar 190 up and down.

The slider lock pin urging spring 182 is composed of a coil spring, for example, and is arranged in the hollow portion 188. The slider lock pin urging spring 182 urges the lifting bar 190 so that the slider lock pin 180 projects from the slider lock pin housing hole 186.

A slider lock release pin 184 is arranged inside the outer tube body on its distal end side so as to be movable up and down in the radial direction of the outer tube body 102. The slider lock release pin 184 is formed into a columnar shape, and includes a front end part formed into a hemisphere shape. In the outer tube body 102, there is formed a slider lock release pin insertion hole 196 into which the slider lock release pin 184 is inserted. The slider lock release pin insertion hole 196 is formed to communicate with the hollow portion 188. The slider lock release pin 184 is fixed to a front end of the lifting bar 190 through the slider lock release pin insertion hole 196. Thus, when the lifting bar 190 is moved, the slider lock release pin 184 also moves (up and down) in conjunction with the lifting bar 190.

(Operation)

Next, operation of the endoscopic surgery device of the fifth embodiment configured as above will be described.

Since operation other than the lock mechanism for locking the slider 118 is the same as the operations of the endoscopic surgery device of the third embodiment described above, hereinafter only an operation of the lock mechanism for locking the slider 118 will be described.

In the endoscopic surgery device of the fifth embodiment, the slider 118 can be locked in the outer tube.

Figure 17:
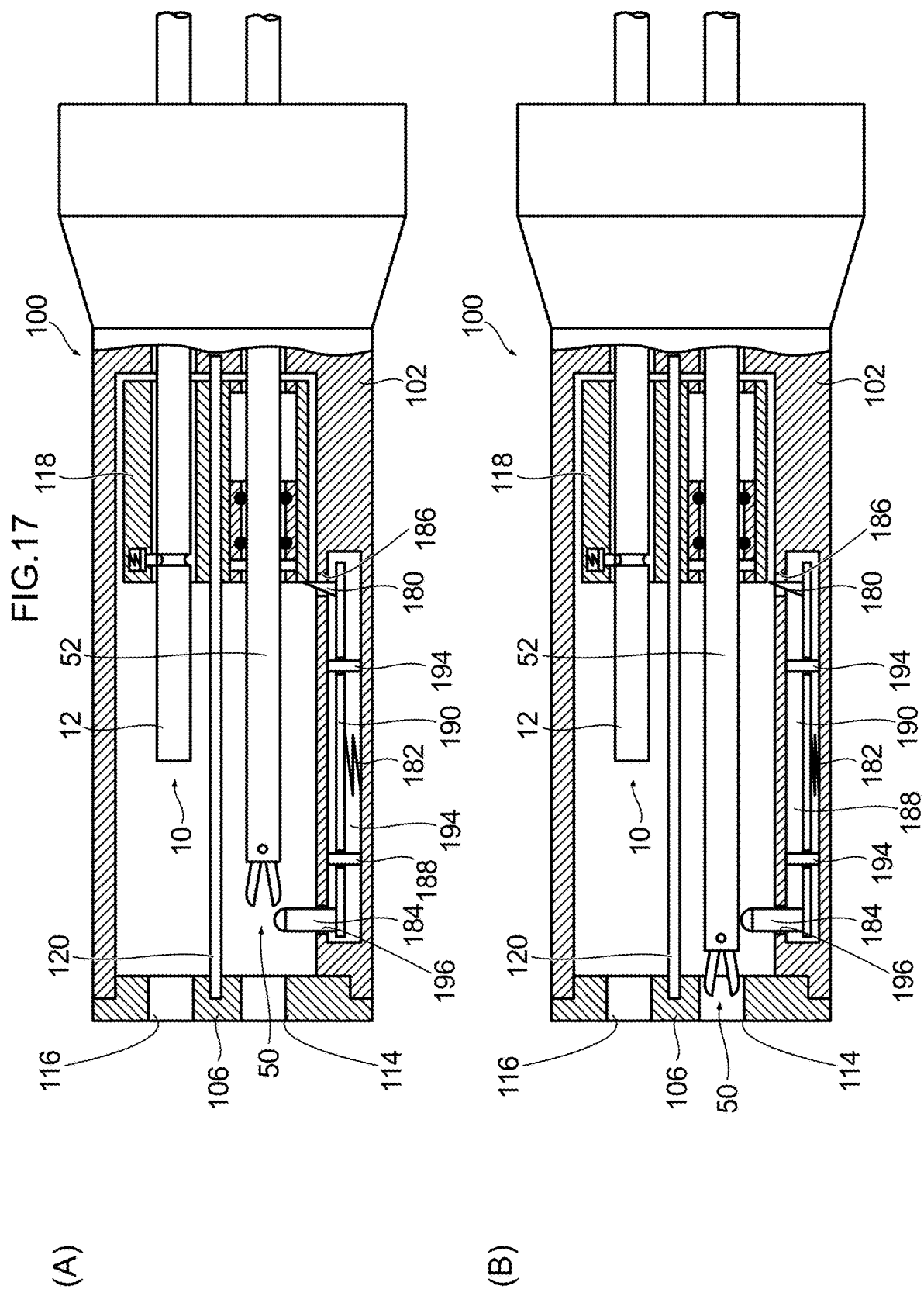
FIG. 17 is an explanatory diagram of operation of a lock mechanism for locking a slider.

FIG. 17 is an explanatory diagram of operation of the lock mechanism for locking the slider.

FIG. 17(A) shows a state where the slider 118 is locked. As shown in FIG. 17(A), the slider 118 is locked when the slider 118 is positioned at a position (movement regulation position) closest to the proximal end side of the outer tube body 102. Thus, the slider lock pin 180 is set at a position where the slider lock pin 180 is brought into contact with the front end of the slider 118 when the slider 118 is positioned at the position (movement regulation position) closest to the proximal end side of the outer tube body 102.

When the insertion section 52 of the treatment tool 50 is inserted into the outer tube 100 in a state where the slider 118 is locked, the insertion section 52 of the treatment tool 50 is first inserted into the slide sleeve 140 provided in the slider 118.

When the insertion section 52 of the treatment tool 50 is further inserted into the outer tube 100, the treatment tool 50 is brought into contact with the slider lock release pin 184 at a setting position of the slider lock release pin 184.

When the insertion section 52 of the treatment tool 50 is furthermore inserted into the outer tube 100, as shown in FIG. 17(B), the slider lock release pin 184 retracts into the slider lock release pin insertion hole 196 by being pressed by the insertion section 52 of the treatment tool 50, and then the insertion section 52 of the treatment tool 50 presses the slider lock release pin 184 to allow the lifting bar 190 to be pressed down (moved toward an outer periphery of the outer tube 100).

Since the lifting bar 190 is provided integrally with the slider lock pin 180, pressing the lifting bar 190 down allows the slider lock pin 180 to be also pressed down, namely, to retract into the slider lock pin housing hole 186. As a result, the slider lock pin 180 retracts from the moving path of the slider 118 to release the lock of the slider 118.

Figure 18:
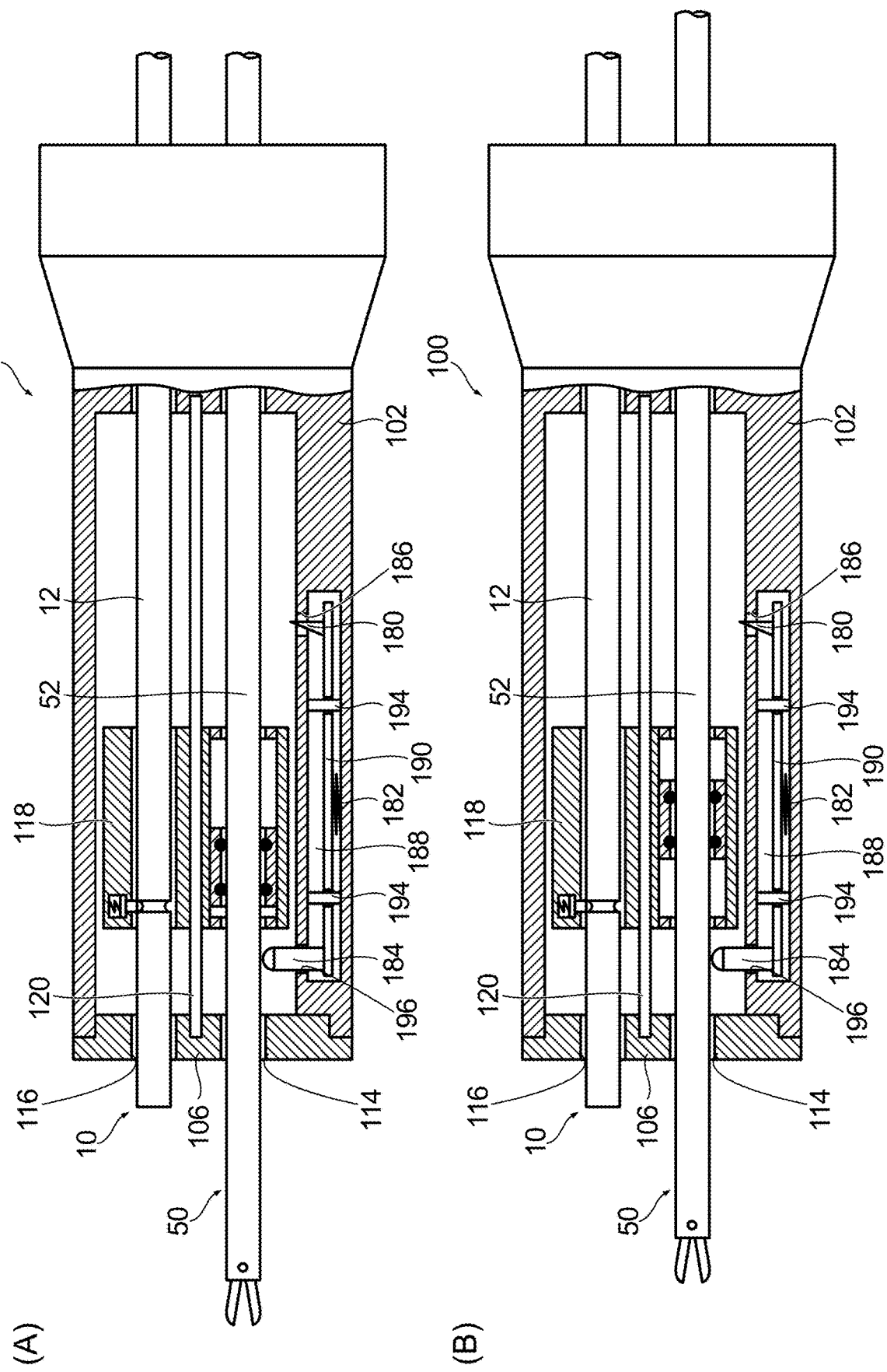
FIG. 18 is an explanatory diagram of operation of a lock mechanism for locking a slider.

After the lock of the slider 118 is released, as shown in FIG. 18, the slider 118 moves in conjunction with movement of the treatment tool 50. As a result, the endoscope 10 moves in conjunction with the treatment tool 50.

The lock of the slider 118 is released by operation of extracting the treatment tool 50 from the outer tube 100.

When the treatment tool 50 is moved in a direction of extracting the treatment tool 50 from the outer tube 100 (direction to the proximal end part of the outer tube 100), the slider 118 also moves in the direction to the proximal end part of the outer tube 100 in conjunction with the treatment tool 50.

When the slider 118 reaches the proximal end part in the outer tube body, further movement of the slider 118 toward the direction to the proximal end is regulated (restricted).

At that time, since there is not the slider 118 above the slider lock pin 180, the slider lock pin 180 can project from the slider lock pin housing hole 186. However, since the slider lock release pin 184 is still engaged with the insertion section 52 of the treatment tool 50, the slider lock pin 180 is still housed in the slider lock pin housing hole 186.

In that state, when the treatment tool 50 is further moved in the direction of extracting the treatment tool 50 from the outer tube 100, the insertion section 52 of the treatment tool 50 is gradually extracted from the slide sleeve 140 provided in the slider 118.

When a distal end of the insertion section 52 of the treatment tool 50 passes through the setting position of the slider lock release pin 184, force of pressing the slider lock release pin 184 by the treatment tool 50 is released to allow the slider lock release pin 184 to move in the direction in which the slider lock release pin 184 projects from the slider lock release pin insertion hole 196. Accordingly, when the slider lock release pin 184 moves in the direction in which the slider lock release pin 184 projects from the slider lock release pin insertion hole 196, the slider lock pin 180 projects from the slider lock pin housing hole 186 to regulate movement of the slider 118 toward the distal end, namely, to lock the movement of the slider 118.

As described above, according to the endoscopic surgery device of the fifth embodiment, it is possible to automatically lock and unlock the slider 118 by operation of inserting and extracting the treatment tool 50. As a result, it is possible to very easily insert the endoscope 10 and the treatment tool 50 into the outer tube 100.

As described above, the lock of the slider 118 is released when the insertion section 52 of the treatment tool 50 is inserted by a predetermined amount (when an amount of projection from the front end of the slider 118 reaches a predetermined amount, the lock is released). The position where the lock of the slider 118 is released is determined in accordance with the setting position of the slider lock release pin 184. Thus, the slider lock release pin 184 is arranged at a position so that an amount of projection of the insertion section 52 of the treatment tool 50 with respect to the slider 118 becomes optimum. Accordingly, the treatment tool 50 can be held at an optimum position by only inserting the treatment tool 50, so that setting can be very easily performed.

A holding position of the treatment tool 50 with respect to the slider 118 is set in consideration of an imaging range of the endoscope 10 held in the same slider 118.

Other Embodiments

In the embodiments described above, although there are described examples of using an endoscope without illumination means, an endoscope provided at its insertion section with illumination means can also be used as an endoscope to be inserted into an outer tube.

In addition, although the embodiments described above are configured to lock a slider by regulating movement of the slider with a pin projecting in a moving path of the slider, means which locks the slider is not limited to the configuration above.

Further, in the embodiments described above, although there are described examples of fixing a slider at a proximal end part in an outer tube body, the slider can be fixed at an arbitrary position.

Furthermore, in a series of the embodiments described above, although an endoscope and a treatment tool are detachable from the outer tube, an undetachable structure may be applied. That is, an endoscope and a treatment tool may be configured to be integrally attached to a slider, or only either an endoscope or a treatment tool may be configured to be detachable. Meanwhile, allowing an endoscope and a treatment tool to be detachable from an outer tube can facilitate operation such as cleaning and maintenance.

EXAMPLE

An example of the present invention will be described.
Hereinafter, only an example of an outer tube will be described.
(Configuration)
FIG. 19 is an external view showing an example of an outer tube to which the present invention is applied.

The outer tube 200 is provided with an outer tube body 202 that is formed into a cylindrical shape. The outer tube body 202 is provided at its rear end (proximal end) with a rear end cap 204, and at its front end with a front end cap 206.

Figure 20:
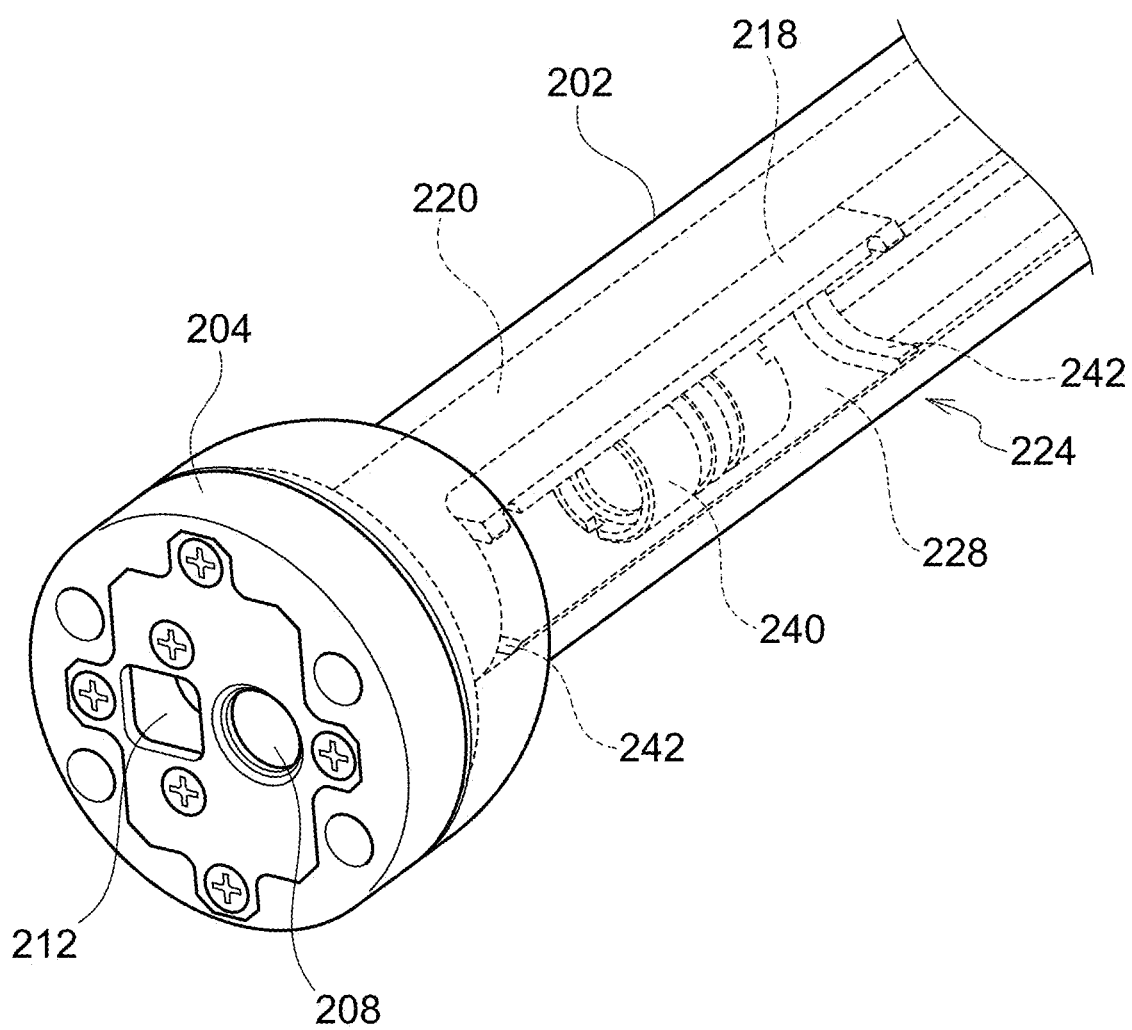
FIG. 20 is an enlarged perspective view of a rear end of an outer tube.
Figure 23:
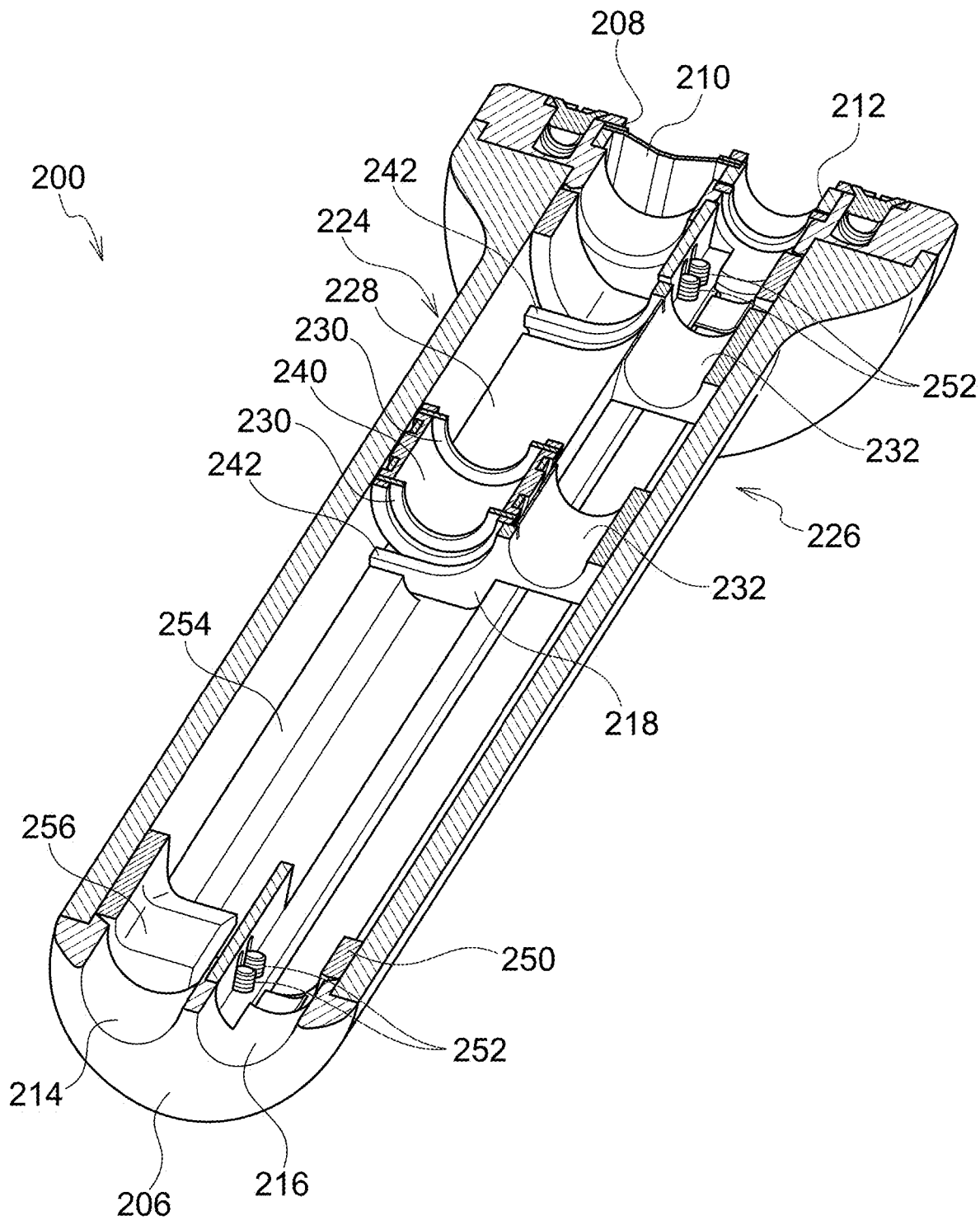
FIG. 23 is a sectional perspective view showing an inside structure of an outer tube (when a slider is locked).

As shown in FIG. 20, the rear end cap 204 is formed into a disk shape. On the rear end cap 204, there are formed a treatment tool insertion port 208 through which an insertion section of a treatment tool is inserted into the outer tube body, and an endoscope insertion port 212 through which an insertion section of an endoscope is inserted into the outer tube body. The treatment tool insertion port 208 is provided with a valve 210, as shown in FIG. 23. The valve 210 is composed of a rubber plate with a slit, for example. When the treatment tool is not inserted, the valve 210 seals the treatment tool insertion port 208.

Figure 19:
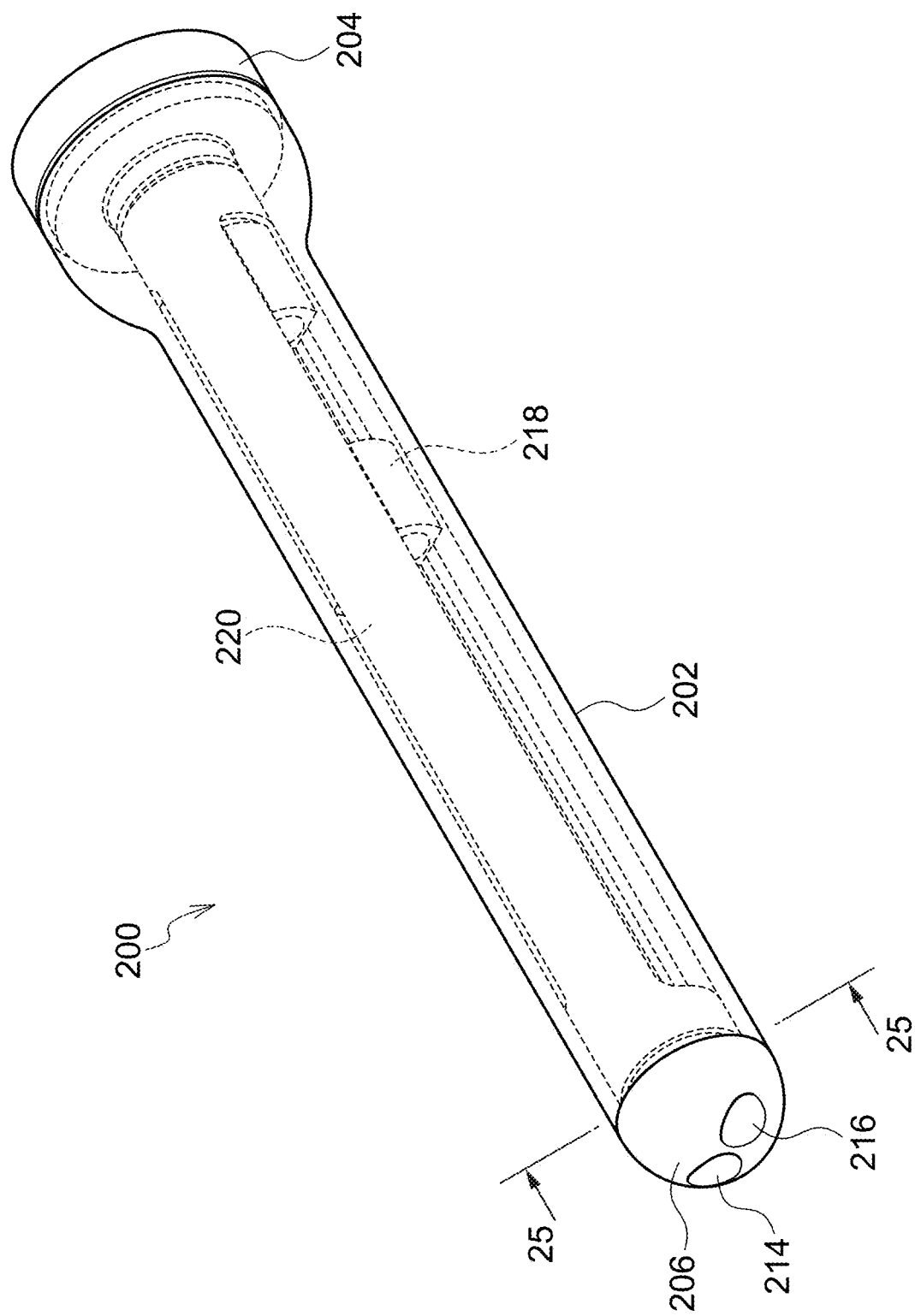
FIG. 19 is an external view showing an example of an outer tube.

As shown in FIG. 19, the front end cap 206 is formed into a hemisphere shape. On the front end cap 206, there are formed a treatment tool feed port 214 through which the insertion section of the treatment tool inserted into the outer tube body 202 from the treatment tool insertion port 208 is fed, and an endoscope feed port 216 through which the insertion section of the endoscope inserted into the outer tube body 202 from the endoscope insertion port 212 is fed.

The treatment tool insertion port 208 and the treatment tool feed port 214 are coaxially arranged so as to be linearly parallel to an axis of the outer tube body 202. Accordingly, when he insertion section of the treatment tool is inserted from the treatment tool insertion port 208, the insertion section is fed parallel to the axis of the outer tube body 202 from the treatment tool feed port 214.

The endoscope insertion port 212 and the endoscope feed port 216 are coaxially arranged so as to be linearly parallel to an axis of the outer tube body 202. Accordingly, when the insertion section of the endoscope is inserted from the endoscope insertion port 212, the insertion section is fed parallel to the axis of the outer tube body 202 from the endoscope feed port 216.

That is, the insertion section of the treatment tool and the insertion section of the endoscope are fed parallel to each other from the treatment tool feed port 214 and the endoscope feed port 216, respectively.

As shown in FIG. 19, the outer tube body 202 is provided inside with a guide frame 220, a slider (mobile object) 218 provided so as to be movable in a direction parallel to the axis of the outer tube body 202 by being guided by the guide frame 220, and a slider lock frame (movement regulating member) 250 for locking and unlocking the slider 218.

Figure 21:
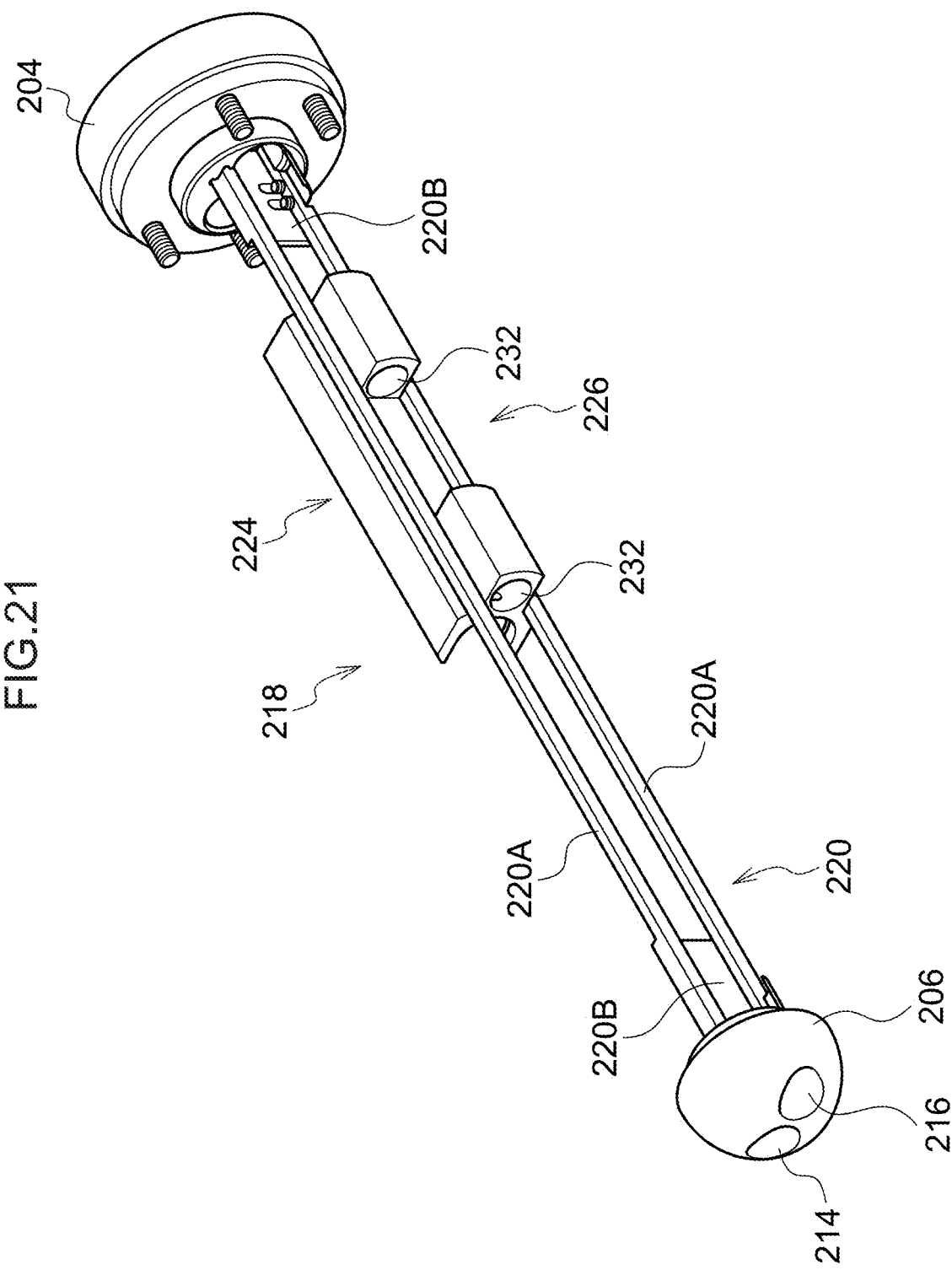
FIG. 21 is a perspective view showing an inside structure of an outer tube.
Figure 22:
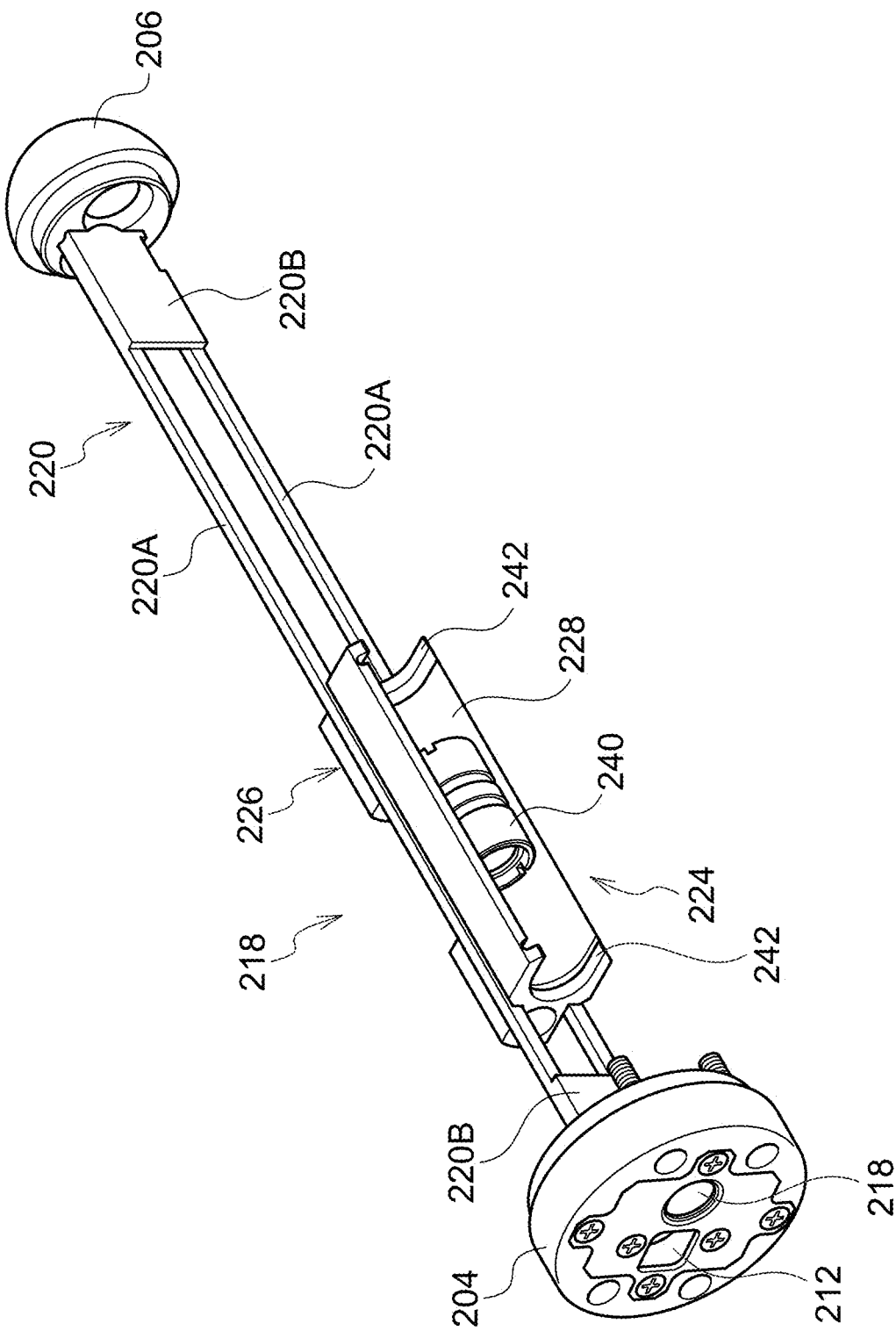
FIG. 22 is a perspective view showing an inside structure of an outer tube.

The guide frame 220 includes a pair of guide rails 220A arranged parallel to each other at a predetermined interval as shown in FIGS. 21 and 22, and a pair of stopper plates 220B provided in both respective ends of the pair of guide rails 220A, and the guide frame 220 is fixed in the outer tube body.

The pair of guide rails 220A is arranged parallel to the axis of the outer tube body 202. The slider 218 is supported so as to be movable in the outer tube body in a direction parallel to the axis of the outer tube body 202 by being guided by the guide rails 220A.

The pair of stopper plates 220B regulates a moving range of the slider 218. The slider 218 moving toward a distal end is regulated by the stopper plate 220B arranged in the distal end direction so that movement of the slider 218 to the distal end is regulated, and the slider 218 moving toward a proximal end (rear end) is brought into contact with the stopper plate 220B arranged in the proximal end direction so that movement of the slider 218 to the proximal end is regulated. That is, the slider 218 is provided so as to be movable between the pair of stopper plates 220B.

The slider 218 is formed into a block shape, and is fitted between the pair of guide rails 220A of the guide frame 220 to be slidably supported by the guide rails 220A.

Frictional force between the slider 218 and the guide rails 220A is set at a predetermined frictional force (first frictional force F1).

As shown in FIGS. 21 and 22, the slider 218 includes a treatment tool holding section 224 that holds the insertion section of the treatment tool inserted into the outer tube body 202, and an endoscope holding section 226 that holds the insertion section of the endoscope inserted into the outer tube body 202.

As shown in FIGS. 21 to 24, the treatment tool holding section 224 includes: a treatment tool holding groove 228 into which the insertion section of the treatment tool is inserted; a slide sleeve (second mobile object) 240 arranged in the treatment tool holding groove 228 so as to be movable in the axial direction in the treatment tool holding groove; and a pair of O-rings (ring-shaped elastic body) 230 arranged in the slide sleeve 240.

The treatment tool holding groove 228 is formed into a U-shape parallel to the axis of the outer tube body 202, and is arranged coaxially with the treatment tool insertion port 208 and the treatment tool feed port 214.

The treatment tool holding groove 228 is provided at its both ends with respective U-shaped stopper portions 242 that are formed so as to project radially inward of the groove. The stopper portions 242 prevent the slide sleeve 240 sliding in the treatment tool holding groove 228 from coming out of the treatment tool holding groove 228. In addition, the stopper portions 242 regulate a movable range (a range of a "play"). That is, the slide sleeve 240 is provided so as to be movable between the respective stopper portions 242 provided at both ends of the treatment tool holding groove 228.

The slide sleeve 240 is formed into a cylindrical shape and is housed in the treatment tool holding groove 228. The slide sleeve 240 housed in the treatment tool holding groove 228 is arranged coaxially with the treatment tool holding groove 228. That is, the slide sleeve 240 is arranged coaxially with the treatment tool insertion port 208 and the treatment tool feed port 214. Accordingly, when inserted from the treatment tool insertion port 208 along the axial direction, the insertion section of the treatment tool can be inserted into an inner peripheral portion of the slide sleeve 240.

The frictional force between the slide sleeve 240 and the slider 218 is set at a predetermined frictional force (third frictional force F3). The frictional force (third frictional force F3) between the slide sleeve 240 and the slider 218 is set so as to be smaller than the frictional force (first frictional force F1) between the slider 218 and the guide rails 220A. Accordingly, when a force is axially applied to the slide sleeve 240, it is possible to move only the slide sleeve 240 without moving the slider 218.

The pair of O-rings 230 is attached to two places, front and rear, inside the slide sleeve 240. Each of the O-rings 230 has an inner diameter slightly smaller than an outer diameter of the insertion section of the treatment tool.

The frictional force between the O-rings 230 and the insertion section of treatment tool is set at a predetermined frictional force (second frictional force F2) so as to be larger than the frictional force (first frictional force F1) between the slider 218 and the guide rails 220A (the second frictional force F2>the first frictional force F1>the third frictional force F3).

Accordingly, it is possible to prevent the treatment tool from coming out of the slider 218 when the treatment tool is axially moved.

The insertion section of the treatment tool inserted into the outer tube body through the treatment tool insertion port 208 is fed from the treatment tool feed port 214 through the treatment tool holding groove 228. When passing through the treatment tool holding groove 228, the treatment tool passes through the inner peripheral portion of the slide sleeve 240 to be inserted into the O-rings 230 arranged in the inner peripheral portion of the slide sleeve 240. As described above, each of the O-rings 230 has the inner diameter slightly smaller than the outer diameter of the insertion section of the treatment tool. Thus, when inserted into the O-rings 230, the treatment tool is pressed by the O-rings 230 to be held in the inner peripheral portion of the slide sleeve 240.

Since the treatment tool is pressed and held by using the O-rings 230 in that case above, it is possible to arbitrarily adjust a position where the treatment tool is engaged with the slide sleeve 240 (it is possible to arbitrarily adjust a holding position with respect to the slider 218).

As shown in FIGS. 21 to 24, the endoscope holding section 226 includes an endoscope holding hole 232 through which the insertion section of the endoscope is inserted, and a pair of O-rings (ring-shaped elastic body) that is not shown and is arranged in the endoscope holding hole.

The endoscope holding hole 232 penetrates the slider 218 to form a through-hole. The endoscope holding hole 232 is formed parallel to the axis of the outer tube body 202, and is arranged coaxially with the endoscope insertion port 212 and the endoscope feed port 216.

The pair of O-rings (not shown) is attached to two places, front and rear, inside the endoscope holding hole 232. Each of the O-rings has an inner diameter slightly smaller than an outer diameter of the insertion section of the endoscope.

The insertion section of the endoscope inserted into the outer tube body through the endoscope insertion port 212 is fed from the endoscope feed port 216 through the endoscope holding hole 232. When the endoscope passes through the endoscope holding hole 232, the endoscope is allowed to pass through each of the O-rings. As described above, each of the O-rings has the inner diameter slightly smaller than the outer diameter of the insertion section of the endoscope. Thus, when the endoscope is inserted into the endoscope holding hole 232, the endoscope is pressed by each of the O-rings to be pressed and held in the endoscope holding hole.

Since the endoscope is pressed and held by using each of the O-rings in that case above, it is possible to arbitrarily adjust a holding position of the endoscope by the endoscope holding hole 232 (it is possible to arbitrarily adjust a holding position with respect to the slider 218).

Figure 24:
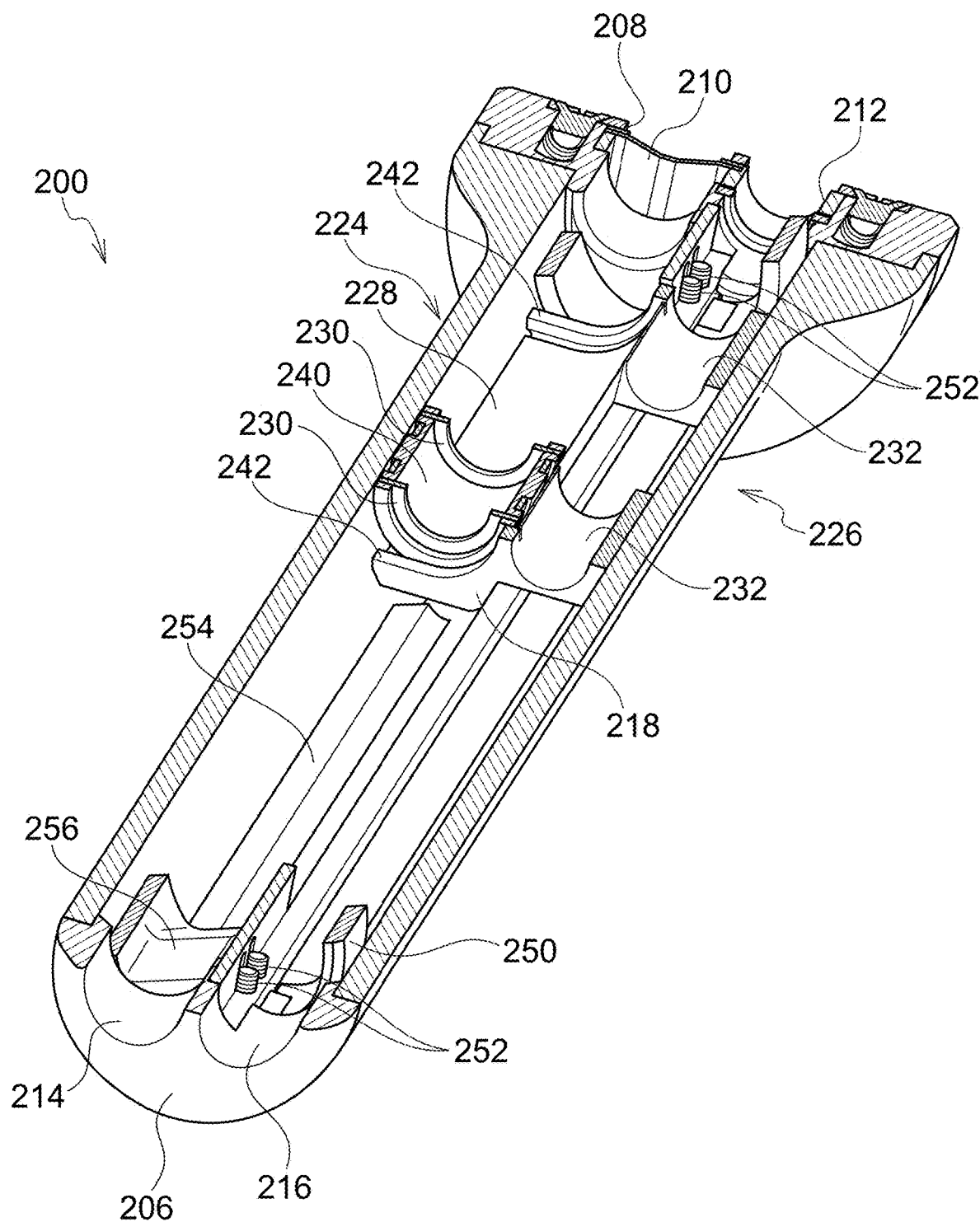
FIG. 24 is a sectional perspective view showing an inside structure of an outer tube (when lock of a slider is released).

As shown in FIGS. 23 and 24, a slider lock frame 250 is formed into a cylindrical shape. The slider lock frame 250 is housed in the outer tube body. The guide frame 220 and the slider 218 are housed inside the slider lock frame 250.

The slider lock frame 250 is provided so as to be rotatable in the outer tube body in a circumferential direction. The guide frame 220 is provided with a stopper (not shown) that regulates rotation of the slider lock frame 250 at a predetermined position. When the slider lock frame 250 rotates in a predetermined direction, the slider lock frame 250 is brought into contact with the stopper at the predetermined position and further rotation of the slider lock frame 250 is regulated.

Figure 25:
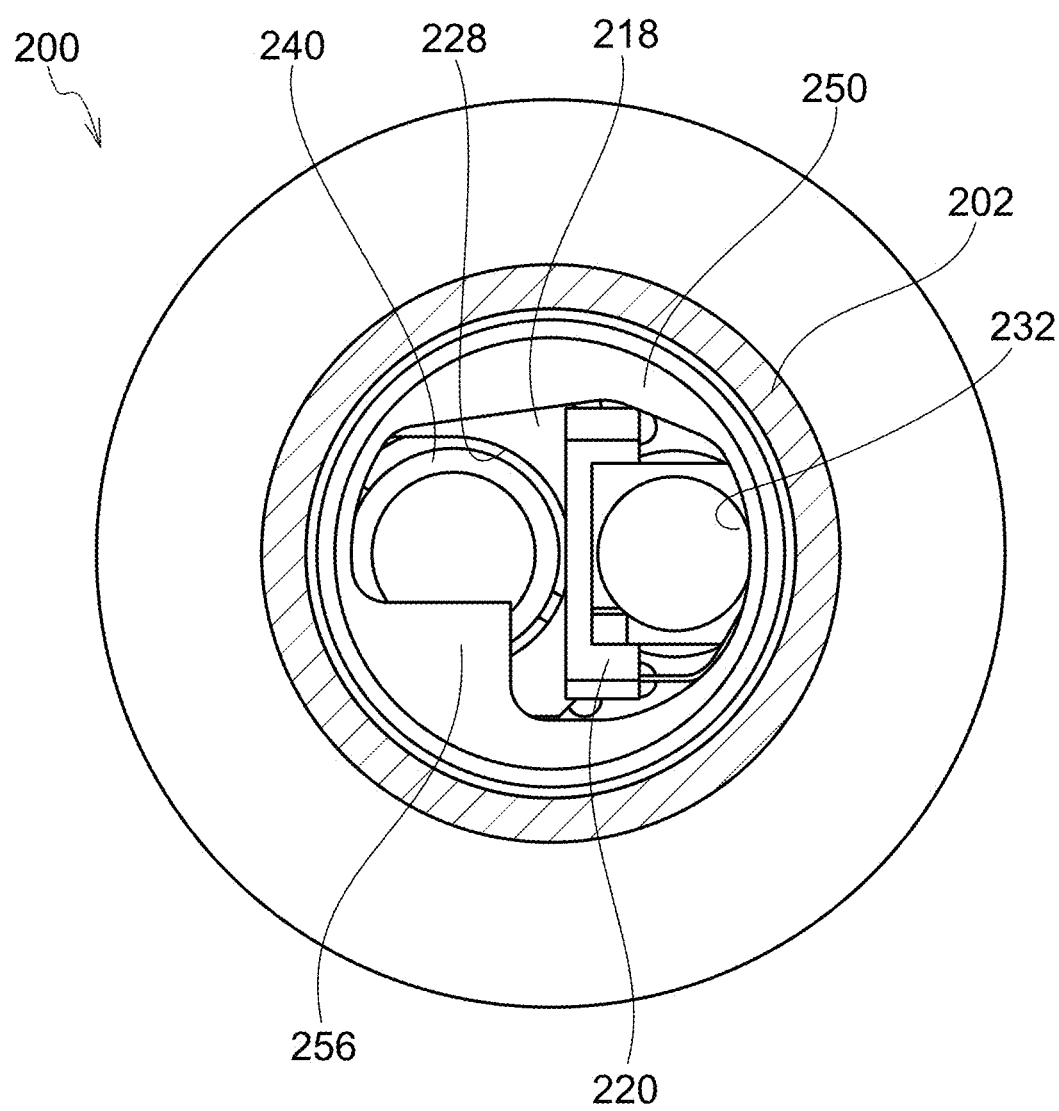
FIG. 25 is a sectional perspective view showing an inside structure of an outer tube (a sectional view taken along line 25-25 in FIG. 19, when a slider is locked).

FIGS. 23 and 25 show a state where the rotation of the slider lock frame 250 is regulated. In the state shown in FIGS. 23 and 25, the slider lock frame 250 is brought into contact with the stopper (not shown) provided in the guide frame 220 to regulate clockwise rotation in FIGS. 23 and 25.

The guide frame 220 is provided with a slider lock frame urging spring 252 (urging member) that urges the slider lock frame 250 so that the slider lock frame 250 rotates toward the stopper (clockwise in FIG. 25). The slider lock frame 250 is pressed against the stopper by being urged by the slider lock frame urging spring 252. Thus, in a state where nothing is done, the slider lock frame 250 is pressed against the stopper by the urging force of the slider lock frame urging spring 252 and is stopped and held at a fixed position. The position where the slider lock frame 250 is held by being pressed against the stopper (position in a state of FIG. 25) is indicated as a "slider lock position".

In the slider lock position, since the slider lock frame 250 is in contact with the stopper to regulate the rotation in one direction (clockwise direction in FIG. 25), the rotation in the other direction (counterclockwise direction in FIG. 25) is only allowed. In that case, the slider lock frame 250 rotates against the urging force of the slider lock frame urging spring 252.

In the inner peripheral portion of the slider lock frame 250, there are formed a slider lock portion 254 that locks movement of the slider 218 by engaging the slider lock portion 254 with a front end of the slider 218. The slider lock portion 254 is formed as a streak-like protrusion so as to extend from a distal end of an inner peripheral portion of the slider lock frame 250 toward a rear end thereof along an axis of the slider lock frame 250 (corresponding to the axis of the outer tube body 202). The slider lock portion 254 is provided with a terminal (rear end) that is set at a position where the slider 218 is locked, as follows. That is, since the slider lock portion 254 is a member that engages with the front end of the slider 218 to regulate movement of the slider 218, the position of the terminal is set so as to correspond to a position of the front end of the slider 218 when the slider 218 is positioned at a position (movement regulation position) closest to the proximal end in the outer tube body (corresponding to a case where the slider 218 is brought into contact with the stopper plate 220B on the rear end side) (the position of the terminal is set at a position slightly front side from the position of the front end of the slider 218 when the slider 218 is positioned at the position (movement regulation position) closest to the proximal end in the outer tube body).

The slider lock portion 254 projects in the moving path of the slider 218 when the slider lock frame 250 is positioned at the slider lock position, thereby regulating movement of the slider 218. When the slider lock frame 250 rotates against the urging force of the slider lock frame urging spring 252, the slider lock portion 254 retracts from the moving path, thereby allowing the slider 218 to move.

As described above, it is possible to lock and release (unlock) the slider 218 by rotating the slider lock frame 250. The slider lock frame 250 rotates in conjunction with insertion of the treatment tool into the outer tube body 202, as follows.

The front end of the inner peripheral portion of the slider lock frame 250 is provided with a treatment tool engaging portion 256 which engages with the insertion section of the treatment tool inserted into the outer tube body 202. The treatment tool engaging portion 256 is formed inside the slider lock frame 250 with a predetermined width, as a slope (tapered portion) extending to a direction parallel to the axis of the slider lock frame 250.

Figure 26:
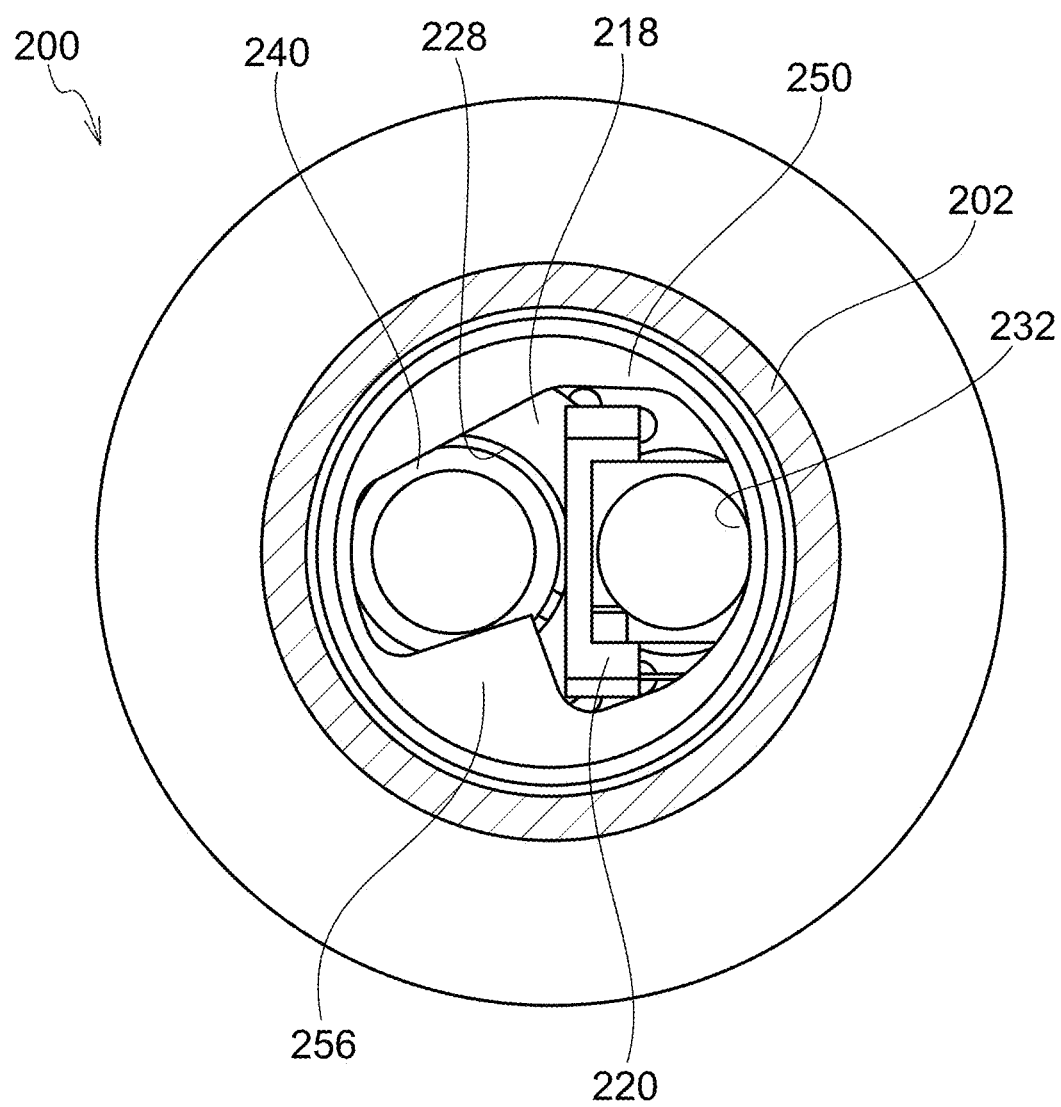
FIG. 26 is a sectional perspective view showing an inside structure of an outer tube (a sectional view taken along line 25-25 in FIG. 19, when lock of a slider is released).

The treatment tool engaging portion 256 is arranged in an insertion path of the treatment tool when the slider lock frame 250 is positioned at the slider lock position. That is, the treatment tool engaging portion 256 is arranged on a straight line connecting the treatment tool insertion port 208 and the treatment tool feed port 214. In a state where the slider lock frame 250 is positioned at the slider lock position, when the insertion section of the treatment tool is inserted from the treatment tool insertion port 208 and reaches near the distal end of the outer tube body 202, the insertion section of the treatment tool is brought into contact with the treatment tool engaging portion 256. As described above, since the treatment tool engaging portion 256 is formed as a slope, when the treatment tool is further inserted by being pressed, the treatment tool is inserted so as to press the slope down. Accordingly, as shown in FIG. 26, the slider lock frame 250 rotates. When the slider lock frame 250 rotates, the slider lock portion 254 retracts from the moving path of the slider 218 to release the lock of the slider 218, as shown in FIG. 24. That is, the slider 218 is allowed to move.

While the treatment tool is inserted, the treatment tool engaging portion 256 is engaged with the insertion section of the treatment tool. Thus, there is maintained a state where the slider lock portion 254 retracts from the moving path of the slider 218, namely, the slider 218 is allowed to arbitrarily move.

When the insertion section of the treatment tool is extracted from the treatment tool insertion port 208, engagement between the treatment tool and the treatment tool engaging portion 256 is released. As a result, the slider lock frame 250 is rotated by the urging force of the slider lock frame urging spring 252. Accordingly, the slider lock portion 254 projects in the moving path of the slider 218 to lock the slider 218.

As described above, operation of inserting and extracting the insertion section of the treatment tool allows the slider 218 to be automatically locked and unlocked.

As described above, the lock of the slider 218 is released when the insertion section of the treatment tool inserted into the outer tube body from the treatment tool insertion port 208 is brought into contact with the treatment tool engaging portion 256. Thus, it is possible to adjust a holding position of the treatment tool with respect to the slider 218, namely, an amount of projection of the treatment tool from the slider 218, by adjusting a setting position of the treatment tool engaging portion 256. In addition, optimizing the holding position of the treatment tool (an optimum position for observation with an endoscope held in the endoscope holding section 226) allows the treatment tool to be automatically held at an optimum position with respect to the endoscope by only inserting the treatment tool into the outer tube 200.

(Operation)

Next, operation of the outer tube configured as above will be described.

The outer tube 200 is penetrated through a body cavity wall, and an endoscope and a treatment tool are inserted into the outer tube 200 that guides the endoscope and the treatment tool into a body cavity of a patient. The endoscope is inserted from the endoscope insertion port 212, and the treatment tool is inserted from the treatment tool insertion port 208. The endoscope inserted into the outer tube 200 moves in conjunction with movement of the treatment tool.

Figure 27:
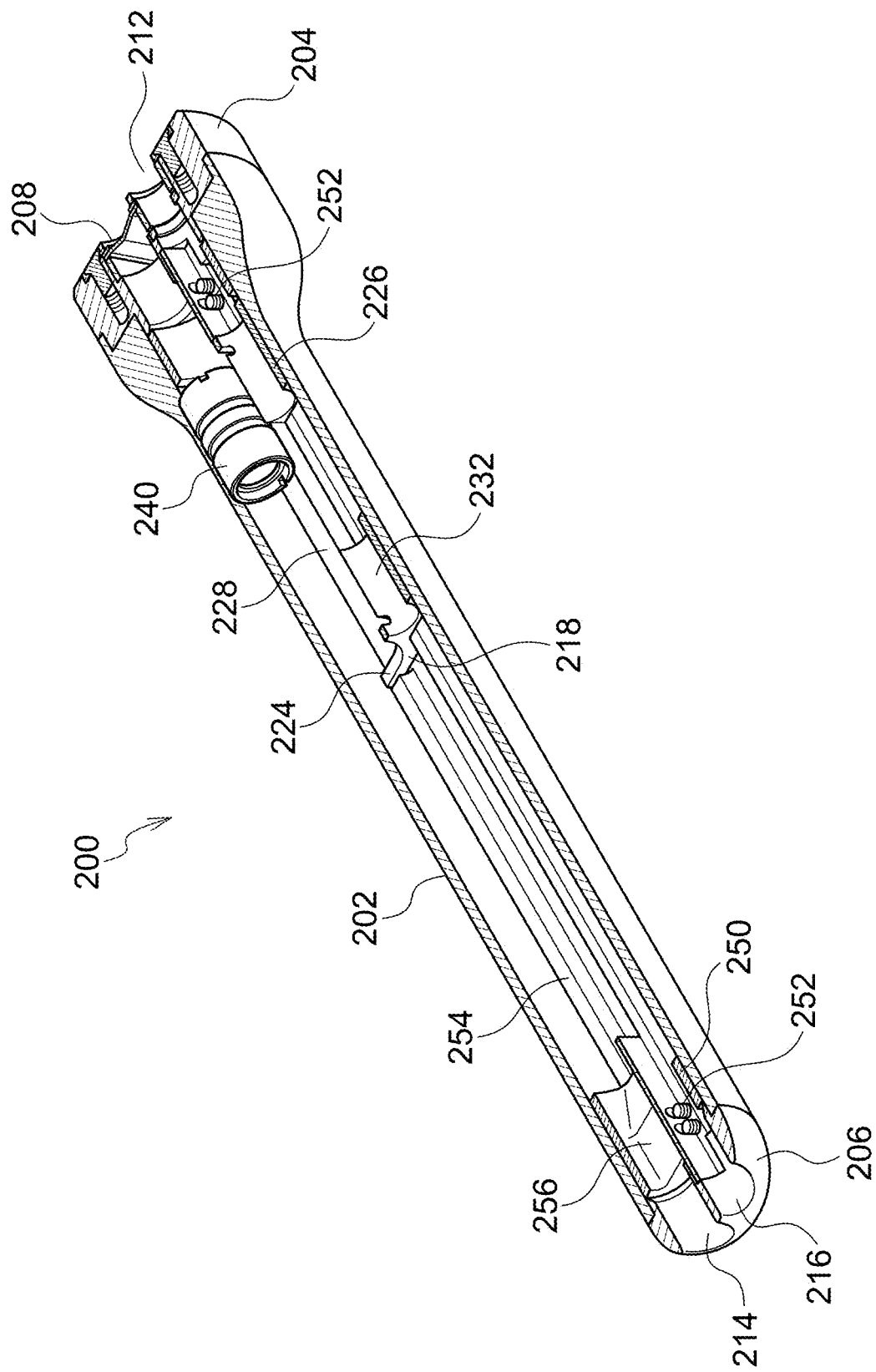
FIG. 27 is an explanatory diagram of operation of an outer tube (before a treatment tool is inserted).

FIG. 27 is a sectional view showing a state of the outer tube before a treatment tool is inserted.

As shown in FIG. 27, before a treatment tool is inserted, the slider 218 arranged in the outer tube body is positioned at the proximal end part in the outer tube body, and is locked by the slider lock frame 250 in that state. That is, in that state, the slider lock portion 254 provided in the slider lock frame 250 projects in the moving path of the slider 218, and the slider lock portion 254 engages with the front end of the slider 218 to regulate movement of the slider 218.

Figure 28:
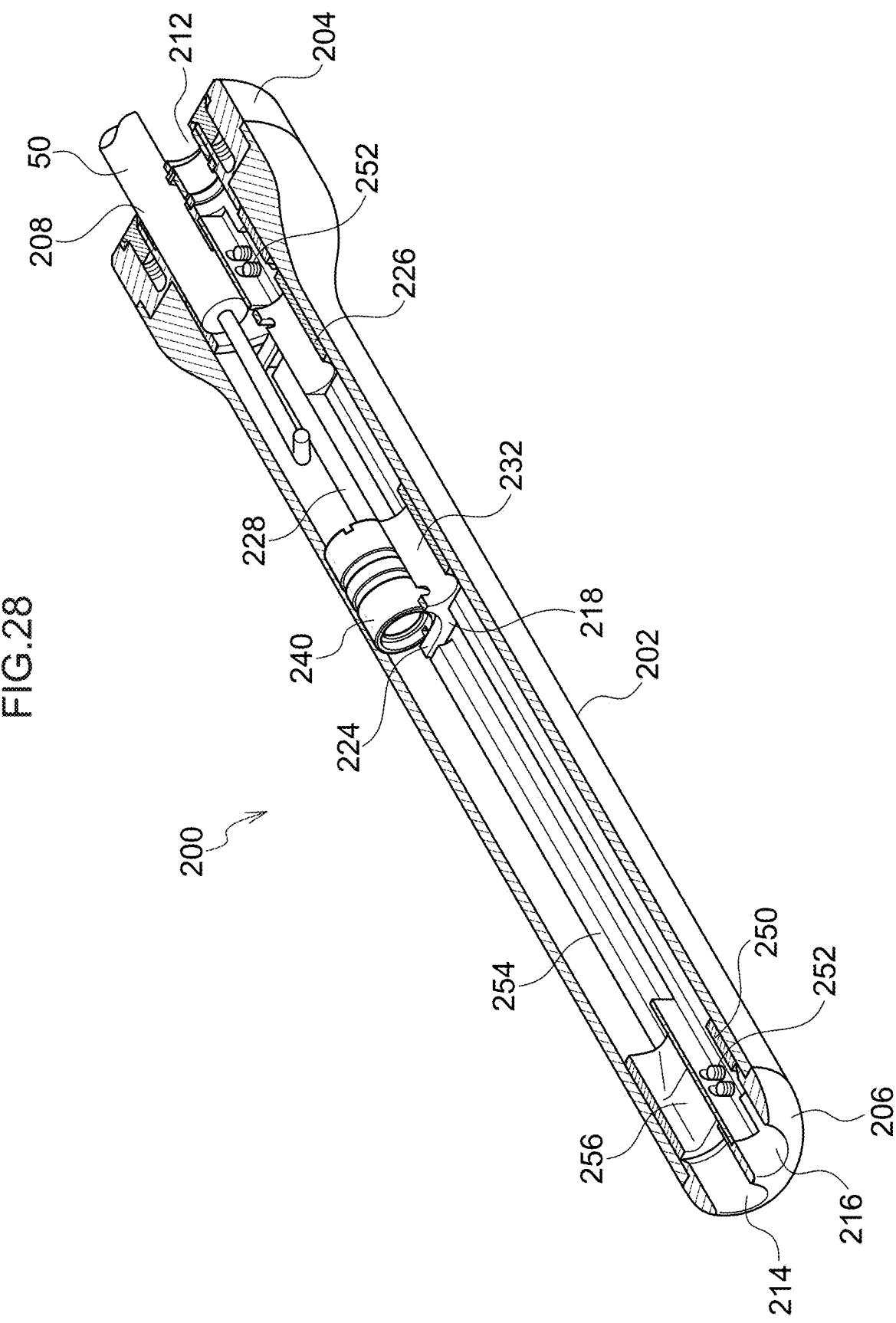
FIG. 28 is an explanatory diagram of operation of an outer tube (when a treatment tool is inserted).

As described above, a treatment tool is inserted from the treatment tool insertion port 208. As shown in FIG. 28, the treatment tool 50 is inserted parallel to the axis of the outer tube 200.

When the treatment tool 50 is pressed forward, the treatment tool 50 passes through the treatment tool holding groove 228 of the treatment tool holding section 224 provided in the slider 218 to be inserted into the inner peripheral portion of the slide sleeve 240 provided in the treatment tool holding groove 228.

Figure 29:
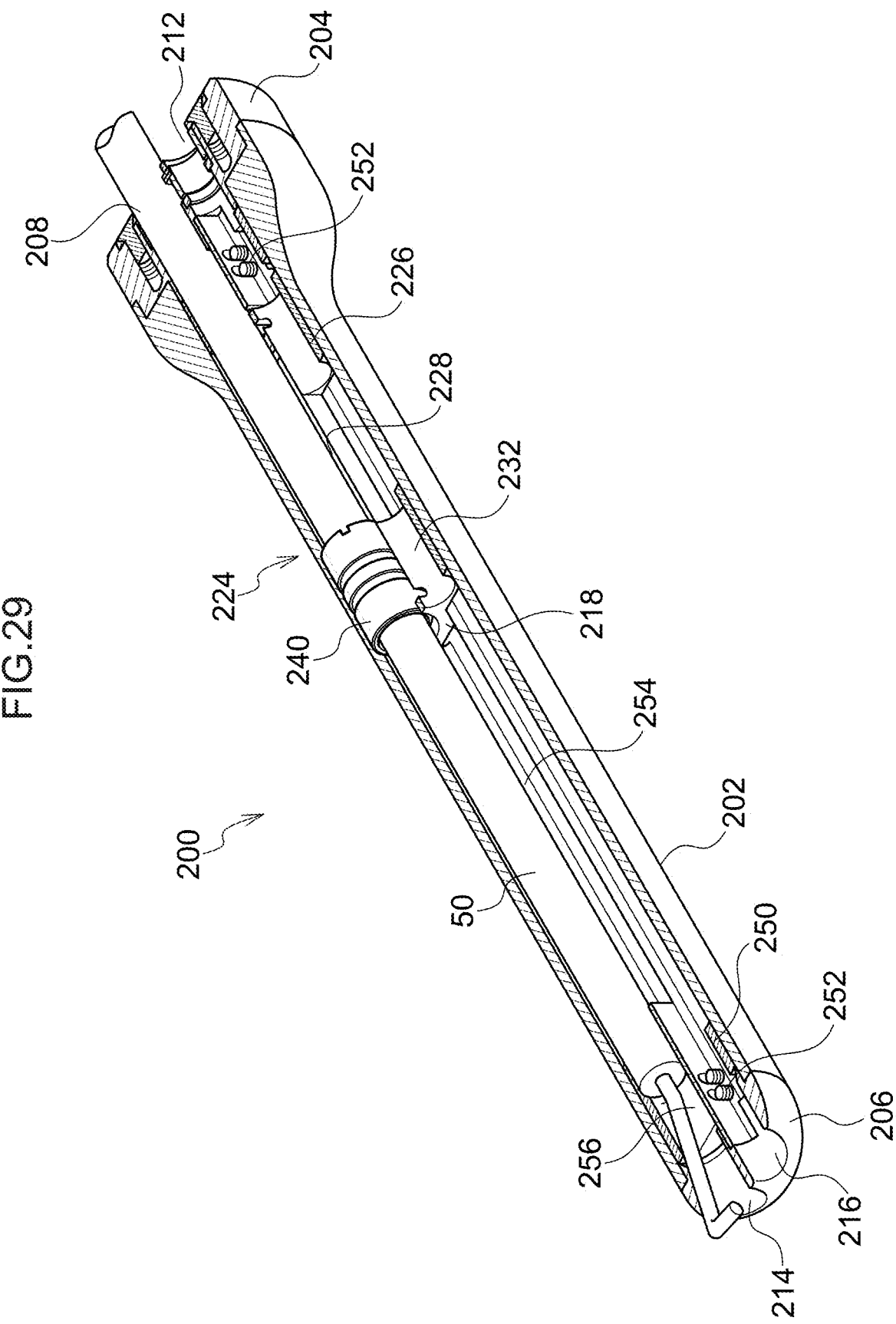
FIG. 29 is an explanatory diagram of operation of an outer tube (when a treatment tool is in contact).

When the treatment tool 50 is further pressed forward, as shown in FIG. 29, the distal end of the treatment tool 50 is brought into contact with the treatment tool engaging portion 256 provided at the front end of the inner peripheral portion of the slider lock frame 250.

Since the treatment tool engaging portion 256 is formed as a slope, when the treatment tool 50 is pressed forward, the slope is pressed down by the treatment tool 50 to rotate the slider lock frame 250. As a result, the slider lock portion 254 retracts from the moving path of the slider 218 to release the lock of the slider 218, as shown in FIG. 30, thereby allowing the slider 218 to move.

When the lock of the slider 218 is released, the treatment tool 50 projects from the slider 218 by a predetermined amount of projection. That is, the lock of the slider 218 is released when the treatment tool 50 projects from the slider 218 by the predetermined amount of projection. The amount of projection of the treatment tool 50 with respect to the slider 218 is optimized for an endoscope held by the endoscope holding section 226. Thus, it is possible to hold the treatment tool at an optimum position with respect to the endoscope held in the endoscope holding section 226 at the same time when the lock of the slider 218 is released.

While the treatment tool 50 is inserted, the treatment tool engaging portion 256 engages with the treatment tool 50. Thus, there is maintained a state where the slider lock portion 254 retracts from the moving path of the slider 218. That is, the slider 218 is allowed to arbitrarily move. As a result, the slider 218 moves in conjunction with movement of the treatment tool 50.

Figure 30:
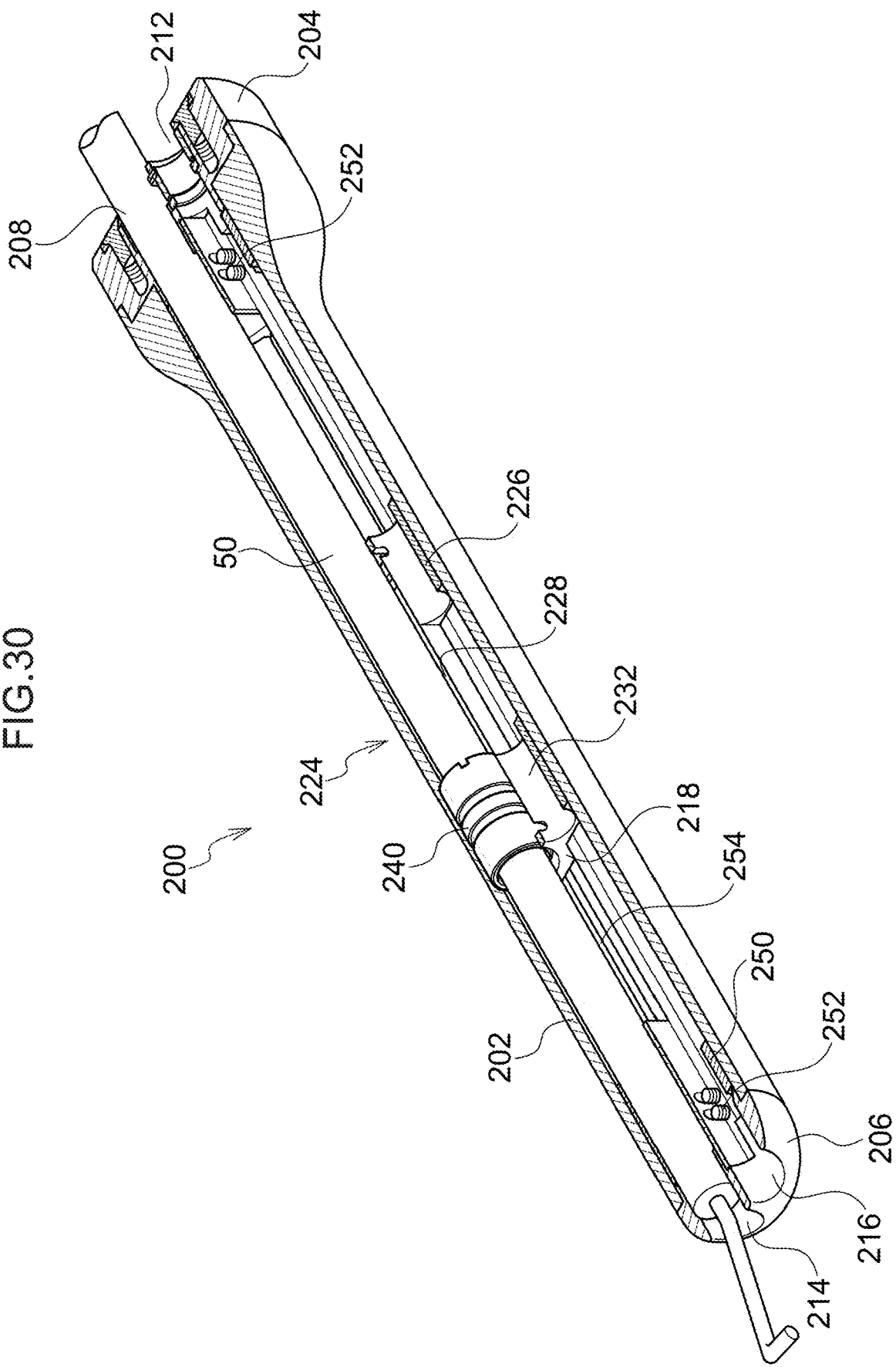
FIG. 30 is an explanatory diagram of operation of an outer tube (when lock of a slider is released).

Although FIG. 30 shows a state where an endoscope is not attached for convenience of explanation, in a case where an endoscope is inserted into the outer tube 200, when the lock of the slider 218 is released, the endoscope moves in conjunction with movement of the treatment tool 50. Accordingly, it is possible to constantly observe a treatment portion with the endoscope.

Figure 31:
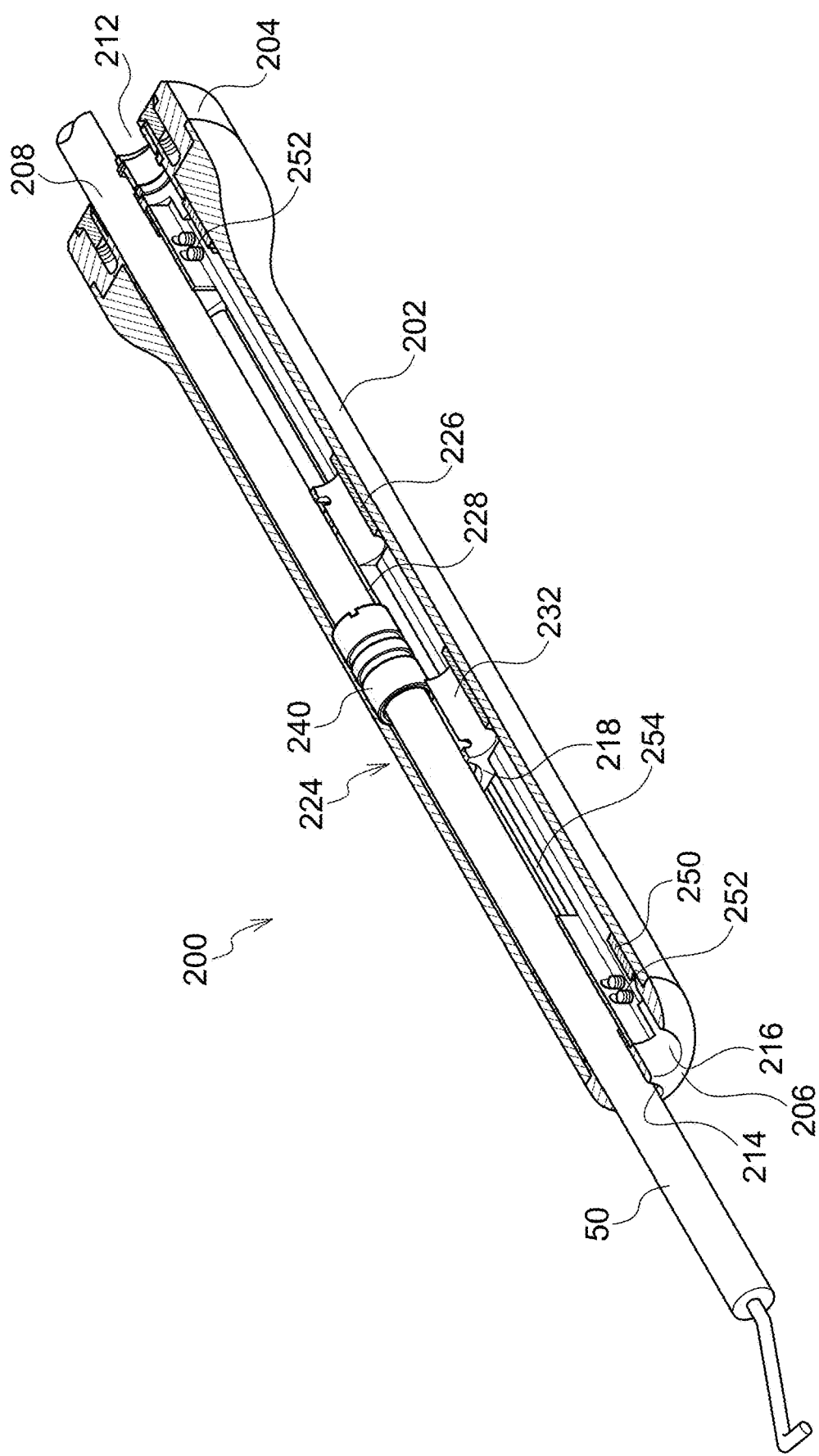
FIG. 31 is an explanatory diagram of operation of an outer tube (when there is a play).
Figure 32:
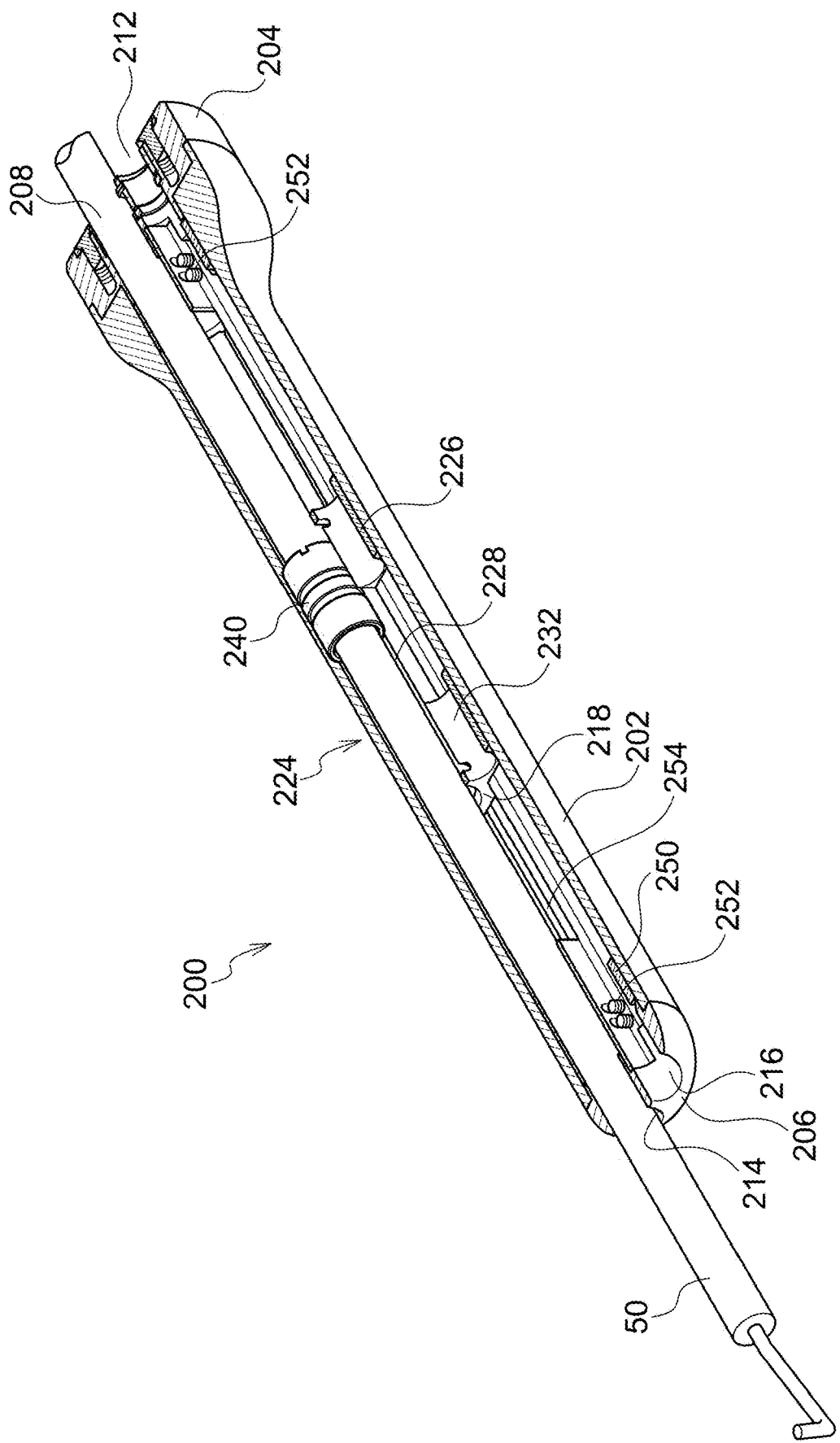
FIG. 32 is an explanatory diagram of operation of an outer tube (when there is a play).

There is considered a case where the treatment tool 50 is slightly axially displaced (slight amplitude). In that case, as shown in FIGS. 31 and 32, movement of the treatment tool 50 is not transmitted to the slider 218, so that only the treatment tool 50 moves. That is, since the treatment tool 50 is held in the slide sleeve 240 that is held so as to be movable with respect to the slider 218, movement of the treatment tool 50 is not transmitted to the slider 218 within the movable range of the slide sleeve 240, so that only the treatment tool 50 moves.

Although FIGS. 31 and 32 show a state where an endoscope is not attached for convenience of explanation, in a case where an endoscope is inserted into the outer tube 200, even if the treatment tool 50 is slightly axially displaced, the endoscope is held in a stationary state without moving. Accordingly, it is possible to prevent a screen of the endoscope from fluctuating due to a slight swing of the treatment tool 50.

As described above, the slider 218 moves in conjunction with the treatment tool 50 only when the treatment tool 50 is largely moved by exceeding the movable range of the slide sleeve 240 and movements with a small amplitude can be cancelled.

When treatment is finished, the treatment tool 50 is extracted from the outer tube 200. When the treatment tool 50 is extracted from the outer tube 200, operation of extracting the treatment tool 50 from the outer tube 200 allows the slider 218 to automatically move to the proximal end portion in the outer tube body so that the slider 218 is locked by the slider lock frame 250. Hereinafter, that lock operation will be described.

Figure 33:
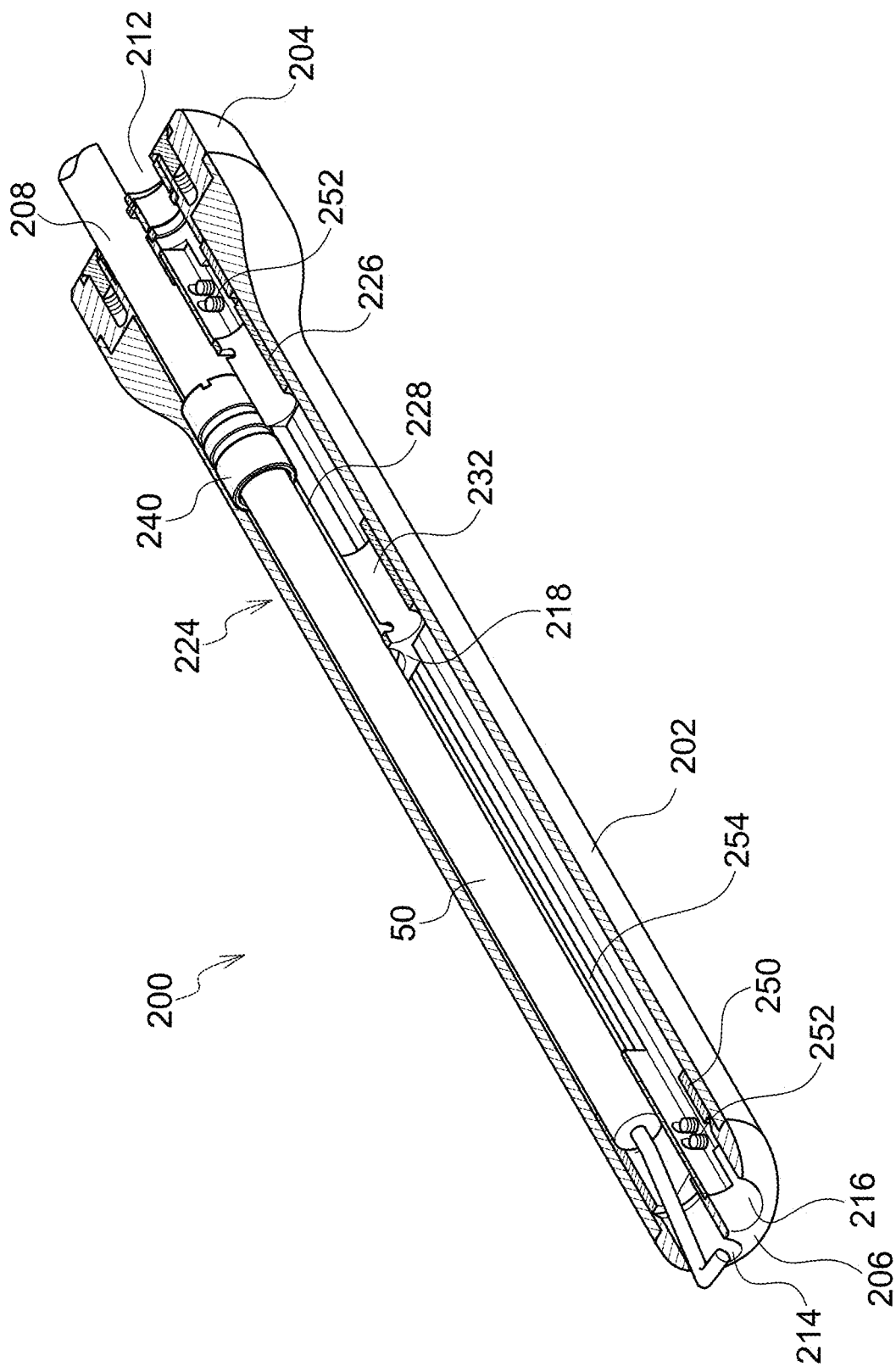
FIG. 33 is an explanatory diagram of operation of an outer tube (when a lock of a slider is started).

When the treatment tool 50 is moved in a direction of extracting the treatment tool 50 from the outer tube 200, first the slide sleeve 240 moves together with the treatment tool 50. When the slide sleeve 240 is brought into contact with the stopper portion 242 on the rear end side, the movement of the slide sleeve 240 stops, and subsequently the slider 218 moves together with the treatment tool 50. In addition, when the slider 218 is brought into contact with the stopper plate 220B on the rear end side, as shown in FIG. 33, the movement of the slider 218 stops, and the treatment tool 50 is extracted from the slide sleeve 240 against the pressing force of the O-rings 230.

When the distal end of the treatment tool 50 passes through the treatment tool engaging portion 256, engagement between the treatment tool 50 and the treatment tool engaging portion 256 is released. When the engagement between the treatment tool 50 and the treatment tool engaging portion 256 is released, the slider lock frame 250 is rotated by the urging force of the slider lock frame urging spring 252. As a result, as shown in FIG. 34, the slider lock portion 254 projects in the moving path of the slider 218 to lock the slider 218. Further, when the treatment tool 50 is moved in a direction in which the treatment tool 50 is to be extracted, as shown in FIG. 27, the treatment tool 50 is extracted from the outer tube 200.

As described above, when the treatment tool 50 is extracted from the outer tube 200, the slider 218 automatically moves to the proximal end part in the outer tube body to be locked by the slider lock frame 250. Thus, at the time of using the outer tube 200 next, it is possible to start using the outer tube 200 in a state where the slider 218 is locked.

As described above, according to the outer tube 200 of the present example, it is possible to move an endoscope in conjunction with a treatment tool. Accordingly, it is possible to constantly take an image of a portion treated with the treatment tool by using the endoscope.

In addition, according to the outer tube 200 of the present example, since there is a "play" in the interlock, it is possible to provide a favorable image.

Further, according to the outer tube 200 of the present example, since operation of inserting the treatment tool allows the treatment tool to be automatically set at an optimum position with respect to the endoscope, quick setting can be performed.

While the example described above is configured to hold an insertion section of an endoscope in the endoscope holding section 226 by using O-rings (not shown) provided in the endoscope holding hole 232, a configuration in which an endoscope is locked by the lock mechanism of an endoscope described in the second embodiment described above (a configuration in which a pin urged to be retractable is engaged with a groove portion formed in an insertion section of an endoscope to lock an endoscope) may be applied.

What is claimed is:

1. An outer tube into which an insertion section of an endoscope that has the insertion section and observes in a body cavity, and an insertion section of a treatment tool that includes the insertion section whose distal end has a treatment portion, are inserted, the outer tube being configured to guide the insertion section of the endoscope and the insertion section of the treatment tool into the body cavity, the outer tube comprising:

a cylindrical outer tube body into which the insertion section of the endoscope and the insertion section of the treatment tool are to be inserted;

a rear end cap provided at a rear end of the outer tube body, the rear end cap including a treatment tool insertion port through which the insertion section of the treatment tool is to be inserted into the outer tube body and an endoscope insertion port through which the insertion section of the endoscope is to be inserted into the outer tube body;

a distal end cap provided at a distal end of the outer tube body, the distal end cap including an endoscope feed port through which the insertion section of the endoscope is to be fed into the body cavity and a treatment tool feed port through which the insertion section of the treatment tool is to be fed into the body cavity;

a mobile object provided in the outer tube body so as to be movable between the distal end cap and the rear end cap in the outer tube body in a direction parallel to an axis of the outer tube body;

an endoscope holding section which is provided in the mobile object, includes an endoscope holding hole, and holds the insertion section of the endoscope inserted into the outer tube body; and a treatment tool holding section which is provided in the mobile object, includes a treatment tool holding hole, and holds the insertion section of the treatment tool inserted into the outer tube body.

2. The outer tube according to claim 1, wherein the treatment tool holding section holds the insertion section of the treatment tool in a movable manner in the direction parallel to the axis of the outer tube body with respect to the mobile object within a predetermined movable range.

3. The outer tube according to claim 2, wherein the treatment tool holding section includes:

a cylindrical second mobile object which is provided so as to be movable in a direction parallel to the axis of the outer tube body with respect to the mobile object, and into which the insertion section of the treatment tool is inserted; and an elastic body which is arranged in the second mobile object, and presses and holds the insertion section of the treatment tool inserted into the second mobile object.

4. The outer tube according to claim 3, wherein:

the mobile object is engaged with the outer tube body by a first frictional force and is provided so as to be movable in the direction parallel to the axis of the outer tube body;

the elastic body is engaged with the insertion section of the treatment tool by a second frictional force larger than the first frictional force, and presses and holds the insertion section of the treatment tool; and the second mobile object is engaged with the mobile object by a third frictional force smaller than the first frictional force and is provided so as to be movable with respect to the mobile object in the direction parallel to the axis of the outer tube body.

5. The outer tube according to claim 1, wherein the treatment tool holding section is capable of adjusting a holding position of the insertion section of the treatment tool with respect to the mobile object.

6. The outer tube according to claim 1, wherein the treatment tool holding section holds the insertion section of treatment tool in a detachable manner.

7. The outer tube according to claim 1, wherein the endoscope holding section holds the insertion section of endoscope in a detachable manner.

8. The outer tube according to claim 7, further comprising:
an endoscope lock pin provided in a retractable manner in either one of the insertion section of the endoscope and the endoscope holding section;
a recessed portion provided in the other one thereof; and
an endoscope lock pin urging member which urges the endoscope lock pin in a projecting direction,
wherein, when the insertion section of the endoscope is inserted into the outer tube, the endoscope lock pin is fitted into the recessed portion to hold the insertion section of the endoscope in the endoscope holding section.

9. The outer tube according to claim 7, wherein the endoscope holding section is capable of adjusting a holding position of the insertion section of the endoscope with respect to the mobile object.

10. The outer tube according to claim 1, wherein the outer tube further includes a movement regulating member which regulates movement of the mobile object.

11. The outer tube according to claim 1, wherein
the mobile object is engaged with the outer tube body by a first frictional force; and
the treatment tool holding section is engaged with the insertion section of the treatment tool by a second frictional force larger than the first frictional force to hold the insertion section of the treatment tool when the insertion section of the treatment tool is inserted into the outer tube body.

12. The outer tube according to claim 11, wherein:
the treatment tool holding section includes a second mobile object which is engaged with the mobile object by a third frictional force smaller than the first frictional force and is provided so as to be movable with respect to the mobile object in the direction parallel to the axis of the outer tube body; and
when the insertion section of treatment tool is inserted into the outer tube body, the insertion section of the treatment tool and the second mobile object are engaged with each other by the second frictional force.

13. The outer tube according to claim 11, wherein the treatment tool holding section includes:
a cylindrical second mobile object which is engaged with the mobile object by a third frictional force smaller than the first frictional force, is provided so as to be movable in a direction parallel to the axis of the outer tube body with respect to the mobile object, and into which the insertion section of the treatment tool is inserted; and
an elastic body which is arranged in the second mobile object and engages with the insertion section of the treatment tool inserted into the second mobile object by the second frictional force to press and hold the insertion section of the treatment tool.

14. The outer tube according to claim 11, further comprising a movement regulating member which regulates movement of the mobile object.

15. The outer tube according to claim 14, wherein:
the movement regulating member regulates movement of the mobile object when the mobile object moves in the outer tube body in a direction to a proximal end to reach a predetermined movement regulation position; and
in a state where movement of the mobile object is regulated, when the insertion section of the treatment tool is inserted by a predetermined amount, the movement regulating member releases regulation of movement of the mobile object.

16. The outer tube according to claim 14, wherein the movement regulating member includes:
a mobile object lock pin provided on a moving path of the mobile object in a retractable manner;
a mobile object lock pin urging member which urges the mobile object lock pin in the projecting direction; and
a mobile object lock releasing member which retracts the mobile object lock pin from the moving path of the mobile object against urging force of the mobile object lock pin urging member.

17. The outer tube according to claim 16, wherein when the insertion section of the treatment tool is inserted into the outer tube body by a predetermined amount, the mobile object lock releasing member is engaged with the insertion section of the treatment tool and retracts the mobile object lock pin from the moving path of the mobile object against the urging force of the mobile object lock pin urging member.

18. The outer tube according to claim 11, wherein the endoscope holding section holds the insertion section of endoscope in a detachable manner.

19. The outer tube according to claim 18, further comprising:
an endoscope lock pin provided in a retractable manner in either one of the insertion section of the endoscope and the endoscope holding section;
a recessed portion provided in the other one thereof; and
an endoscope lock pin urging member which urges the endoscope lock pin in a projecting direction,
wherein, when the insertion section of the endoscope is inserted into the outer tube, the endoscope lock pin is fitted into the recessed portion to hold the insertion section of the endoscope in the endoscope holding section.

20. The outer tube according to claim 18, wherein the endoscope holding section is capable of adjusting a holding position of the insertion section of the endoscope with respect to the mobile object.

* * * * *